US012584132B2

(12) United States Patent
Fujiwara et al.

(10) Patent No.: US 12,584,132 B2
(45) Date of Patent: Mar. 24, 2026

(54) NUCLEIC ACID DRUG TARGETING MURF1

(71) Applicant: Shionogi & Co., Ltd., Osaka (JP)

(72) Inventors: Takahiro Fujiwara, Osaka (JP);
Kazuyoshi Tomita, Osaka (JP);
Kunitaka Nashiki, Osaka (JP); **Ayumi
Nagasawa, Osaka (JP); Ryo
Yoshimoto, Osaka (JP); Takahito Ito**,
Osaka (JP)

(73) Assignee: SHIONOGI & CO., LTD., Osaka (JP)

( * ) Notice: Subject to any disclaimer, the term of this
patent is extended or adjusted under 35
U.S.C. 154(b) by 1094 days.

(21) Appl. No.: 17/630,671

(22) PCT Filed: Jul. 29, 2020

(86) PCT No.: PCT/JP2020/028960
§ 371 (c)(1),
(2) Date: Jan. 27, 2022

(87) PCT Pub. No.: WO2021/020412
PCT Pub. Date: Feb. 4, 2021

(65) Prior Publication Data
US 2022/0267778 A1     Aug. 25, 2022

(30) Foreign Application Priority Data
Jul. 30, 2019     (JP) ................................. 2019-140142

(51) Int. Cl.
*C07H 21/02*     (2006.01)
*A61P 21/00*     (2006.01)
*C12N 15/113*     (2010.01)

(52) U.S. Cl.
CPC .......... *C12N 15/1137* (2013.01); *A61P 21/00*
(2018.01); *C12N 2310/11* (2013.01); *C12N
2310/14* (2013.01); *C12N 2310/141* (2013.01);
*C12N 2310/531* (2013.01)

(58) Field of Classification Search
CPC ......................... C12N 15/113; C12N 2310/14
See application file for complete search history.

(56) References Cited

U.S. PATENT DOCUMENTS

2009/0239934 A1     9/2009   Schmitt-Milas

FOREIGN PATENT DOCUMENTS

| JP | 2009-518022 | 5/2009 |
|----|-------------|--------|
| JP | 2010-184879 | 8/2010 |
| JP | 2015-502365 | 1/2015 |
| JP | 2018-513668 | 5/2018 |
| WO | 2004/045543 | 6/2004 |
| WO | 2013/090457 | 6/2013 |
| WO | 2016/106401 | 6/2016 |
| WO | 2019/113393 | 6/2019 |

OTHER PUBLICATIONS

Fujita et al. (Int. J. Mol. Sci. 2015, 16, 5254-5270).*
International Search Report issued Sep. 29, 2020 in International
(PCT) Application No. PCT/JP2020/028960.
Bodine, Sue C. et al., "Identification of Ubiquitin Ligases Required
for Skeletal Muscle Atrophy", Science, Nov. 2001, vol. 294, pp.
1704-1708.
De Boer, Maarten D. et al., "The temporal responses of protein
synthesis, gene expression and cell signalling in human quadriceps
muscle and patellar tendon to disuse", J Physiol 585.1, 2007, pp.
241-251.
Chen, Bao-lin et al., "Activation of AMPK inhibits cardiomyocyte
hypertrophy by modulating of the FOXO1/MuRF1 signaling path-
way in vitro", Acta Pharmacologica Sinica, 2010, vol. 31, pp.
798-804.
Polge, Cécile et al., "Muscle actin is polyubiquitinylated in vitro and
in vivo and targeted for breakdown by the E3 ligase MuRF1", The
FASEB Journal, 2011, vol. 25, pp. 3790-3802.
Kim, Junghwan et al., "p38 MAPK Participates in Muscle-Specific
RING Finger 1-Mediated Atrophy in Cast-Immobilized Rat Gas-
trocnemius Muscle", The Korean Journal of Physiology and Phar-
macology, 2009, vol. 13, pp. 491-496.
Castillero, Estibaliz et al., "Suppression of atrogin-1 and MuRF1
prevents dexamethasone-induced atrophy of cultured myotubes",
Metabolism Clinical and Experimental, 2013, vol. 62, pp. 1495-
1502.
Adams, Volker et al., "Myocardial expression of Murf-1 and MAFbx
after induction of chronic heart failure: Effect on myocardial con-
tractility", Cardiovascular Research, 2007, vol. 73, pp. 120-129.
International Preliminary Report on Patentability issued Feb. 1,
2022 in corresponding International (PCT) Patent Application No.
PCT/JP2020/028960.

* cited by examiner

*Primary Examiner* — Amy Rose Hudson
(74) *Attorney, Agent, or Firm* — Wenderoth, Lind &
Ponack, L.L.P.

(57)     ABSTRACT

It was found that nucleic acids for the specific targeting
sequences or nucleic acids having the specific sequences
have superior suppression activities of MURF1 expression.
Pharmaceutical compositions including the nucleic acids as
active ingredient are useful for treating or preventing disease
accompanied by one or more symptoms selected from the
group consisting of decrease in muscle mass, decrease in
muscle strength and muscle dysfunction.

11 Claims, No Drawings
Specification includes a Sequence Listing.

NUCLEIC ACID DRUG TARGETING MURF1

TECHNICAL FIELD

This invention relates to nucleic acid medicines targeting MURF1 (muscle RING finger 1). More specifically, it relates to useful nucleic acids for MURF1 as an agent for preventing or treating a disease accompanied by one or more symptoms selected from the group consisting of decrease in muscle mass, decrease in muscle strength and muscle dysfunction.

BACKGROUND ART

Decrease in muscle mass, decrease in muscle strength or muscle dysfunction is a symptom that appears due to aging, disease, or the like. Diseases accompanied by one or more symptoms selected from the group consisting of decrease in muscle mass, decrease in muscle strength and muscle dysfunction include, for example, myogenic muscular atrophy caused by disease of the muscle itself, neurogenic muscular atrophy caused by damage to the motor nerves that command and nourish the muscles, immobility or low movement due to some causes, disused muscular atrophy caused by physical inactivity such as lying down, cachexia caused by a disease such as COPD, heart failure, tuberculosis and the like, or sarcopenia in which muscle volume decreases with aging. However, no therapeutic agent for muscular atrophy has been put on the market so far, and suppression of decrease in muscle mass, decrease in muscle strength or muscle dysfunction is important preventive and clinical task.

MURF1 (Muscle RING-Finger Protein-1) is one of the ubiquitin ligases that are enzymes, that are highly expressed in skeletal muscle and myocardium, and is an enzyme involved in degradation of muscle proteins. It is known that MURF1 is upregulated during muscular atrophy, mice deleted in the gene show resistance to various muscular atrophy, and upregulation of the gene has been confirmed in various muscular atrophy patients in humans (Non-Patent Documents 1, 2 etc.). From these facts, it is suggested that the pharmaceutical composition having suppression activity of MURF1 expression can be used for treating or preventing diseases associated with muscular atrophy.

Patent Document 1 gives an example of miRNA and siRNA as anti-muscular atrophy agents comprising an inhibitor against the expression of MAFbx/atrogin-1 gene and/or Trim63/MuRF1 gene. However, while regarding miRNA, miR-23a is specified in the examples and there is a specific description in the specification, no specific examples of siRNA are described, and no structures or activities are suggested.

siRNA against MURF1 is sold as a research reagent and is known in papers and the like. For example, Non-Patent Document 3 describes siRNA against rat MURF1. Further, Table 13 in Patent Document 2 describes siRNAs against many targets and describes 99 siRNAs against human MURF1 as IDs: 4862450 to 4862549, but no biological data is given including suppression of MURF1 expression.

PRIOR ART DOCUMENT

Patent Document

[Patent Document: 1] JP2010-184879
[Patent Document: 2] WO2004/045543

Non-Patent Document

[Non-Patent Document: 1] Science. 2001; 294(5547): 1704-8
[Non-Patent Document: 2] J Physiol. 2007; 585:241-51
[Non-Patent Document: 3] Acta pharmacologica Sinica, Volume 31, Issue 7, Pages 798-804, 2010

SUMMARY OF INVENTION

Problem to be Solved by the Invention

An object of this invention is to provide nucleic acids having superior suppression activity of MURF1 expression.

Means for Solving the Problem

The present inventors have conducted diligent studies and succeeded in synthesizing novel nucleic acids (siRNAs) having superior suppression activity of MURF1 expression (knockdown activity). Furthermore, we have found target regions in MURF1 mRNA that are particularly related to the knockdown activity of the nucleic acids.

In addition, the nucleic acids of this invention are sufficiently safe for use as pharmaceuticals.

Specifically, this present invention relates to:

(1-1) A nucleic acid suppressing the expression of MURF1 comprising an oligonucleotide consisting of 15 to 30 nucleotides having at least 15 bases or more complementary to the base sequence consisting of positions 188 to 229, 1039 to 1060, 1427 to 1447, 1510 to 1530, or 1715 to 1737 of SEQ ID NO: 609.

(1-2) The nucleic acid according to (1-1) which comprises a base sequence complementary to the base sequence.

(2-1) The nucleic acid according to (1-1) or (1-2) comprising the following base sequence of (a) or (b):

(a) the base sequence of SEQ ID NO: 619, 622 or 623;

(b) the base sequence of at least 15 consecutive bases in the base sequence of SEQ ID NO: 620 or 621.

(2-2) The nucleic acid according to (2-1) which comprises a base sequence complementary to the base sequence.

(3-1) A nucleic acid comprising the base sequence of SEQ ID NO: 24, 26, 30, 56, 60, 104, 106, 146, 212, 218, 314, 360, 382, 384, 388, 390, 484, 504, 514, 536, 556, 584, 586, 588, 594, 596, 606 or 608; or the base sequence of SEQ ID NO: 24, 26, 30, 56, 60, 104, 106, 146, 212, 218, 314, 360, 382, 384, 388, 390, 484, 504, 514, 536, 556, 584, 586, 588, 594, 596, 606 or 608 wherein 1 to 3 bases are deleted, substituted or inserted; and suppressing the expression of MURF1.

(3-2) The nucleic acid according to (3-1) which comprises a base sequence complementary to the base sequence.

(4-1) A nucleic acid comprising the base sequence of SEQ ID NO: 22, 34, 38, 50, 76, 80, 158, 176, 188, 194, 210, 216, 222, 226, 232, 236, 244, 254, 266, 278, 282, 302, 336, 364, 386, 394, 464, 472, 476, 482, 510, 564, 568, 574 or 578; or the base sequence of SEQ ID NO: 22, 34, 38, 50, 76, 80, 158, 176, 188, 194, 210, 216, 222, 226, 232, 236, 244, 254, 266, 278, 282, 302, 336, 364, 386, 394, 464, 472, 476, 482, 510, 564, 568, 574 or 578 wherein 1 to 3 bases are deleted, substituted or inserted at positions 2 to 18; and suppressing the expression of MURF1.

(4-2) The nucleic acid according to (4-1) which comprises a base sequence complementary to the base sequence.

(5) A double-stranded nucleic acid comprising any of the following combinations:

an oligonucleotide consisting of the base sequence of SEQ ID NO: 21 and an oligonucleotide consisting of the base sequence of SEQ ID NO: 22, an oligonucleotide consisting of the base sequence of SEQ ID NO: 23 and an oligonucleotide consisting of the base sequence of SEQ ID NO: 24, an oligonucleotide consisting of the base sequence of SEQ ID NO: 25 or 624 and an oligonucleotide consisting of the base sequence of SEQ ID NO: 26, an oligonucleotide consisting of the base sequence of SEQ ID NO: 29 and an oligonucleotide consisting of the base sequence of SEQ ID NO: 30, an oligonucleotide consisting of the base sequence of SEQ ID NO: 33 and an oligonucleotide consisting of the base sequence of SEQ ID NO: 34, an oligonucleotide consisting of the base sequence of SEQ ID NO: 37 or 625 and an oligonucleotide consisting of the base sequence of SEQ ID NO: 38, an oligonucleotide consisting of the base sequence of SEQ ID NO: 626 and an oligonucleotide consisting of the base sequence of SEQ ID NO: 42, an oligonucleotide consisting of the base sequence of SEQ ID NO: 49 and an oligonucleotide consisting of the base sequence of SEQ ID NO: 50, an oligonucleotide consisting of the base sequence of SEQ ID NO: 55 and an oligonucleotide consisting of the base sequence of SEQ ID NO: 56, an oligonucleotide consisting of the base sequence of SEQ ID NO: 59 and an oligonucleotide consisting of the base sequence of SEQ ID NO: 60, an oligonucleotide consisting of the base sequence of SEQ ID NO: 75 or 627 and an oligonucleotide consisting of the base sequence of SEQ ID NO: 76, an oligonucleotide consisting of the base sequence of SEQ ID NO: 79 and an oligonucleotide consisting of the base sequence of SEQ ID NO: 80, an oligonucleotide consisting of the base sequence of SEQ ID NO: 103 and an oligonucleotide consisting of the base sequence of SEQ ID NO: 104, an oligonucleotide consisting of the base sequence of SEQ ID NO: 105 and an oligonucleotide consisting of the base sequence of SEQ ID NO: 106, an oligonucleotide consisting of the base sequence of SEQ ID NO: 145 and an oligonucleotide consisting of the base sequence of SEQ ID NO: 146, an oligonucleotide consisting of the base sequence of SEQ ID NO: 157 and an oligonucleotide consisting of the base sequence of SEQ ID NO: 158, an oligonucleotide consisting of the base sequence of SEQ ID NO: 175 and an oligonucleotide consisting of the base sequence of SEQ ID NO: 176, an oligonucleotide consisting of the base sequence of SEQ ID NO: 187 and an oligonucleotide consisting of the base sequence of SEQ ID NO: 188, an oligonucleotide consisting of the base sequence of SEQ ID NO: 193 or 628 and an oligonucleotide consisting of the base sequence of SEQ ID NO: 194, an oligonucleotide consisting of the base sequence of SEQ ID NO: 209 and an oligonucleotide consisting of the base sequence of SEQ ID NO: 210, an oligonucleotide consisting of the base sequence of SEQ ID NO: 211 or 629 and an oligonucleotide consisting of the base sequence of SEQ ID NO: 212, an oligonucleotide consisting of the base sequence of SEQ ID NO: 215 and an oligonucleotide consisting of the base sequence of SEQ ID NO: 216, an oligonucleotide consisting of the base sequence of SEQ ID NO: 217 or 630 and an oligonucleotide consisting of the base sequence of SEQ ID NO: 218, an oligonucleotide consisting of the base sequence of SEQ ID NO: 221 or 631 and an oligonucleotide consisting of the base sequence of SEQ ID NO: 222, an oligonucleotide consisting of the base sequence of SEQ ID NO: 225 and an oligonucleotide consisting of the base sequence of SEQ ID NO: 226, an oligonucleotide consisting of the base sequence of SEQ ID NO: 231 and an oligonucleotide consisting of the base sequence of SEQ ID NO: 232, an oligonucleotide consisting of the base sequence of SEQ ID NO: 235 and an oligonucleotide consisting of the base sequence of SEQ ID NO: 236, an oligonucleotide consisting of the base sequence of SEQ ID NO: 243 and an oligonucleotide consisting of the base sequence of SEQ ID NO: 244, an oligonucleotide consisting of the base sequence of SEQ ID NO: 253 and an oligonucleotide consisting of the base sequence of SEQ ID NO: 254, an oligonucleotide consisting of the base sequence of SEQ ID NO: 265 or 632 and an oligonucleotide consisting of the base sequence of SEQ ID NO: 266, an oligonucleotide consisting of the base sequence of SEQ ID NO: 277 and an oligonucleotide consisting of the base sequence of SEQ ID NO: 278, an oligonucleotide consisting of the base sequence of SEQ ID NO: 281 and an oligonucleotide consisting of the base sequence of SEQ ID NO: 282, an oligonucleotide consisting of the base sequence of SEQ ID NO: 301 and an oligonucleotide consisting of the base sequence of SEQ ID NO: 302, an oligonucleotide consisting of the base sequence of SEQ ID NO: 313 and an oligonucleotide consisting of the base sequence of SEQ ID NO: 314, an oligonucleotide consisting of the base sequence of SEQ ID NO: 335 and an oligonucleotide consisting of the base sequence of SEQ ID NO: 336, an oligonucleotide consisting of the base sequence of SEQ ID NO: 359 and an oligonucleotide consisting of the base sequence of SEQ ID NO: 360, an oligonucleotide consisting of the base sequence of SEQ ID NO: 363 and an oligonucleotide consisting of the base sequence of SEQ ID NO: 364, an oligonucleotide consisting of the base sequence of SEQ ID NO: 381 and an oligonucleotide consisting of the base sequence of SEQ ID NO: 382, an oligonucleotide consisting of the base sequence of SEQ ID NO: 383 and an oligonucleotide consisting of the base sequence of SEQ ID NO: 384, an oligonucleotide consisting of the base sequence of SEQ ID NO: 385 and an oligonucleotide consisting of the base sequence of SEQ ID NO: 386, an oligonucleotide consisting of the base sequence of SEQ ID NO: 387 or 633 and an oligonucleotide consisting of the base sequence of SEQ ID NO: 388, an oligonucleotide consisting of the base sequence of SEQ ID NO: 389 or 634 and an oligonucleotide consisting of the base sequence of SEQ ID NO: 390, an oligonucleotide consisting of the base sequence of SEQ ID NO: 393 and an oligonucleotide consisting of the base sequence of SEQ ID NO: 394, an oligonucleotide consisting of the base sequence of SEQ ID NO: 635 and an oligonucleotide consisting of the base sequence of SEQ ID NO: 402, an oligonucleotide consisting of the base sequence of SEQ ID NO: 463 and an oligonucleotide consisting of the base sequence of SEQ ID NO: 464, an oligonucleotide consisting of the base sequence of SEQ ID NO: 471 and an oligonucleotide consisting of the base sequence of SEQ ID NO: 472,

an oligonucleotide consisting of the base sequence of SEQ ID NO: 475 and an oligonucleotide consisting of the base sequence of SEQ ID NO: 476,
an oligonucleotide consisting of the base sequence of SEQ ID NO: 481 or 636 and an oligonucleotide consisting of the base sequence of SEQ ID NO: 482,
an oligonucleotide consisting of the base sequence of SEQ ID NO: 483 or 637 and an oligonucleotide consisting of the base sequence of SEQ ID NO: 484,
an oligonucleotide consisting of the base sequence of SEQ ID NO: 503 and an oligonucleotide consisting of the base sequence of SEQ ID NO: 504,
an oligonucleotide consisting of the base sequence of SEQ ID NO: 509 and an oligonucleotide consisting of the base sequence of SEQ ID NO: 510,
an oligonucleotide consisting of the base sequence of SEQ ID NO: 513 and an oligonucleotide consisting of the base sequence of SEQ ID NO: 514,
an oligonucleotide consisting of the base sequence of SEQ ID NO: 535 and an oligonucleotide consisting of the base sequence of SEQ ID NO: 536,
an oligonucleotide consisting of the base sequence of SEQ ID NO: 555 or 638 and an oligonucleotide consisting of the base sequence of SEQ ID NO: 556,
an oligonucleotide consisting of the base sequence of SEQ ID NO: 563 and an oligonucleotide consisting of the base sequence of SEQ ID NO: 564,
an oligonucleotide consisting of the base sequence of SEQ ID NO: 567 and an oligonucleotide consisting of the base sequence of SEQ ID NO: 568,
an oligonucleotide consisting of the base sequence of SEQ ID NO: 573 and an oligonucleotide consisting of the base sequence of SEQ ID NO: 574,
an oligonucleotide consisting of the base sequence of SEQ ID NO: 577 or 639 and an oligonucleotide consisting of the base sequence of SEQ ID NO: 578,
an oligonucleotide consisting of the base sequence of SEQ ID NO: 583 and an oligonucleotide consisting of the base sequence of SEQ ID NO: 584,
an oligonucleotide consisting of the base sequence of SEQ ID NO: 585 and an oligonucleotide consisting of the base sequence of SEQ ID NO: 586,
an oligonucleotide consisting of the base sequence of SEQ ID NO: 587 and an oligonucleotide consisting of the base sequence of SEQ ID NO: 588,
an oligonucleotide consisting of the base sequence of SEQ ID NO: 593 and an oligonucleotide consisting of the base sequence of SEQ ID NO: 594,
an oligonucleotide consisting of the base sequence of SEQ ID NO: 595 and an oligonucleotide consisting of the base sequence of SEQ ID NO: 596,
an oligonucleotide consisting of the base sequence of SEQ ID NO: 605 and an oligonucleotide consisting of the base sequence of SEQ ID NO: 606, or
an oligonucleotide consisting of the base sequence of SEQ ID NO: 607 and an oligonucleotide consisting of the base sequence of SEQ ID NO: 608.
(6) The nucleic acid according to (5) suppressing the expression of MURF1.
(7) The nucleic acid according to any one of (1-1) to (6), which is siRNA, antisense oligonucleotide, shRNA or miRNA.
(8) The nucleic acid according to (7), which is siRNA having an overhang(s) at the 3' end of the sense and/or the antisense strand.
(9) A pharmaceutical composition comprising the nucleic acid according to any one of (1-1) to (8).

6

(10) The pharmaceutical composition according to (9), which is used for preventing or treating a disease associated with MURF1.
(11) The pharmaceutical composition according to (10), wherein the disease is accompanied by one or more symptoms selected from the group consisting of decrease in muscle mass, decrease in muscle strength and muscle dysfunction.
(12) A method for preventing or treating a disease associated with MURF1, which comprises administering the nucleic acid according to any one of (1-1) to (8).
(13) The nucleic acid according to any one of (1-1) to (8) to manufacture an agent for the prevention or treatment of a disease associated with MURF1.
(14) The nucleic acid according to any one of (1-1) to (8) to prevent or treat a disease associated with MURF1.
(15) The method according to (12) or the nucleic acid according to (13) or (14), wherein the disease is accompanied by one or more symptoms selected from the group consisting of decrease in muscle mass, decrease in muscle strength and muscle dysfunction.

Effects of the Invention

Nucleic acids of this invention show superior suppression activity of MURF1 expression and they are very useful as medicine especially agents to prevent or treat a disease associated with MURF1 such as diseases accompanied by one or more symptoms selected from the group consisting of decrease in muscle mass, decrease in muscle strength and muscle dysfunction.

EMBODIMENTS FOR CARRYING OUT THE INVENTION

Terms used herein, unless otherwise indicated, are used in a sense normally used in the art.

In this invention, a genetic manipulation method which is well known in the art can be used. For example, it is a method described in Molecular Cloning, A Laboratory Manual, Fourth Edition, Cold Spring Harbor Laboratory Press (2002) or Current Protocols Essential Laboratory Techniques, Current Protocols (2012), etc.

"Nucleic acids" in the invention of this application can be any nucleic acid known in the art as nucleic acids that can be used as medicine. For example, they include siRNA, antisense oligonucleotide, shRNA, miRNA and the like. siRNA also includes single-stranded oligonucleotide siRNA (see WO2015/168661 etc.). Further, in the case of antisense oligonucleotide, it can form a double-stranded oligonucleotide together with a sequence which is hybridized to sequence to the oligonucleotide. (see WO2013/089283, etc.).

MURF1 is mentioned as a target gene of the nucleic acid of this invention. For example, human MURF1, mouse Murf1, and the like can be mentioned, but this invention is not limited thereto.

"MURF1" is known protein. The human MURF1 mRNA sequence (GenBank: NM_032588.3) is set forth in SEQ ID NO: 609 and the amino acid sequence (GenPept: NP_115977.2) is set forth in SEQ ID NO: 610 in the Sequence Listing. The mouse Murf1 mRNA sequence (GenBank: NM_001039048.2) is set forth in SEQ ID NO: 611 in the Sequence Listing and the amino acid sequence (GenPept: NP_115977.2) is set forth in SEQ ID NO: 612. "MURF1" of this invention is not limited to these sequences, and as long as the function of the protein consisting of the amino acid sequence of SEQ ID NO: 610 or 612 is maintained, the number of mutations and mutation sites of the amino acid or mRNA are not limited.

"Nucleic acids" of this invention include the nucleic acids suppressing the expression of MURF1 which comprise oligonucleotides consisting of 15 to 30 nucleotides having base sequences of at least 15 bases or more complementary to the base sequences consisting of positions 188 to 229 (more preferably positions 193 to 229), positions 1039 to 1060, positions 1427 to 1447, positions 1510 to 1530, or positions 1715 to 1737 of SEQ ID NO: 609. The nucleic acids may further comprise base sequences complementary to the base sequences. The above each target regions are regions particularly related to nucleic acid knockdown activity in human MURF1 mRNA. Oligonucleotides which are "complementary" to the target region are included in the nucleic acids of this invention, as long as they are substantially complementary sequences, regardless of the length, the presence or absence of nucleotide modifications or mutations. "Substantially complementary sequences" include oligonucleotides having at least 70% or more, preferably 80% or more, more preferably 90% or more, and most preferably 95% or more homology with the completely complementary sequences of the above base sequences. Here, the homology shows the similarity as a score, for example, by BLAST, a search program using algorithm discovered by Altschul et al. (The Journal of Molecular Biology, 215, 403-410 (1990).)

Examples of the nucleic acids suppressing the expression of MURF1 which comprises oligonucleotides consisting of 15 to 30 nucleotides having base sequences of at least 15 bases or more complementary to the base sequences consisting of positions 188 to 229 of SEQ ID NO: 609, include SNG-1 to SNG-19, SNG-305 and SNG-306.

Examples of the nucleic acids suppressing the expression of MURF1 which comprise oligonucleotides consisting of 15 to 30 nucleotides having base sequences of at least 15 bases or more complementary to the base sequence consisting of positions 1039 to 1060 of SEQ ID NO: 609 include SNG-191 to SNG-195, SNG-314 and SNG-315.

Examples of the nucleic acids suppressing the expression of MURF1 which comprise oligonucleotides consisting of 15 to 30 nucleotides having base sequences of at least 15 bases or more complementary to the base sequences consisting of positions 1427 to 1447 of SEQ ID NO: 609 include SNG-239 to SNG-242, SNG-317 and SNG-318.

Examples of the nucleic acids suppressing the expression of MURF1 which comprise oligonucleotides consisting of 15 to 30 nucleotides having base sequences of at least 15 bases or more complementary to the base sequences consisting of positions 1510 to 1530 of SEQ ID NO: 609 include SNG-285 to SNG-298.

Examples of the nucleic acids suppressing the expression of MURF1 which comprise oligonucleotides consisting of 15 to 30 nucleotides having base sequences of at least 15 bases or more complementary to the base sequences consisting of positions 1715 to 1737 of SEQ ID NO: 609 include SNG-300 to SNG-304.

The suppression activity of MURF1 expression (knockdown activity) can be measured by a known method. For example, it can be measured by the method described in Examples described later.

The "nucleic acids" of this invention more preferably include the nucleic acids comprising the following base sequence of (a) or (b).

(a) The base sequence of SEQ ID NO: 619, 622 or 623;
(b) the base sequence of at least 15 consecutive bases in the base sequence of SEQ ID NO: 620 or 621. The nucleic acids may further comprise a base sequence complementary to the base sequence.

The nucleic acids comprising the base sequences of SEQ ID NO: 619 (5'-AACAUCUCCAGGCA-3') include SNG-13 to SNG-19, SNG-305 and SNG-306.

The nucleic acid comprising the base sequence of SEQ ID NO: 622 (5'-AAGCACCAAAUUG) includes SNG-291 to SNG-298.

The nucleic acid comprising the base sequence of SEQ ID NO: 623 (5'-ACAACAUAUAACACA-3') includes SNG-300 to SNG-304.

The base sequence of at least 15 consecutive bases in the base sequence of SEQ ID NO: 620 (5'-UCCAUGUUCU-CAAAGC-3') includes SNG-191 to SNG-195, SNG-314 and SNG-315.

The base sequence of at least 15 consecutive bases in the base sequence of SEQ ID NO: 621 (5'-UAGAAAAGUGU-CCUGUG-3') includes SNG-239 to SNG-242, SNG-317 and SNG-318.

The other embodiments of the "nucleic acids" of this invention include:

(c) the nucleic acid comprising the base sequence of SEQ ID NO: 24, 26, 30, 56, 60, 104, 106, 146, 212, 218, 314, 360, 382, 384, 388, 390, 484, 504, 514, 536, 556, 584, 586, 588, 594, 596, 606 or 608 and suppressing the expression of MURF1;

(d) the nucleic acid comprising the base sequence of SEQ ID NO: 24, 26, 30, 56, 60, 104, 106, 146, 212, 218, 314, 360, 382, 384, 388, 390, 484, 504, 514, 536, 556, 584, 586, 588, 594, 596, 606 or 608 wherein 1 to 3 bases are deleted, substituted or inserted, and suppressing the expression of MURF1;

(e) the nucleic acid comprising the base sequence of SEQ ID NO: 22, 34, 38, 50, 76, 80, 158, 176, 188, 194, 210, 216, 222, 226, 232, 236, 244, 254, 266, 278, 282, 302, 336, 364, 386, 394, 464, 472, 476, 482, 510, 564, 568, 574 or 578 and suppressing the expression of MURF1; or (f) the nucleic acid comprising the base sequence of SEQ ID NO: 22, 34, 38, 50, 76, 80, 158, 176, 188, 194, 210, 216, 222, 226, 232, 236, 244, 254, 266, 278, 282, 302, 336, 364, 386, 394, 464, 472, 476, 482, 510, 564, 568, 574 or 578 wherein 1 to 3 bases are deleted, substituted, or inserted at positions 2 to 18, and suppressing the expression of MURF1. The nucleic acids may further comprise base sequences complementary to the base sequences.

The "nucleic acids" of this invention are included in the nucleic acids of this invention as long as they comprise the base sequences and have suppression activities of human MURF1 expression, regardless of the length or the presence or absence of nucleotide modifications.

In addition, "1 to 3 bases" preferably means 1 or 2 bases. When 2 or 3 bases are mutated, the type of mutations may be the same or different, and the type is 1 or 2 or more selected from deletion, substitution and insertion. The nucleic acids of this invention include the nucleic acids with deletion, substitution or insertion as long as they have suppression activity of the target gene (MURF1).

The other embodiments of the "nucleic acids" of this invention are described below.

The double-stranded nucleic acid comprising an oligonucleotide consisting of the base sequence of SEQ ID NO: 21 and an oligonucleotide consisting of the base sequence of SEQ ID NO: 22 (e.g., SNG-11);

the double-stranded nucleic acid comprising an oligonucleotide consisting of the base sequence of SEQ ID NO: 23 and an oligonucleotide consisting of the base sequence of SEQ ID NO: 24 (e.g., SNG-12);

the double-stranded nucleic acid comprising an oligonucleotide consisting of the base sequence of SEQ ID NO: 25 or 624 and an oligonucleotide consisting of the base sequence of SEQ ID NO: 26 (e.g., SNG-13 or SNG-305);

the double-stranded nucleic acid comprising an oligonucleotide consisting of the base sequence of SEQ ID NO: 29 and an oligonucleotide consisting of the base sequence of SEQ ID NO: 30 (e.g., SNG-15);

the double-stranded nucleic acid comprising an oligonucleotide consisting of the base sequence of SEQ ID NO: 33 and an oligonucleotide consisting of the base sequence of SEQ ID NO: 34 (e.g., SNG-17);

the double-stranded nucleic acid comprising an oligonucleotide consisting of the base sequence of SEQ ID NO: 37 or 625 and an oligonucleotide consisting of the base sequence of SEQ ID NO: 38 (e.g., SNG-19 or SNG-306);

the double-stranded nucleic acid comprising an oligonucleotide consisting of the base sequence of SEQ ID NO: 41 or 626 and an oligonucleotide consisting of the base sequence of SEQ ID NO: 42 (e.g., SNG-21 or SNG-307);

the double-stranded nucleic acid comprising an oligonucleotide consisting of the base sequence of SEQ ID NO: 49 and an oligonucleotide consisting of the base sequence of SEQ ID NO: 50 (e.g., SNG-25);

the double-stranded nucleic acid comprising an oligonucleotide consisting of the base sequence of SEQ ID NO: 55 and an oligonucleotide consisting of the base sequence of SEQ ID NO: 56 (e.g., SNG-28);

the double-stranded nucleic acid comprising an oligonucleotide consisting of the base sequence of SEQ ID NO: 59 and an oligonucleotide consisting of the base sequence of SEQ ID NO: 60 (e.g., SNG-30);

the double-stranded nucleic acid comprising an oligonucleotide consisting of the base sequence of SEQ ID NO: 75 or 627 and an oligonucleotide consisting of the base sequence of SEQ ID NO: 76 (e.g., SNG-38 or SNG-308);

the double-stranded nucleic acid comprising an oligonucleotide consisting of the base sequence of SEQ ID NO: 79 and an oligonucleotide consisting of the base sequence of SEQ ID NO: 80 (e.g., SNG-40);

the double-stranded nucleic acid comprising an oligonucleotide consisting of the base sequence of SEQ ID NO: 103 and an oligonucleotide consisting of the base sequence of SEQ ID NO: 104 (e.g., SNG-52);

the double-stranded nucleic acid comprising an oligonucleotide consisting of the base sequence of SEQ ID NO: 105 and an oligonucleotide consisting of the base sequence of SEQ ID NO: 106 (e.g., SNG-53);

the double-stranded nucleic acid comprising an oligonucleotide consisting of the base sequence of SEQ ID NO: 145 and an oligonucleotide consisting of the base sequence of SEQ ID NO: 146 (e.g., SNG-73);

the double-stranded nucleic acid comprising an oligonucleotide consisting of the base sequence of SEQ ID NO: 157 and an oligonucleotide consisting of the base sequence of SEQ ID NO: 158 (e.g., SNG-79);

the double-stranded nucleic acid comprising an oligonucleotide consisting of the base sequence of SEQ ID NO: 175 and an oligonucleotide consisting of the base sequence of SEQ ID NO: 176 (e.g., SNG-88);

the double-stranded nucleic acid comprising an oligonucleotide consisting of the base sequence of SEQ ID NO: 187 and an oligonucleotide consisting of the base sequence of SEQ ID NO: 188 (e.g., SNG-94);

the double-stranded nucleic acid comprising an oligonucleotide consisting of the base sequence of SEQ ID NO: 193 or 628 and an oligonucleotide consisting of the base sequence of SEQ ID NO: 194 (e.g., SNG-97 or SNG-309);

the double-stranded nucleic acid comprising an oligonucleotide consisting of the base sequence of SEQ ID NO: 209 and an oligonucleotide consisting of the base sequence of SEQ ID NO: 210 (e.g., SNG-105);

the double-stranded nucleic acid comprising an oligonucleotide consisting of the base sequence of SEQ ID NO: 211 or 629 and an oligonucleotide consisting of the base sequence of SEQ ID NO: 212 (e.g., SNG-106 or SNG-310);

the double-stranded nucleic acid comprising an oligonucleotide consisting of the base sequence of SEQ ID NO: 215 and an oligonucleotide consisting of the base sequence of SEQ ID NO: 216 (e.g., SNG-108);

the double-stranded nucleic acid comprising an oligonucleotide consisting of the base sequence of SEQ ID NO: 217 or 630 and an oligonucleotide consisting of the base sequence of SEQ ID NO: 218 (e.g., SNG-109 or SNG-311);

the double-stranded nucleic acid comprising an oligonucleotide consisting of the base sequence of SEQ ID NO: 221 and an oligonucleotide consisting of the base sequence of SEQ ID NO: 222 (e.g., SNG-111);

the double-stranded nucleic acid comprising an oligonucleotide consisting of the base sequence of SEQ ID NO: 225 and an oligonucleotide consisting of the base sequence of SEQ ID NO: 226 (e.g., SNG-113);

the double-stranded nucleic acid comprising an oligonucleotide consisting of the base sequence of SEQ ID NO: 231 and an oligonucleotide consisting of the base sequence of SEQ ID NO: 232 (e.g., SNG-116);

the double-stranded nucleic acid comprising an oligonucleotide consisting of the base sequence of SEQ ID NO: 235 and an oligonucleotide consisting of the base sequence of SEQ ID NO: 236 (e.g., SNG-118);

the double-stranded nucleic acid comprising an oligonucleotide consisting of the base sequence of SEQ ID NO: 243 and an oligonucleotide consisting of the base sequence of SEQ ID NO: 244 (e.g., SNG-122);

the double-stranded nucleic acid comprising an oligonucleotide consisting of the base sequence of SEQ ID NO: 253 and an oligonucleotide consisting of the base sequence of SEQ ID NO: 254 (e.g., SNG-127);

The double-stranded nucleic acid comprising an oligonucleotide consisting of the base sequence of SEQ ID NO: 265 or 632 and an oligonucleotide consisting of the base sequence of SEQ ID NO: 266 (e.g., SNG-133 or SNG-313);

the double-stranded nucleic acid comprising an oligonucleotide consisting of the base sequence of SEQ ID NO: 277 and an oligonucleotide consisting of the base sequence of SEQ ID NO: 278 (e.g., SNG-139);

the double-stranded nucleic acid comprising an oligonucleotide consisting of the base sequence of SEQ ID NO: 281 and an oligonucleotide consisting of the base sequence of SEQ ID NO: 282 (e.g., SNG-141);

the double-stranded nucleic acid comprising an oligo-
nucleotide consisting of the base sequence of SEQ ID
NO: 301 and an oligonucleotide consisting of the base
sequence of SEQ ID NO: 302 (e.g., SNG-151);
the double-stranded nucleic acid comprising an oligo-
nucleotide consisting of the base sequence of SEQ ID
NO: 313 and an oligonucleotide consisting of the base
sequence of SEQ ID NO: 314 (e.g., SNG-157);
the double-stranded nucleic acid comprising an oligo-
nucleotide consisting of the base sequence of SEQ ID
NO: 335 and an oligonucleotide consisting of the base
sequence of SEQ ID NO: 336 (e.g., SNG-168);
the double-stranded nucleic acid comprising an oligo-
nucleotide consisting of the base sequence of SEQ ID
NO: 359 and an oligonucleotide consisting of the base
sequence of SEQ ID NO: 360 (e.g., SNG-180);
the double-stranded nucleic acid comprising an oligo-
nucleotide consisting of the base sequence of SEQ ID
NO: 363 and an oligonucleotide consisting of the base
sequence of SEQ ID NO: 364 (e.g., SNG-182);
the double-stranded nucleic acid comprising an oligo-
nucleotide consisting of the base sequence of SEQ ID
NO: 381 and an oligonucleotide consisting of the base
sequence of SEQ ID NO: 382 (e.g., SNG-191);
the double-stranded nucleic acid comprising an oligo-
nucleotide consisting of the base sequence of SEQ ID
NO: 383 and an oligonucleotide consisting of the base
sequence of SEQ ID NO: 384 (e.g., SNG-192);
the double-stranded nucleic acid comprising an oligo-
nucleotide consisting of the base sequence of SEQ ID
NO: 385 and an oligonucleotide consisting of the base
sequence of SEQ ID NO: 386 (e.g., SNG-193);
the double-stranded nucleic acid comprising an oligo-
nucleotide consisting of the base sequence of SEQ ID
NO: 387 or 633 and an oligonucleotide consisting of
the base sequence of SEQ ID NO: 388 (e.g., SNG-194
or SNG-314);
the double-stranded nucleic acid comprising an oligo-
nucleotide consisting of the base sequence of SEQ ID
NO: 389 or 634 and an oligonucleotide consisting of
the base sequence of SEQ ID NO: 390 (e.g., SNG-195
or SNG-315);
the double-stranded nucleic acid comprising an oligo-
nucleotide consisting of the base sequence of SEQ ID
NO: 393 and an oligonucleotide consisting of the base
sequence of SEQ ID NO: 394 (e.g., SNG-197);
the double-stranded nucleic acid comprising an oligo-
nucleotide consisting of the base sequence of SEQ ID
NO: 401 or 635 and an oligonucleotide consisting of
the base sequence of SEQ ID NO: 402 (e.g., SNG-201
or SNG-316);
the double-stranded nucleic acid comprising an oligo-
nucleotide consisting of the base sequence of SEQ ID
NO: 463 and an oligonucleotide consisting of the base
sequence of SEQ ID NO: 464 (e.g., SNG-232);
the double-stranded nucleic acid comprising an oligo-
nucleotide consisting of the base sequence of SEQ ID
NO: 471 and an oligonucleotide consisting of the base
sequence of SEQ ID NO: 472 (e.g., SNG-236);
the double-stranded nucleic acid comprising an oligo-
nucleotide consisting of the base sequence of SEQ ID
NO: 475 and an oligonucleotide consisting of the base
sequence of SEQ ID NO: 476 (e.g., SNG-238);
the double-stranded nucleic acid comprising an oligo-
nucleotide consisting of the base sequence of SEQ ID

12

NO: 481 or 636 and an oligonucleotide consisting of
the base sequence of SEQ ID NO: 482 (e.g., SNG-241
or SNG-317);
the double-stranded nucleic acid comprising an oligo-
nucleotide consisting of the base sequence of SEQ ID
NO: 483 or 637 and an oligonucleotide consisting of
the base sequence of SEQ ID NO: 484 (e.g., SNG-242
or SNG-318);
the double-stranded nucleic acid comprising an oligo-
nucleotide consisting of the base sequence of SEQ ID
NO: 503 and an oligonucleotide consisting of the base
sequence of SEQ ID NO: 504 (e.g., SNG-252);
the double-stranded nucleic acid comprising an oligo-
nucleotide consisting of the base sequence of SEQ ID
NO: 509 and an oligonucleotide consisting of the base
sequence of SEQ ID NO: 510 (e.g., SNG-255);
the double-stranded nucleic acid comprising an oligo-
nucleotide consisting of the base sequence of SEQ ID
NO: 513 and an oligonucleotide consisting of the base
sequence of SEQ ID NO: 514 (e.g., SNG-257);
the double-stranded nucleic acid comprising an oligo-
nucleotide consisting of the base sequence of SEQ ID
NO: 535 and an oligonucleotide consisting of the base
sequence of SEQ ID NO: 536 (e.g., SNG-268);
the double-stranded nucleic acid comprising an oligo-
nucleotide consisting of the base sequence of SEQ ID
NO: 555 or 638 and an oligonucleotide consisting of
the base sequence of SEQ ID NO: 556 (e.g., SNG-278
or SNG-319);
the double-stranded nucleic acid comprising an oligo-
nucleotide consisting of the base sequence of SEQ ID
NO: 561 and an oligonucleotide consisting of the base
sequence of SEQ ID NO: 562 (e.g., SNG-281);
the double-stranded nucleic acid comprising an oligo-
nucleotide consisting of the base sequence of SEQ ID
NO: 563 and an oligonucleotide consisting of the base
sequence of SEQ ID NO: 564 (e.g., SNG-282);
the double-stranded nucleic acid comprising an oligo-
nucleotide consisting of the base sequence of SEQ ID
NO: 567 and an oligonucleotide consisting of the base
sequence of SEQ ID NO: 568 (e.g., SNG-284);
the double-stranded nucleic acid comprising an oligo-
nucleotide consisting of the base sequence of SEQ ID
NO: 573 and an oligonucleotide consisting of the base
sequence of SEQ ID NO: 574 (e.g., SNG-287);
the double-stranded nucleic acid comprising an oligo-
nucleotide consisting of the base sequence of SEQ ID
NO: 577 or 639 and an oligonucleotide consisting of
the base sequence of SEQ ID NO: 578 (e.g., SNG-289
or SNG-320);
the double-stranded nucleic acid comprising an oligo-
nucleotide consisting of the base sequence of SEQ ID
NO: 583 and an oligonucleotide consisting of the base
sequence of SEQ ID NO: 584 (e.g., SNG-292);
the double-stranded nucleic acid comprising an oligo-
nucleotide consisting of the base sequence of SEQ ID
NO: 585 and an oligonucleotide consisting of the base
sequence of SEQ ID NO: 586 (e.g., SNG-293);
the double-stranded nucleic acid comprising an oligo-
nucleotide consisting of the base sequence of SEQ ID
NO: 587 and an oligonucleotide consisting of the base
sequence of SEQ ID NO: 588 (e.g., SNG-294);
the double-stranded nucleic acid comprising an oligo-
nucleotide consisting of the base sequence of SEQ ID
NO: 593 and an oligonucleotide consisting of the base
sequence of SEQ ID NO: 594 (e.g., SNG-297);

the double-stranded nucleic acid comprising an oligonucleotide consisting of the base sequence of SEQ ID NO: 595 and an oligonucleotide consisting of the base sequence of SEQ ID NO: 596 (e.g., SNG-298);

the double-stranded nucleic acid comprising an oligonucleotide consisting of the base sequence of SEQ ID NO: 605 and an oligonucleotide consisting of the base sequence of SEQ ID NO: 606 (e.g., SNG-303); or the double-stranded nucleic acid comprising an oligonucleotide consisting of the base sequence of SEQ ID NO: 607 and an oligonucleotide consisting of the base sequence of SEQ ID NO: 608 (e.g., SNG-304).

The "nucleic acids" of this invention are preferably siRNAs (including single-stranded oligonucleotide siRNAs), antisense oligonucleotides, shRNAs or miRNAs. More preferably, they are siRNAs or antisense oligonucleotides. Particularly preferably, they are siRNAs or antisense oligonucleotides having oligonucleotides consisting of the base sequences according to the above (3-1), (3-2), (4-1) or (4-2), and siRNAs having the base sequences according to the above (5).

The length of each strand constituting the nucleic acid not comprising the following overhang(s) or terminal modification(s) is preferably 15 to 30 nucleotides. For example, the length of 15 to 25, 17 to 25, 17 to 23, 17 to 21, 19 to 21 nucleotides are described.

When the "nucleic acids" of this invention are siRNAs, the 3'end of the sense strand and/or the antisense strand may include an overhang(s). The "overhang(s)" mean(s) a nucleotide protruding from a double-stranded structure when the 3'end of a single strand of siRNA extends beyond the 5'end of the other strand (or vice versa). Any nucleotide used as an overhang(s) known in the art can be used. For example, 1 to 6 nucleotides, 1 to 5 nucleotides, 1 to 3 nucleotides, 2 or 3 nucleotides (dTdT, U(2'-OMe)U(2'-OMe), U(2'-OMe)A(2'-OMe), A(2'-OMe)U(2'-OMe), A(2'-OMe)A(2'-OMe), U(2'-F)U(2'-F), etc.) are described. It may be complementary or non-complementary to the mRNA of the target sequence.

The nucleic acids of this invention have not only suppression activities of MURF1 expression but also usefulness as medicine and any or all good characters selected from the followings.

a) Improvement of one or more symptoms selected from the group consisting of decrease in muscle mass, decrease in muscle strength and muscle dysfunction.

b) Weak CYP enzyme (e.g., CYP1A2, CYP2C9, CYP2C19, CYP2D6, CYP3A4 or the like) inhibition.

c) Good pharmacokinetics.

d) High metabolic stability.

e) No mutagenicity.

f) Low cardiovascular risk.

g) High solubility.

In the nucleic acids of this invention, a nucleotide(s) may be modified. The nucleic acids with an appropriate modification(s) have any or all characters selected from the followings compared with the nucleic acids without modification(s).

a) High affinity to the target gene.

b) High resistibility to nuclease.

c) Improvement of the pharmacokinetics.

d) High transitivity into tissue.

e) Low immune response and cytotoxicity.

Therefore, the modified nucleic acids become difficult to be degraded in vivo compared with the nucleic acids without modification(s) and can suppress more stably the target gene expression.

Any modification can be used for the nucleic acids of this invention if it is a well-known modification for nucleotide in the art. As the modification for nucleotide, phosphate modifications, nucleic acid base modifications and sugar modifications are known.

Examples of a phosphate modification include a phosphodiester bond in a natural nucleic acid, S-oligo (phosphorothioate), D-oligo (phosphodiester), M-oligo (methylphosphonate), boranophosphate or the like.

Examples of a nucleic acid base modification include 5-methyl cytosine, 5-hydroxymethyl cytosine, 5-propynyl cytosine or the like.

Examples of a sugar modification include 2'-O—$CH_2$—$CH_2$—O—$CH_3$ (2'MOE), LNA (Locked nucleic acid), 2'-OMe, 2'-Fluoro, BNA (Bridged Nucleic Acid), AmNA (see WO2011/052436), TrNA (see WO2014/126229), 2'-Deoxy or the like.

Examples of well-known modifications for nucleotide and methods for modifications in the art disclose in the following Patent Documents.

WO98/39352, WO99/014226, WO2000/056748, WO2003/068795, WO2004/016749, WO2005/021570, WO2005/083124, WO2007/143315, WO2009/071680, WO2011/052436, WO2014/112463, WO2014/126229 or the like.

The 3'end and/or 5'end of the nucleic acids of this invention may have a modifying resides. Hydroxyl protecting resides, debased (Abasic) nucleotide, phosphate ester moiety (resides represented by formula: —OP(=O)(OH)OH or resides represented by formula: —O—P(=S)(OH) or modifying resides thereof) and the like are described.

Further, as long as the nucleic acids of this invention have the above-mentioned base sequences, debased (Abasic) nucleotide(s) may be inserted into the nucleic acids.

The 3'end and/or 5'end of the nucleic acids of this invention (including nucleic acids comprising overhangs and terminal modifications) may be added to a known ligand. To enable tracing of nucleic acids of this invention, to improve the pharmacokinetic s or pharmacodynamics of nucleic acids of this invention, to improve stability or binding affinities of nucleic acids of this invention, to improve intracellular kinetics including intracellular uptake of the nucleic acids of this invention, or to achieve all or any of them, a ligand known in the art can be used to be a comportment of transport carriers consisting of a single molecule or multiple molecules (liposomes, lipid nanoparticles (LNPs), polymers, micelles, or, virus particles, etc.). For example, reporter molecules, lipids (fatty acids, fatty chains, cholesterol, phospholipids, etc.), sugars (N-acetylgalactosamine, etc.), vitamins, peptides (membrane-penetrating peptides, cell-targeting peptides, receptor-binding peptides, endosome escape-promoting peptides, RGD peptides, peptides having high affinity with blood components, or tissue target peptides, etc.), PEG (polyethylene glycol), dye, fluorescent molecule, and the like.

When the above-mentioned ligand(s) is added to the nucleic acids of this invention, it may be via a linker. As the "linker", any linker used in the art can be used. For example, polar linkers (for example, oligonucleotide linkers), alkylene linkers, ethylene glycol linkers, ethylenediamine linkers and the like are described. The linker can be synthesized with reference to a method known in the art.

The linker is preferably an oligonucleotide linker. The length of the oligonucleotide linker is 2 to 10 bases, 2 to 5 bases, 2 bases, 3 bases, 4 bases, and 5 bases. For example, dG, dGdG, dGdGdGdG, dGdGdGdGdG, dT, dTdT, dTdTdTdT, dTdTdTdTdT and the like are described.

The ligands and linkers known in the art and methods for synthesizing thereof are also disclosed, for example, in the following Patent Documents.

WO2009/126933, WO2012/037254, WO2009/069313, WO2009/123185, WO2013/089283, WO2015/105083, WO2018/181428, etc.

The nucleic acids of this invention (or the modified derivatives) can be synthesized according to the usual methods. For example, they can be easily synthesized by an automated nucleic acid synthesizer which is commercially available (e.g., the synthesizer by Applied Biosystems, Dainippon Seiki or the like). A method for synthesizing is solid-phase synthesis using phosphoramidite, solid-phase synthesis using hydrogen phosphonate or the like. For example, it is disclosed in Tetrahedron Letters 22, 1859-1862 (1981), WO2011/052436 or the like.

The nucleic acids of this invention include any pharmaceutically acceptable salts, esters, salts of such esters, or any other equivalents which can provide the biologically active metabolites or residue thereof (directly or indirectly) when they are administrated to an animal including a human. Namely, they include the prodrugs and pharmaceutically acceptable salts of the nucleic acids of this invention, pharmaceutically acceptable salts of the prodrugs, and other bioequivalents.

A "prodrug" means a derivative which is an inactive or lower active form that is converted to an active form (i.e., drug) within the body or cells thereof by the action of endogenous enzymes or other chemicals and/or conditions. The prodrug of nucleic acids of this invention can be prepared according to the methods disclosed in WO93/24510, WO94/26764, WO2004/063331 or the like.

A "pharmaceutically acceptable salt" means a physiologically and pharmaceutically acceptable salt of the nucleic acids of this invention, i.e., a salt that retains the desired biological activity of the nucleic acids and does not impart undesired toxicological effects thereto.

The pharmaceutically acceptable salts include, for example, salts with an alkaline metal (e.g., lithium, sodium, potassium or the like), an alkaline earth metal (e.g., calcium, barium or the like), magnesium, a transition metal (e.g., zinc, iron or the like), ammonia, organic bases (e.g., trimethylamine, triethylamine, dicyclohexylamine, ethanolamine, diethanolamine, triethanolamine, meglumine, diethanolamine, ethylenediamine, pyridine, picoline, quinolone or the like) and salts with amino acids, or salts with inorganic acids (e.g., hydrochloric acid, sulfuric acid, nitric acid, carbonic acid, hydrobromic acid, phosphoric acid, hydroiodic acid or the like) and organic acids (e.g., formic acid, acetic acid, propionic acid, trifluoroacetic acid, citric acid, lactic acid, tartaric acid, oxalic acid, maleic acid, fumaric acid, mandelic acid, glutaric acid, malic acid, benzoic acid, phthalic acid, ascorbic acid, benzenesulfonic acid, p-toluenesulfonic acid, methanesulfonic acid, ethanesulfonic acid or the like). Salts with hydrochloric acid, sulfuric acid, phosphoric acid, tartaric acid, methanesulfonic acid and the like are especially exemplified. These salts can be formed by the usual method.

This invention includes a pharmaceutical composition comprising the nucleic acids of this invention. Any administration method and formulation for the pharmaceutical composition of this invention is available if it is a well-known administration method and formulation in the art in addition to the method of the above-mentioned modification and the method of adding a ligand. An administration method and formulation for nucleic acids is disclosed, for example, in the following documents.

WO2008/042973, WO2009/127060, WO2011/064130, WO2011/123468, WO2011/153542, WO2013/074974, WO2013/075035, WO2013/163258, WO2013/192486 and the like.

A pharmaceutical composition of this invention may be administered in several ways depending upon whether local or systemic treatment is desired and upon the area to be treated. As an administration method, for example, it may be topical (including ophthalmic, intravaginal, intrarectal, intranasal and transdermal), oral or parenteral. Parenteral administration includes intravenous injection or drip, subdermal, intraperitoneal, or intramuscular injection, lung administration by aspiration or inhalation, intrathecal administration, intraventricular administration, and the like.

When the pharmaceutical composition of this invention is topically administered, a formulation such as a transdermal patch, ointment, lotion, cream, gel, drop, suppository, spray, liquid, powder, or the like can be used.

The composition for oral administration includes powder, granule, suspension, or solution dissolved in water or non-aqueous vehicle, capsule, powder, tablet or the like.

The composition for parenteral, intrathecal, or intraventricular administration includes sterile aqueous solutions which contain buffers, diluents and other suitable additives, or the like.

A pharmaceutical composition of this invention can be obtained by mixing an effective amount of the nucleic acids of this invention with various pharmaceutical additives suitable for the administration form, such as excipients, binders, moistening agents, disintegrants, lubricants, diluents and the like as needed. When the composition is an injection, the nucleic acids together with a suitable carrier can be sterilized to give a pharmaceutical composition.

Examples of the excipients include lactose, saccharose, glucose, starch, calcium carbonate, crystalline cellulose, and the like. Examples of the binders include methylcellulose, carboxymethylcellulose, hydroxypropylcellulose, gelatin, polyvinylpyrrolidone and the like. Examples of the disintegrants include carboxymethylcellulose, sodium carboxymethylcellulose, starch, sodium alginate, agar, sodium lauryl sulfate and the like. Examples of the lubricants include talc, magnesium stearate and macrogol, and the like. Cacao oil, macrogol, methylcellulose or the like may be used as base materials of suppositories. When the nucleic acid is prepared as liquid or emulsion or suspending injection, emulsified injections or suspended injections, solubilizing agent, suspending agents, emulsifiers, stabilizers, preservatives, isotonic agents and the like which are usually used may be added as needed. For oral administration, sweetening agents, flavors and the like may be added.

Dosing is dependent on severity and responsiveness of the disease state to be treated, with the course of treatment lasting from several days to several months, or until a cure is effective or a diminution of the disease state is achieved. Optimal dosing schedules can be calculated from measurements of drug accumulation in the body. Persons of ordinary skill in the art can easily determine optimal dosages, dosing methodologies and repetition rates. Optimal dosages can be generally calculated based on IC50 or EC50 in vitro or in vivo animal experiments although they change according to relative efficacy of each nucleic acids. Dosages shown as mg/kg are calculated according to the usual method when, for example, a molecular weight of nucleic acids (derived from the nucleic acids sequence and chemical structure) and effective dosage such as IC50 (derived from experiments) are provided. For example, 0.001 to 10 mg/kg per day can be mentioned. In the case of an injection, it can be administered for a certain period, for example, for 5 to 180 minutes. It can also be administered once to several times a day, or at intervals of one to several days (for example, every two weeks).

The pharmaceutical composition of this invention has suppression activity of MURF1 expression, and therefore it is used for preventing or treating a disease associated with MURF1.

A disease associated with MURF1 includes a disease accompanied by one or more symptoms selected from the group consisting of decrease in muscle mass, decrease in muscle strength and muscle dysfunction. For example, disused muscular atrophy (patients who are expected to be hospitalized and not to use muscle for a certain period of time due to femoral fracture, pneumonia and the like and the diseases are caused from using the gypsum and the like), motor instability, locomotive syndrome, cachexia, ICU-acquired weakness (a decrease in muscle strength occurring while in the ICU room), Chronic Obstructive Pulmonary Disease (COPD), heart failure, tuberculosis, cancer, diabetes, AIDS (Acquired Immunodeficiency Syndrome), sepsis, chronic nephropathy, peripheral neuropathy, muscle loss and the like), drug-induced myopathy (muscle atrophy due to steroid treatment, cancer chemotherapy and the like), one or more symptoms selected from the group consisting of an age-related decrease in muscle mass, decrease in muscle strength and muscle dysfunction (e.g. Sarcopenia), amyotrophic lateral sclerosis (ALS), muscular dystrophy, spinal and bulbar atrophy (SBMA), spinal muscular atrophy (SMA), Charcot-Marie-Tooth disease (CMT), congenital myopathy, Gillan Valley syndrome, Mitochondrial myopathy, congenital metabolic disorders myopathy, polymyositis, dermatomyositis, Sporadic Inclusion Body Myositis, dysphagia (due to apoplexy, cerebrovascular disease, brain infarction, intracerebral hemorrhage, Parkinson's disease, radiotherapy, aging and the like), Cushing disease, primary and/or secondary osteoporosis, osteoarthritis, lumbar pain, metabolic disorders (e.g. diabetes or dyslipidemia), one or more symptoms selected from the group consisting of decrease in diaphragm muscle mass, decrease in diaphragm muscle strength and diaphragm muscle dysfunction due to use respiratory organs and the like, reduction of fracture risk and/or fall risk (e.g. femur, radius, spine, or humerus), one or more symptoms selected from the group consisting of decrease in diaphragm muscle mass, decrease in diaphragm muscle strength, and diaphragm muscle dysfunction in a low gravity environment, and other intractable/hereditary muscle diseases.

EXAMPLE

This invention is further explained by the following Examples, which are not intended to limit the scope of this invention.

Example 1: Design of siRNA Homologous to Human and Mouse siRNAs targeting human and mouse MURF1 mRNA were designed.

The mRNA sequence used in the design is human MURF1 (GenBank: NM_032588.3, SEQ ID NO: 609), mouse Murf1 (GenBank: NM_001039048.2, SEQ ID NO: 611).

The designed siRNAs are double strands, and the double strands consist of a 19-base antisense strand and a 19-base sense strand. The antisense strands are complementary sequences of the mRNA sequences, and the sense strand is a complementary sequence of the antisense strand. The siRNAs were designed so that the 2nd to 17th bases at the 5'end of the antisense strand had 100% homology to human and mouse mRNA. The designed sequences (SNG-1 to SNG320) are shown in Tables 1 to 16. In the table, the Target site indicates the position in SEQ ID NO: 609, and the capital letter in the base sequence means RNA.

TABLE 1

| siRNA | Sense strand (5'→3') | SEQ ID | Antisense strand (5'→3') | SEQ ID | Target site |
|---|---|---|---|---|---|
| SNG-1 | CUUGGAGAAGCAGCUGAUC | 1 | GAUCAGCUGCUUCUCCAAG | 2 | 188-206 |
| SNG-2 | GUUGGAGAAGCAGCUGAUA | 3 | UAUCAGCUGCUUCUCCAAC | 4 | 188-206 |
| SNG-3 | UUGGAGAAGCAGCUGAUCU | 5 | AGAUCAGCUGCUUCUCCAA | 6 | 189-207 |
| SNG-4 | UGGAGAAGCAGCUGAUCUG | 7 | CAGAUCAGCUGCUUCUCCA | 8 | 190-208 |
| SNG-5 | GGGAGAAGCAGCUGAUCUA | 9 | UAGAUCAGCUGCUUCUCCC | 10 | 190-208 |
| SNG-6 | GGAGAAGCAGCUGAUCUGC | 11 | GCAGAUCAGCUGCUUCUCC | 12 | 191-209 |
| SNG-7 | CGAGAAGCAGCUGAUCUGA | 13 | UCAGAUCAGCUGCUUCUCG | 14 | 191-209 |
| SNG-8 | GAGAAGCAGCUGAUCUGCC | 15 | GGCAGAUCAGCUGCUUCUC | 16 | 192-210 |
| SNG-9 | CAGAAGCAGCUGAUCUGCA | 17 | UGCAGAUCAGCUGCUUCUG | 18 | 192-210 |
| SNG-10 | AGAAGCAGCUGAUCUGCCC | 19 | GGGCAGAUCAGCUGCUUCU | 20 | 193-211 |
| SNG-11 | GGAAGCAGCUGAUCUGCCA | 21 | UGGCAGAUCAGCUGCUUCC | 22 | 193-211 |
| SNG-12 | GAAGCAGCUGAUCUGCCCU | 23 | AGGGCAGAUCAGCUGCUUC | 24 | 194-212 |
| SNG-13 | CUAUCUGCCUGGAGAUGUU | 25 | AACAUCUCCAGGCAGAUAG | 26 | 211-229 |
| SNG-14 | UAUCUGCCUGGAGAUGUUU | 27 | AAACAUCUCCAGGCAGAUA | 28 | 212-230 |
| SNG-15 | AUCUGCCUGGAGAUGUUUA | 29 | UAAACAUCUCCAGGCAGAU | 30 | 213-231 |

TABLE 1-continued

| siRNA | Sense strand (5'→3') | SEQ ID | Antisense strand (5'→3') | SEQ ID | Target site |
|---|---|---|---|---|---|
| SNG-16 | UCUGCCUGGAGAUGUUUAC | 31 | GUAAACAUCUCCAGGCAGA | 32 | 214-232 |
| SNG-17 | GCUGCCUGGAGAUGUUUAA | 33 | UUAAACAUCUCCAGGCAGC | 34 | 214-232 |
| SNG-18 | CUGCCUGGAGAUGUUUACC | 35 | GGUAAACAUCUCCAGGCAG | 36 | 215-233 |
| SNG-19 | GUGCCUGGAGAUGUUUACA | 37 | UGUAAACAUCUCCAGGCAC | 38 | 215-233 |
| SNG-20 | UGCCUGGAGAUGUUUACCA | 39 | UGGUAAACAUCUCCAGGCA | 40 | 216-234 |

TABLE 2

| siRNA | Sense strand (5'→3') | SEQ ID | Antisense strand (5'→3') | SEQ ID | Target site |
|---|---|---|---|---|---|
| SNG-21 | GCCUGGAGAUGUUUACCAA | 41 | UUGGUAAACAUCUCCAGGC | 42 | 217-235 |
| SNG-22 | CCUGGAGAUGUUUACCAAG | 43 | CUUGGUAAACAUCUCCAGG | 44 | 218-236 |
| SNG-23 | GCUGGAGAUGUUUACCAAA | 45 | UUUGGUAAACAUCUCCAGC | 46 | 218-236 |
| SNG-24 | CUGGAGAUGUUUACCAAGC | 47 | GCUUGGUAAACAUCUCCAG | 48 | 219-237 |
| SNG-25 | GUGGAGAUGUUUACCAAGA | 49 | UCUUGGUAAACAUCUCCAC | 50 | 219-237 |
| SNG-26 | UGGAGAUGUUUACCAAGCC | 51 | GGCUUGGUAAACAUCUCCA | 52 | 220-238 |
| SNG-27 | GGGAGAUGUUUACCAAGCA | 53 | UGCUUGGUAAACAUCUCCC | 54 | 220-235 |
| SNG-28 | GGAGAUGUUUACCAAGCCA | 55 | UGGCUUGGUAAACAUCUCC | 56 | 221-239 |
| SNG-29 | UGUGCCGGAAGUGUGCCAA | 57 | UUGGCACACUUCCGGCACA | 58 | 268-286 |
| SNG-30 | GUGCCGGAAGUGUGCCAAU | 59 | AUUGGCACACUUCCGGCAC | 60 | 269-287 |
| SNG-31 | AUGACAUCUUCCAGGCUGC | 61 | GCAGCCUGGAAGAUGUCAU | 62 | 286-304 |
| SNG-32 | GUGACAUCUUCCAGGCUGA | 63 | UCAGCCUGGAAGAUGUCAC | 64 | 286-304 |
| SNG-33 | UGACAUCUUCCAGGCUGCA | 65 | UGCAGCCUGGAAGAUGUCA | 66 | 287-305 |
| SNG-34 | CAAAUCCCUACUGGACCAG | 67 | CUGGUCCAGUAGGGAUUUG | 68 | 304-322 |
| SNG-35 | GAAAUCCCUACUGGACCAA | 69 | UUGGUCCAGUAGGGAUUUC | 70 | 304-322 |
| SNG-36 | CAGCUCAGUGUCCAUGUCU | 71 | AGACAUGGACACUGAGCUG | 72 | 329-347 |
| SNG-37 | AGCUCAGUGUCCAUGUCUG | 73 | CAGACAUGGACACUGAGCU | 74 | 330-348 |
| SNG-38 | GGCUCAGUGUCCAUGUCUA | 75 | UAGACAUGGACACUGAGCC | 76 | 330-348 |
| SNG-39 | GCUCAGUGUCCAUGUCUGG | 77 | CCAGACAUGGACACUGAGC | 78 | 331-349 |
| SNG-40 | CCUCAGUGUCCAUGUCUGA | 79 | UCAGACAUGGACACUGAGG | 80 | 331-349 |

TABLE 3

| siRNA | Sense strand (5'→3') | SEQ ID | Antisense strand (5'→3') | SEQ ID | Target site |
|---|---|---|---|---|---|
| SNG-41 | CUCAGUGUCCAUGUCUGGA | 81 | UCCAGACAUGGACACUGAG | 82 | 332-350 |
| SNG-42 | UCAGUGUCCAUGUCUGGAG | 83 | CUCCAGACAUGGACACUGA | 84 | 333-351 |
| SNG-43 | GCAGUGUCCAUGUCUGGAA | 85 | UUCCAGACAUGGACACUGC | 86 | 333-351 |
| SNG-44 | CAGUGUCCAUGUCUGGAGG | 87 | CCUCCAGACAUGGACACUG | 88 | 334-352 |
| SNG-45 | GAGUGUCCAUGUCUGGAGA | 89 | UCUCCAGACAUGGACACUC | 90 | 334-352 |
| SNG-46 | AGUGUCCAUGUCUGGAGGC | 91 | GCCUCCAGACAUGGACACU | 92 | 335-353 |

TABLE 3-continued

| siRNA | Sense strand (5'→3') | SEQ ID | Antisense strand (5'→3') | SEQ ID | Target site |
|---|---|---|---|---|---|
| SNG-47 | GGUGUCCAUGUCUGGAGGA | 93 | UCCUCCAGACAUGGACACC | 94 | 335-353 |
| SNG-48 | GAGUGUACGGCCUGCAGAG | 95 | CUCUGCAGGCCGUACACUC | 96 | 403-421 |
| SNG-49 | CAGUGUACGGCCUGCAGAA | 97 | UUCUGCAGGCCGUACACUG | 98 | 403-421 |
| SNG-50 | AGUGUACGGCCUGCAGAGG | 99 | CCUCUGCAGGCCGUACACU | 100 | 404-422 |
| SNG-51 | GGUGUACGGCCUGCAGAGA | 101 | UCUCUGCAGGCCGUACACC | 102 | 404-422 |
| SNG-52 | GUGUACGGCCUGCAGAGGA | 103 | UCCUCUGCAGGCCGUACAC | 104 | 405-423 |
| SNG-53 | UGUACGGCCUGCAGAGGAA | 105 | UUCCUCUGCAGGCCGUACA | 106 | 406-424 |
| SNG-54 | GUACGGCCUGCAGAGGAAC | 107 | GUUCCUCUGCAGGCCGUAC | 108 | 407-425 |
| SNG-55 | CUACGGCCUGCAGAGGAAA | 109 | UUUCCUCUGCAGGCCGUAG | 110 | 407-425 |
| SNG-56 | UACGGCCUGCAGAGGAACC | 111 | GGUUCCUCUGCAGGCCGUA | 112 | 408-426 |
| SNG-57 | GACGGCCUGCAGAGGAACA | 113 | UGUUCCUCUGCAGGCCGUC | 114 | 408-426 |
| SNG-58 | ACGGCCUGCAGAGGAACCU | 115 | AGGUUCCUCUGCAGGCCGU | 116 | 409-427 |
| SNG-59 | CGGCCUGCAGAGGAACCUG | 117 | CAGGUUCCUCUGCAGGCCG | 118 | 410-428 |
| SNG-60 | GGGCCUGCAGAGGAACCUA | 119 | UAGGUUCCUCUGCAGGCCC | 120 | 410-428 |

TABLE 4

| siRNA | Sense strand (5'→3') | SEQ ID | Antisense strand (5'→3') | SEQ ID | Target site |
|---|---|---|---|---|---|
| SNG-61 | GGCCUGCAGAGGAACCUGC | 121 | GCAGGUUCCUCUGCAGGCC | 122 | 411-429 |
| SNG-62 | CGCCUGCAGAGGAACCUGA | 123 | UCAGGUUCCUCUGCAGGCG | 124 | 411-429 |
| SNG-63 | GCCUGCAGAGGAACCUGCU | 125 | AGCAGGUUCCUCUGCAGGC | 126 | 412-430 |
| SNG-64 | CCUGCAGAGGAACCUGCUG | 127 | CAGCAGGUUCCUCUGCAGG | 128 | 413-431 |
| SNG-65 | GCUGCAGAGGAACCUGCUA | 129 | UAGCAGGUUCCUCUGCAGC | 130 | 413-431 |
| SNG-66 | CUGCAGAGGAACCUGCUGG | 131 | CCAGCAGGUUCCUCUGCAG | 132 | 414-432 |
| SNG-67 | GUGCAGAGGAACCUGCUGA | 133 | UCAGCAGGUUCCUCUGCAC | 134 | 414-432 |
| SNG-68 | UGCAGAGGAACCUGCUGGU | 135 | ACCAGCAGGUUCCUCUGCA | 136 | 415-433 |
| SNG-69 | GCAGAGGAACCUGCUGGUG | 137 | CACCAGCAGGUUCCUCUGC | 138 | 416-434 |
| SNG-70 | CCAGAGGAACCUGCUGGUA | 139 | UACCAGCAGGUUCCUCUGG | 140 | 416-434 |
| SNG-71 | CAGAGGAACCUGCUGGUGG | 141 | CCACCAGCAGGUUCCUCUG | 142 | 417-435 |
| SNG-72 | GAGAGGAACCUGCUGGUGA | 143 | UCACCAGCAGGUUCCUCUC | 144 | 417-435 |
| SNG-73 | AGAGGAACCUGCUGGUGGA | 145 | UCCACCAGCAGGUUCCUCU | 146 | 418-436 |
| SNG-74 | GAGGAACCUGCUGGUGGAG | 147 | CUCCACCAGCAGGUUCCUC | 148 | 419-437 |
| SNG-75 | CAGGAACCUGCUGGUGGAA | 149 | UUCCACCAGCAGGUUCCUG | 150 | 419-437 |
| SNG-76 | AACAGGAGUGCUCCAGUCG | 151 | GGACUGGAGCACUCCUGUU | 152 | 457-475 |
| SNG-77 | GACAGGAGUGCUCCAGUCA | 153 | UGACUGGAGCACUCCUGUC | 154 | 457-475 |
| SNG-78 | ACAGGAGUGCUCCAGUCGG | 155 | CCGACUGGAGCACUCCUGU | 156 | 458-476 |
| SNG-79 | GCAGGAGUGCUCCAGUCGA | 157 | UCGACUGGAGCACUCCUGC | 158 | 458-476 |
| SNG-80 | CAGGAGUGCUCCAGUCGGC | 159 | GCCGACUGGAGCACUCCUG | 160 | 459-477 |

TABLE 5

| siRNA | Sense strand (5'→3') | SEQ ID | Antisense strand (5'→3') | SEQ ID | Target site |
|---|---|---|---|---|---|
| SNG-81 | GAGGAGUGCUCCAGUCGGA | 161 | UCCGACUGGAGCACUCCUC | 162 | 459-477 |
| SNG-82 | AGGAGUGCUCCAGUCGGCC | 163 | GGCCGACUGGAGCACUCCU | 164 | 460-478 |
| SNG-83 | GGGAGUGCUCCAGUCGGCA | 165 | UGCCGACUGGAGCACUCCC | 166 | 460-478 |
| SNG-84 | GGAGUGCUCCAGUCGGCCG | 167 | CGGCCGACUGGAGCACUCC | 168 | 461-479 |
| SNG-85 | CGAGUGCUCCAGUCGGCCA | 169 | UGGCCGACUGGAGCACUCG | 170 | 461-479 |
| SNG-86 | AUGAGAAAUCAACAUCUA | 171 | UAGAUGUUGAUUUCUCAU | 172 | 520-538 |
| SNG-87 | UGAGAAAUCAACAUCUAC | 173 | GUAGAUGUUGAUUUCUCA | 174 | 521-539 |
| SNG-88 | GGAGAAAUCAACAUCUAA | 175 | UUAGAUGUUGAUUUCUCC | 176 | 521-539 |
| SNG-89 | GAGAAAUCAACAUCUACU | 177 | AGUAGAUGUUGAUUUCUC | 178 | 522-540 |
| SNG-90 | AGAAAUCAACAUCUACUG | 179 | CAGUAGAUGUUGAUUUCU | 180 | 523-541 |
| SNG-91 | GGAAAUCAACAUCUACUA | 181 | UAGUAGAUGUUGAUUUCC | 182 | 523-541 |
| SNG-92 | GAAAUCAACAUCUACUGU | 183 | ACAGUAGAUGUUGAUUUC | 184 | 524-542 |
| SNG-93 | AAAUCAACAUCUACUGUC | 185 | GACAGUAGAUGUUGAUUU | 186 | 525-543 |
| SNG-94 | GAAUCAACAUCUACUGUA | 187 | UACAGUAGAUGUUGAUUUC | 188 | 525-543 |
| SNG-95 | AAAUCAACAUCUACUGUCU | 189 | AGACAGUAGAUGUUGAUUU | 190 | 526-544 |
| SNG-96 | AAUCAACAUCUACUGUCUC | 191 | GAGACAGUAGAUGUUGAUU | 192 | 527-545 |
| SNG-97 | GAUCAACAUCUACUGUCUA | 193 | UAGACAGUAGAUGUUGAUC | 194 | 527-545 |
| SNG-98 | AUCAACAUCUACUGUCUCA | 195 | UGAGACAGUAGAUGUUGAU | 196 | 528-546 |
| SNG-99 | UCAACAUCUACUGUCUCAC | 197 | GUGAGACAGUAGAUGUUGA | 198 | 529-547 |
| SNG-100 | GCAACAUCUACUGUCUCAA | 199 | UUGAGACAGUAGAUGUUGC | 200 | 529-547 |

TABLE 6

| siRNA | Sense strand (5'→3') | SEQ ID | Antisense strand (5'→3') | SEQ ID | Target site |
|---|---|---|---|---|---|
| SNG-101 | CAACAUCUACUGUCUCACG | 201 | CGUGAGACAGUAGAUGUUG | 202 | 530-548 |
| SNG-102 | GAACAUCUAGUGUCUCACA | 203 | UGUGAGACAGUAGAUGUUC | 204 | 530-548 |
| SNG-103 | AACAUCUAGUGUCUCACGU | 205 | ACGUGAGACAGUAGAUGUU | 206 | 531-549 |
| SNG-104 | ACAUCUACUGUCUCACGUG | 207 | CACGUGAGACAGUAGAUGU | 208 | 532-550 |
| SNG-105 | GCAUCUACUGUCUCACGUA | 209 | UACGUGAGACAGUAGAUGC | 210 | 532-550 |
| SNG-106 | CAUGUACUGUGUCACGUGU | 211 | ACACGUGAGACAGUAGAUG | 212 | 533-551 |
| SNG-107 | AUCUAGUGUCUCACGUGUG | 213 | CACACGUGAGACAGUAGAU | 214 | 534-552 |
| SNG-108 | GUCUACUGUCUCACGUGUA | 215 | UACACGUGAGACAGUAGAC | 216 | 534-552 |
| SNG-109 | UCUACUGUCUCACGUGUGA | 217 | UCACACGUGAGACAGUAGA | 218 | 535-553 |
| SNG-110 | CUACUGUCUCACGUGUGAG | 219 | CUCACACGUGAGACAGUAG | 220 | 536-554 |
| SNG-111 | GUAGUGUCUCACGUGUGAA | 221 | UUCACACGUGAGACAGUAC | 222 | 536-554 |
| SNG-112 | UACUGUCUCACGUGUGAGG | 223 | CCUCACACGUGAGACAGUA | 224 | 537-555 |
| SNG-113 | GAGUGUCUCACGUGUGAGA | 225 | UCUCACACGUGAGACAUUC | 226 | 537-555 |
| SNG-114 | ACUGUCUCACGUGUGAGGU | 227 | ACCUCACACGUGAGACAGU | 228 | 538-556 |
| SNG-115 | CUGUGUCACGUGUGAGGUG | 229 | CACCUCACACGUGAGACAG | 230 | 539-557 |

TABLE 6-continued

| siRNA | Sense strand (5'→3') | SEQ ID | Antisense strand (5'→3') | SEQ ID | Target site |
|---|---|---|---|---|---|
| SNG-116 | GUGUCUCACGUGUGAGGUA | 231 | UACCUCACACGUGAGACAC | 232 | 539-557 |
| SNG-117 | UGUCUCACGUGUGAGGUGC | 233 | GCACCUCACACGUGAGACA | 234 | 540-558 |
| SNG-118 | GGUCUCACGUGUGAGGUGA | 235 | UCACCUCACACGUGAGACC | 236 | 540-558 |
| SNG-119 | GUCUCACGUGUGAGGUGCC | 237 | GGCACCUCACACGUGAGAC | 238 | 541-559 |
| SNG-120 | CUCUCACGUGUGAGGUGCA | 239 | UGCACCUCACACGUGAGAG | 240 | 541-559 |

TABLE 7

| siRNA | Sense strand (5'→3') | SEQ ID | Antisense strand (5'→3') | SEQ ID | Target site |
|---|---|---|---|---|---|
| SNG-121 | UCUCACGUGUGAGGUGCCC | 241 | GGGCACCUCACACGUGAGA | 242 | 542-560 |
| SNG-122 | GCUCACGUGUGAGGUGCCA | 243 | UGGCACCUCACACGUGAGC | 244 | 542-560 |
| SNG-123 | CAUGUGCAAGGUGUUUGGG | 245 | CCCAAACACCUUGCACAUG | 246 | 569-587 |
| SNG-124 | GAUGUGCAAGGUGUUUGGA | 247 | UCCAAACACCUUGCACAUC | 248 | 569-587 |
| SNG-125 | AUGUGCAAGGUGUUUGGGA | 249 | UCCCAAACACCUUGCACAU | 250 | 570-588 |
| SNG-126 | GUAUCUCCAUGCUGGUGGC | 251 | GCCACCAGCAUGGAGAUAC | 252 | 658-676 |
| SNG-127 | CUAUCUCCAUGCUGGUGGA | 253 | UCCACCAGCAUGGAGAUAG | 254 | 658-676 |
| SNG-128 | UAUCUCCAUGCUGGUGGCG | 255 | CGCCACCAGCAUGGAGAUA | 256 | 659-677 |
| SNG-129 | GAUCUCCAUGCUGGUGGCA | 257 | UGCCACCAGCAUGGAGAUC | 258 | 659-677 |
| SNG-130 | AUCUCCAUGCUGGUGGCGG | 259 | CCGCCACCAGCAUGGAGAU | 260 | 660-678 |
| SNG-131 | GUCUCCAUGCUGGUGGCGA | 261 | UCGCCACCAGCAUGGAGAC | 262 | 660-678 |
| SNG-132 | UCUCCAUGCUGGUGGCGGG | 263 | CCCGCCACCAGCAUGGAGA | 264 | 661-679 |
| SNG-133 | GCUCCAUGCUGGUGGCGGA | 265 | UCCGCCACCAGCAUGGAGC | 266 | 661-679 |
| SNG-134 | CUCCAUGCUGGUGGCGGGG | 267 | CCCCGCCACCAGCAUGGAG | 268 | 662-680 |
| SNG-135 | GUCCAUGCUGGUGGCGGGA | 269 | UCCCGCCACCAGCAUGGAC | 270 | 662-680 |
| SNG-136 | UCGAGUGACCAAGGAGAAC | 271 | GUUCUCCUUGGUCACUCGA | 272 | 725-743 |
| SNG-137 | GCGAGUGACCAAGGAGAAA | 273 | UUUCUCCUUGGUCACUCGC | 274 | 725-743 |
| SNG-138 | GUUGCUGCAGCGGAUCACG | 275 | CGUGAUCCGCUGCAGCAAC | 276 | 818-836 |
| SNG-139 | CUUGCUGCAGCGGAUCACA | 277 | UGUGAUCCGCUGCAGCAAG | 278 | 818-836 |
| SNG-140 | UUGCUGCAGCGGAUCACGC | 279 | GCGUGAUCCGCUGCAGCAA | 280 | 819-837 |

TABLE 8

| siRNA | Sense strand (5'→3') | SEQ ID | Antisense strand (5'→3') | SEQ ID | Target site |
|---|---|---|---|---|---|
| SNG-141 | GUGCUGCAGCGGAUCACGA | 281 | UCGUGAUCCGCUGCAGCAC | 282 | 819-837 |
| SNG-142 | UGCUGCAGCGGAUCACGCA | 283 | UGCGUGAUCCGCUGCAGCA | 284 | 820-838 |
| SNG-143 | GCUGCAGCGGAUCACGCAG | 285 | CUGCGUGAUCCGCUGCAGC | 286 | 821-839 |
| SNG-144 | CCUGCAGCGGAUCACGCAA | 287 | UUGCGUGAUCCGCUGCAGG | 288 | 821-839 |
| SNG-145 | CUGCAGCGGAUCACGCAGG | 289 | CCUGCGUGAUCCGCUGCAG | 290 | 822-840 |
| SNG-146 | GUGCAGCGGAUCACGCAGA | 291 | UCUGCGUGAUCCGCUGCAC | 292 | 822-840 |

TABLE 8-continued

| siRNA | Sense strand (5'→3') | SEQ ID | Antisense strand (5'→3') | SEQ ID | Target site |
|---|---|---|---|---|---|
| SNG-147 | UGCAGCGGAUCACGCAGGA | 293 | UCCUGCGUGAUCCGCUGCA | 294 | 823-841 |
| SNG-148 | GCAGCGGAUCACGCAGGAG | 295 | CUCCUGCGUGAUCCGCUGC | 296 | 824-842 |
| SNG-149 | CCAGCGGAUCACGCAGGAA | 297 | UUCCUGCGUGAUCCGCUGG | 298 | 824-842 |
| SNG-150 | CAGCGGAUCACGCAGGAGC | 299 | GCUCCUGCGUGAUCCGCUG | 300 | 825-843 |
| SNG-151 | GAGCGGAUCACGCAGGAGA | 301 | UCUCCUGCGUGAUCCGCUC | 302 | 825-843 |
| SNG-152 | AGCGGAUCACGCAGGAGCA | 303 | UGCUCCUGCGUGAUCCGCU | 304 | 826-844 |
| SNG-153 | GCGGAUCACGCAGGAGCAG | 305 | CUGCUCCUGCGUGAUCCGC | 306 | 827-845 |
| SNG-154 | CCGGAUCACGCAGGAGCAA | 307 | UUGCUCCUGCGUGAUCCGG | 308 | 827-845 |
| SNG-155 | CGGAUCACGCAGGAGCAGG | 309 | CCUGCUCCUGCGUGAUCCG | 310 | 828-846 |
| SNG-156 | GGGAUCACGCAGGAGCAGA | 311 | UCUGCUCCUGCGUGAUCCC | 312 | 828-846 |
| SNG-157 | GGAUCACGCAGGAGCAGGA | 313 | UCCUGCUCCUGCGUGAUCC | 314 | 829-847 |
| SNG-158 | GAUCACGCAGGAGCAGGAG | 315 | CUCCUGCUCCUGCGUGAUC | 316 | 830-848 |
| SNG-159 | CAUCACGCAGGAGCAGGAA | 317 | UUCCUGCUCCUGCGUGAUG | 318 | 830-848 |
| SNG-160 | AUCACGCAGGAGCAGGAGA | 319 | UCUCCUGCUCCUGCGUGAU | 320 | 831-849 |

TABLE 9

| siRNA | Sense strand (5'→3') | SEQ ID | Antisense strand (5'→3') | SEQ ID | Target site |
|---|---|---|---|---|---|
| SNG-161 | CUGCCAUCCAGUCCCUGGA | 321 | UCCAGGGACUGGAUGGCAG | 322 | 925-943 |
| SNG-162 | UGCCAUCCAGUCCCUGGAC | 323 | GUCCAGGGACUGGAUGGCA | 324 | 926-944 |
| SNG-163 | GGCCAUCCAGUCCCUGGAA | 325 | UUCCAGGGACUGGAUGGCC | 326 | 926-944 |
| SNG-164 | CUUCCAAGGGCUGCCAGCU | 327 | AGCUGGCAGCCCUUGGAAG | 328 | 1006-1024 |
| SNG-165 | UUCCAAGGGCUGCCAGCUG | 329 | CAGCUGGCAGCCCUUGGAA | 330 | 1007-1025 |
| SNG-166 | GUCCAAGGGCUGCCAGCUA | 331 | UAGCUGGCAGCCCUUGGAC | 332 | 1007-1025 |
| SNG-167 | UCCAAGGGCUGCCAGCUGG | 333 | CCAGCUGGCAGCCCUUGGA | 334 | 1008-1026 |
| SNG-168 | GCCAAGGGCUGCCAGCUGA | 335 | UCAGCUGGCAGCCCUUGGC | 336 | 1008-1026 |
| SNG-169 | CCAAGGGCUGCCAGCUGGG | 337 | CCCAGCUGGCAGCCCUUGG | 338 | 1009-1027 |
| SNG-170 | GCAAGGGCUGCCAGCUGGA | 339 | UCCAGCUGGCAGCCCUUGC | 340 | 1009-1027 |
| SNG-171 | CAAGGGCUGCCAGCUGGGG | 341 | CCCCAGCUGGCAGCCCUUG | 342 | 1010-1028 |
| SNG-172 | GAAGGGCUGCCAGCUGGGA | 343 | UCCCAGCUGGCAGCCCUUC | 344 | 1010-1028 |
| SNG-173 | AAGGGCUGCCAGCUGGGGA | 345 | UCCCCAGCUGGCAGCCCUU | 346 | 1011-1029 |
| SNG-174 | AGGGCUGCCAGCUGGGGAA | 347 | UUCCCCAGCUGGCAGCCCU | 348 | 1012-1030 |
| SNG-175 | GGGCUGCCAGCUGGGGAAG | 349 | CUUCCCCAGCUGGCAGCCC | 350 | 1013-1031 |
| SNG-176 | CGGCUGCCAGCUGGGGAAA | 351 | UUUCCCCAGCUGGCAGCCG | 352 | 1013-1031 |
| SNG-177 | GGCUGCCAGCUGGGGAAGA | 353 | UCUUCCCCAGCUGGCAGCC | 354 | 1014-1032 |
| SNG-178 | GCUGCCAGCUGGGGAAGAC | 355 | GUCUUCCCCAGCUGGCAGC | 356 | 1015-1033 |
| SNG-179 | CCUGCCAGCUGGGGAAGAA | 357 | UUCUUCCCCAGCUGGCAGG | 358 | 1015-1033 |
| SNG-180 | CUGCCAGCUGGGGAAGACA | 359 | UGUCUUCCCCAGCUGGCAG | 360 | 1016-1034 |

TABLE 10

| siRNA | Sense strand (5'→3') | SEQ ID | Antisense strand (5'→3') | SEQ ID | Target site |
|---|---|---|---|---|---|
| SNG-181 | UGCCAGCUGGGGAAGACAG | 361 | CUGUCUUCCCCAGCUGGCA | 362 | 1017-1035 |
| SNG-182 | GGCCAGCUGGGGAAGACAA | 363 | UUGUCUUCCCCAGCUGGCC | 364 | 1017-1035 |
| SNG-183 | GCCAGCUGGGGAAGACAGA | 365 | UCUGUCUUCCCCAGCUGGC | 366 | 1018-1036 |
| SNG-184 | CCAGCUGGGGAAGACAGAG | 367 | CUCUGUCUUCCCCAGCUGG | 368 | 1019-1037 |
| SNG-185 | GCAGCUGGGGAAGACAGAA | 369 | UUCUGUCUUCCCCAGCUGC | 370 | 1019-1037 |
| SNG-186 | CAGCUGGGGAAGACAGAGC | 371 | GCUCUGUCUUCCCCAGCUG | 372 | 1020-1038 |
| SNG-187 | GAGCUGGGGAAGACAGAGA | 373 | UCUCUGUCUUCCCCAGCUC | 374 | 1020-1038 |
| SNG-188 | AGCUGGGGAAGACAGAGCA | 375 | UGCUCUGUCUUCCCCAGCU | 376 | 1021-1039 |
| SNG-189 | GCUGGGGAAGACAGAGCAG | 377 | CUGCUCUGUCUUCCCCAGC | 378 | 1022-1040 |
| SNG-190 | CCUGGGGAAGACAGAGCAA | 379 | UUGCUCUGUCUUCCCCAGG | 380 | 1022-1040 |
| SNG-191 | AGGGCUUUGAGAACAUGGA | 381 | UCCAUGUUCUCAAAGCCCU | 382 | 1039-1057 |
| SNG-192 | GGGCUUUGAGAACAUGGAC | 383 | GUCCAUGUUCUCAAAGCCC | 384 | 1040-1058 |
| SNG-193 | CGGCUUUGAGAACAUGGAA | 385 | UUCCAUGUUCUCAAAGCCG | 386 | 1040-1058 |
| SNG-194 | GGCUUUGAGAACAUGGACU | 387 | AGUCCAUGUUCUCAAAGCC | 388 | 1041-1059 |
| SNG-195 | GCUUUGAGAACAUGGACUU | 389 | AAGUCCAUGUUCUCAAAGC | 390 | 1042-1060 |
| SNG-196 | GAGCCAUUGACUUUGGGAC | 391 | GUCCCAAAGUCAAUGGCUC | 392 | 1099-1117 |
| SNG-197 | CAGCCAUUGAGUUUGGGAA | 393 | UUCCCAAAGUCAAUGGCUG | 394 | 1099-1117 |
| SNG-198 | AGCCAUUGACUUUGGGACA | 395 | UGUCCCAAAGUCAAUGGCU | 396 | 1100-1118 |
| SNG-199 | GCCAUUGACUUUGGGACAG | 397 | CUGUCCCAAAGUCAAUGGC | 398 | 1101-1119 |
| SNG-200 | CCCAUUGACUUUGGGACAA | 399 | UUGUCCCAAAGUCAAUGGG | 400 | 1101-1119 |

TABLE 11

| siRNA | Sense strand (5'→3') | SEQ ID | Antisense strand (5'→3') | SEQ ID | Target site |
|---|---|---|---|---|---|
| SNG-201 | CCAUUGACUUUGGGACAGA | 401 | UCUGUCCCAAAGUCAAUGG | 402 | 1102-1120 |
| SNG-202 | CAUUGACUUUGGGACAGAU | 403 | AUCUGUCCCAAAGUCAAUG | 404 | 1103-1121 |
| SNG-203 | AUUGACUUUGGGACAGAUG | 405 | CAUCUGUCCCAAAGUCAAU | 406 | 1104-1122 |
| SNG-204 | GUUGACUUUGGGACAGAUA | 407 | UAUCUGUCCCAAAGUCAAC | 408 | 1104-1122 |
| SNG-205 | UUGACUUUGGGACAGAUGA | 409 | UCAUCUGUCCCAAAGUCAA | 410 | 1105-1123 |
| SNG-206 | UGACUUUGGGACAGAUGAG | 411 | CUCAUCUGUCCCAAAGUCA | 412 | 1106-1124 |
| SNG-207 | GGACUUUGGGACAGAUGAA | 413 | UUCAUCUGUCCCAAAGUCC | 414 | 1106-1124 |
| SNG-208 | GACUUUGGGACAGAUGAGG | 415 | CCUCAUCUGUCCCAAAGUC | 416 | 1107-1125 |
| SNG-209 | CACUUUGGGACAGAUGAGA | 417 | UCUCAUCUGUCCCAAAGUG | 418 | 1107-1125 |
| SNG-210 | ACUUUGGGACAGAUGAGGA | 419 | UCCUCAUCUGUCCCAAAGU | 420 | 1108-1126 |
| SNG-211 | CUUUGGGACAGAUGAGGAA | 421 | UUCCUCAUCUGUCCCAAAG | 422 | 1109-1127 |
| SNG-212 | GAUGUCUUCUCUCUGCUCA | 423 | UGAGCAGAGAGAAGACAUC | 424 | 1328-1346 |
| SNG-213 | AUGUCUUCUCUCUGCUCAG | 425 | CUGAGCAGAGAGAAGACAU | 426 | 1329-1347 |
| SNG-214 | GUGUCUUCUCUCUGCUCAA | 427 | UUGAGCAGAGAGAAGACAC | 428 | 1329-1347 |
| SNG-215 | UGUCUUGUGUCUGCUCAGA | 429 | UCUGAGCAGAGAGAAGACA | 430 | 1330-1348 |

TABLE 11-continued

| siRNA | Sense strand (5'→3') | SEQ ID | Antisense strand (5'→3') | SEQ ID | Target site |
|---|---|---|---|---|---|
| SNG-216 | GUCUUCUCUCUGCUCAGAG | 431 | CUCUGAGCAGAGAGAAGAC | 432 | 1331-1349 |
| SNG-217 | CUCUUCUGUCUGGUCAGAA | 433 | UUCUGAGCAGAGAGAAGAG | 434 | 1331-1349 |
| SNG-218 | UCUUCUCUCUGCUCAGAGA | 435 | UCUCUGAGCAGAGAGAAGA | 436 | 1332-1350 |
| SNG-219 | CUUCUCUCUGCUCAGAGAG | 437 | CUCUCUGAGCAGAGAGAAG | 438 | 1333-1351 |
| SNG-220 | GUUCUCUCUGCUCAGAGAA | 439 | UUCUCUGAGCAGAGAGAAC | 440 | 1333-1351 |

TABLE 12

| siRNA | Sense strand (5'→3') | SEQ ID | Antisense strand (5'→3') | SEQ ID | Target site |
|---|---|---|---|---|---|
| SNG-221 | UUCUCUCUGCUCAGAGAGC | 441 | GCUCUCUGAGCAGAGAGAA | 442 | 1334-1352 |
| SNG-222 | GUCUCUCUGCUCAGAGAGA | 443 | UCUCUCUGAGCAGAGAGAC | 444 | 1334-1352 |
| SNG-223 | UCUCUCUGCUCAGAGAGCA | 445 | UGCUCUCUGAGCAGAGAGA | 446 | 1335-1353 |
| SNG-224 | CUCUCUGCUCAGAGAGCAG | 447 | CUGCUCUCUGAGCAGAGAG | 448 | 1336-1354 |
| SNG-225 | GUCUCUGCUCAGAGAGCAA | 449 | UUGCUCUCUGAGCAGAGAC | 450 | 1336-1354 |
| SNG-226 | UCUCUGCUCAGAGAGCAGG | 451 | CCUGCUCUGUGAGCAGAGA | 452 | 1337-1355 |
| SNG-227 | GCUCUGCUCAGAGAGCAGA | 453 | UCUGCUCUCUGAGCAGAGC | 454 | 1337-1355 |
| SNG-228 | CUCUGCUCAGAGAGCAGGG | 455 | CCCUGCUCUCUGAGCAGAG | 456 | 1338-1356 |
| SNG-229 | GUCUGCUCAGAGAGUAGGA | 457 | UCCUGCUCUCUGAGCAGAC | 458 | 1338-1356 |
| SNG-230 | UCUGCUCAGAGAGCAGGGA | 459 | UCCCUGCUCUCUGAGCAGA | 460 | 1339-1357 |
| SNG-231 | CUGCUCAGAGAGCAGGGAC | 461 | GUCCCUGCUCUCUGAGCAG | 462 | 1340-1358 |
| SNG-232 | GUGCUCAGAGAGCAGGGAA | 463 | UUCCCUGCUCUCUGAGCAC | 464 | 1340-1358 |
| SNG-233 | UGCUCAGAGAGCAGGGACU | 465 | AGUCCCUGCUCUCUGAGCA | 466 | 1341-1359 |
| SNG-234 | GCUCAGAGAGCAGGGACUA | 467 | UAGUCCCUGCUGUCUGAGC | 468 | 1342-1360 |
| SNG-235 | CUCAGAGAGCAGGGACUAG | 469 | CUAGUCCCUGCUCUCUGAG | 470 | 1343-1361 |
| SNG-236 | GUCAGAGAGCAGGGACUAA | 471 | UUAGUCCCUGCUCUCUGAC | 472 | 1343-1361 |
| SNG-237 | UCAGAGAGCAGGGACUAGG | 473 | CCUAGUCCCUGCUCUCUGA | 474 | 1344-1362 |
| SNG-238 | GCAGAGAGCAGGGACUAGA | 475 | UCUAGUCCCUGCUCUCUGC | 476 | 1344-1362 |
| SNG-239 | CACACAGGACACUUUUCUA | 477 | UAGAAAAGUGUCCUGUGUG | 478 | 1427-1445 |
| SNG-240 | ACACAGGACACUUUUCUAC | 479 | GUAGAAAAGUGUCCUGUGU | 480 | 1428-1446 |

TABLE 13

| siRNA | Sense strand (5'→3') | SEQ ID | Antisense strand (5'→3') | SEQ ID | Target site |
|---|---|---|---|---|---|
| SNG-241 | GCACAGGACACUUUUCUAA | 481 | UUAGAAAAGUGUCCUGUGC | 482 | 1428-1446 |
| SNG-242 | CACAGGACACUUUUCUACA | 483 | UGUAGAAAAGUGUCCUGUG | 484 | 1429-1447 |
| SNG-243 | CAUUUUUAAAAUGUGAUUU | 485 | AAAUCACAUUUUAAAAAUG | 486 | 1473-1491 |
| SNG-244 | AUUUUUAAAAUGUGAUUUU | 487 | AAAAUCACAUUUUAAAAAU | 488 | 1474-1492 |
| SNG-245 | UUUUUAAAAUGUGAUUUUU | 489 | AAAAAUCACAUUUUAAAAA | 490 | 1475-1493 |
| SNG-246 | UUUUAAAAUGUGAUUUUUG | 491 | CAAAAAUCACAUUUUAAAA | 492 | 1476-1494 |

TABLE 13-continued

| siRNA | Sense strand (5'→3') | SEQ ID | Antisense strand (5'→3') | SEQ ID | Target site |
|---|---|---|---|---|---|
| SNG-247 | GUUUAAAAUGUGAUUUUUA | 493 | UAAAAAUCACAUUUUAAAC | 494 | 1476-1494 |
| SNG-248 | UUUAAAAUGUGAUUUUUGU | 495 | ACAAAAAUCACAUUUUAAA | 496 | 1477-1495 |
| SNG-249 | UUAAAAUGUCAUUUUUGUA | 497 | UACAAAAAUCACAUUUUAA | 498 | 1478-1496 |
| SNG-250 | UAAAAUGUGAUUUUUGUAU | 499 | AUACAAAAAUCACAUUUUA | 500 | 1479-1497 |
| SNG-251 | AAAAUGUGAUUUUUGUAUA | 501 | UAUACAAAAAUCACAUUUU | 502 | 1480-1498 |
| SNG-252 | AAAUGUGAUUUUUGUAUAU | 503 | AUAUACAAAAAUCACAUUU | 504 | 1481-1499 |
| SNG-253 | AAUGUGAUUUUUGUAUAUA | 505 | UAUAUACAAAAAUCACAUU | 506 | 1482-1500 |
| SNG-254 | AUGUGAUUUUUGUAUAUAC | 507 | GUAUAUACAAAAAUCACAU | 508 | 1483-1501 |
| SNG-255 | GUGUGAUUUUUGUAUAUAA | 509 | UUAUAUACAAAAAUCACAC | 510 | 1483-1501 |
| SNG-256 | UGUGAUUUUUGUAUAUACU | 511 | AGUAUAUACAAAAAUCACA | 512 | 1484-1502 |
| SNG-257 | GUGAUUUUUGUAUAUACUU | 513 | AAGUAUAUACAAAAAUCAC | 514 | 1485-1503 |
| SNG-258 | UGAUUUUUGUAUAUACUUG | 515 | CAAGUAUAUACAAAAAUCA | 516 | 1486-1504 |
| SNG-259 | GGAUUUUUGUAUAUACUUA | 517 | UAAGUAUAUACAAAAAUCC | 518 | 1486-1504 |
| SNG-260 | GAUUUUUGUAUAUACUUGU | 519 | ACAAGUAUAUACAAAAAUC | 520 | 1487-1505 |

TABLE 14

| siRNA | Sense strand (5'→3') | SEQ ID | Antisense strand (5'→3') | SEQ ID | Target site |
|---|---|---|---|---|---|
| SNG-261 | AUUUUUGUAUAUACUUGUA | 521 | UACAAGUAUAUACAAAAAU | 522 | 1488-1506 |
| SNG-262 | UUUUUGUAUAUACUUGUAU | 523 | AUACAAGUAUAUACAAAAA | 524 | 1489-1507 |
| SNG-263 | UUUUGUAUAUACUUGUAUA | 525 | UAUACAAGUAUAUACAAAA | 526 | 1490-1508 |
| SNG-264 | UUUGUAUAUACUUGUAUAU | 527 | AUAUACAAGUAUAUACAAA | 528 | 1491-1509 |
| SNG-265 | UUGUAUAUACUUGUAUAUG | 529 | CAUAUACAAGUAUAUACAA | 530 | 1492-1510 |
| SNG-266 | GUGUAUAUACUUGUAUAUA | 531 | UAUAUACAAGUAUAUACAC | 532 | 1492-1510 |
| SNG-267 | UGUAUAUACUUGUAUAUGU | 533 | ACAUAUACAAGUAUAUACA | 534 | 1493-1511 |
| SNG-268 | GUAUAUACUUGUAUAUGUA | 535 | UACAUAUACAAGUAUAUAC | 536 | 1494-1512 |
| SNG-269 | UAUAUACUUGUAUAUGUAU | 537 | AUACAUAUACAAGUAUAUA | 538 | 1495-1513 |
| SNG-270 | AUAUACUUGUAUAUGUAUG | 539 | CAUACAUAUACAAGUAUAU | 540 | 1496-1514 |
| SNG-271 | GUAUACUUGUAUAUGUAUA | 541 | UAUACAUAUACAAGUAUAC | 542 | 1496-1514 |
| SNG-272 | UAUACUUGUAUAUGUAUGC | 543 | GCAUACAUAUACAAGUAUA | 544 | 1497-1515 |
| SNG-273 | GAUACUUGUAUAUGUAUGA | 545 | UCAUACAUAUACAAGUAUC | 546 | 1497-1515 |
| SNG-274 | AUACUUGUAUAUGUAUGCC | 547 | GGCAUACAUAUACAAGUAU | 548 | 1498-1516 |
| SNG-275 | GUACUUGUAUAUGUAUGCA | 549 | UGCAUACAUAUACAAGUAC | 550 | 1498-1516 |
| SNG-276 | UACUUGUAUAUGUAUGCCA | 551 | UGGCAUACAUAUACAAGUA | 552 | 1499-1517 |
| SNG-277 | ACUUGUAUAUGUAUGCCAA | 553 | UUGGCAUACADAUACAAGU | 554 | 1500-1518 |
| SNG-278 | CUUGUAUAUGUAUGCCAAU | 555 | AUUGGCAUACAUAUACAAG | 556 | 1501-1519 |
| SNG-279 | UUGUAUAUGUAUGCCAAUU | 557 | AAUUGGCAUACAUAUACAA | 558 | 1502-1520 |
| SNG-280 | UGUAUAUGUAUGCCAAUUU | 559 | AAAUUGGCAUACAUAUACA | 560 | 1503-1521 |

TABLE 15

| siRNA | Sense strand (5'→3') | SEQ ID | Antisense strand (5'→3') | SEQ ID | Target site |
|---|---|---|---|---|---|
| SNG-281 | GUAUAUGUAUGCCAAUUUG | 561 | CAAAUUGGCAUACAUAUAC | 562 | 1504-1522 |
| SNG-282 | CUAUAUGUAUGCCAAUUUA | 563 | UAAAUUGGCAUACAUAUAG | 564 | 1504-1522 |
| SNG-283 | UAUAUGUAUGCCAAUUUGG | 565 | CCAAAUUGGCAUACAUAUA | 566 | 1505-1523 |
| SNG-284 | GAUAUGUAUGCCAAUUUGA | 567 | UCAAAUUGGCAVACAUAUC | 568 | 1505-1523 |
| SNG-285 | AUAUGUAUGCCAAUUUGGU | 569 | ACCAAAUUGGCAUACAUAU | 570 | 1506-1524 |
| SNG-286 | UAUGUAUGCCAAUUUGGUG | 571 | CACCAAAUUGGCAUACAUA | 572 | 1507-1525 |
| SNG-287 | GAUGUAUGCCAAUUUGGUA | 573 | UACCAAAUUGGCAUACAUC | 574 | 1507-1525 |
| SNG-288 | AUGUAUGCCAAUUUGGUGC | 575 | GCACCAAAUUGGCAUACAU | 576 | 1508-1526 |
| SNG-289 | GUGUAUGCCAAUUUGGUGA | 577 | UCACCAAAUUGGCAUACAC | 578 | 1508-1526 |
| SNG-290 | UGUAUGCCAAUUUGGUGCU | 579 | AGCACCAAAUUGGCAUACA | 580 | 1509-1527 |
| SNG-291 | GUAUGCCAAUUUGGUGCUU | 581 | AAGCACCAAAUUGGCAUAC | 582 | 1510-1528 |
| SNG-292 | UAUGCCAAUUUGGUGGUUU | 583 | AAAGCACCAAAUUGGCAUA | 584 | 1511-1529 |
| SNG-293 | AUGCCAAUUUGGUGGUUUU | 585 | AAAAGCACCAAAUUGGCAU | 586 | 1512-1530 |
| SNG-294 | UGCCAAUUUGGUGCUUUUU | 587 | AAAAAGCACCAAAUUGGCA | 588 | 1513-1531 |
| SNG-295 | GCCAAUUUGGUGCUUUUUG | 589 | CAAAAAGCACCAAAUUGGC | 590 | 1514-1532 |
| SNG-296 | CCCAAUUUGGUGCUUUUA | 591 | UAAAAAGCACCAAAUUGGG | 592 | 1514-1532 |
| SNG-297 | CCAAUUUGGUGCUUUUUGU | 593 | ACAAAAAGCACCAAAUUGG | 594 | 1515-1533 |
| SNG-298 | CAAUUUGGUGCUUUUUGUA | 595 | UACAAAAAGCACCAAAUUG | 596 | 1516-1534 |
| SNG-299 | AAUUUGGUGCUUUUUGUAA | 597 | UUACAAAAAGCACCAAAUU | 598 | 1517-1535 |
| SNG-300 | AGUUUGUGUUAUAUGUUGU | 599 | ACAACAUAUAACACAAACU | 600 | 1715-1733 |

TABLE 16

| siRNA | Sense strand (5'→3') | SEQ ID | Antisense strand (5'→3') | SEQ ID | Target site |
|---|---|---|---|---|---|
| SNG-301 | GUUUGUGUUAUAUGUUGUU | 601 | AACAACAUAUAACACAAAC | 602 | 1716-1734 |
| SNG-302 | UUUGUGUUAUAUGUUGUUU | 603 | AAACAACAUAUAACACAAA | 604 | 1717-1735 |
| SNG-303 | UUGUGUUAUAUGUUGUUUU | 605 | AAAACAACAUAUAACACAA | 606 | 1718-1736 |
| SNG-304 | UGUGUUAUAUGUUGUUUUA | 607 | UAAAACAACAUAUAACACA | 608 | 1719-1737 |
| SNG-305 | CUAUCUGCCUGGAGAUGUA | 624 | AACAUCUCCAGGCAGAUAG | 26 | 211-229 |
| SNG-306 | GUGCCUGGAGAUGUUUACU | 625 | UGUAAACAUCUCCAGGCAC | 38 | 215-233 |
| SNG-307 | GCCUGGAGAUGUUUACCAU | 626 | UUGGUAAACAUCUCCAGGC | 42 | 217-235 |
| SNG-308 | GGCUCAGUGUCCAUGUCUU | 627 | UAGACAUGGACACUGAGCC | 76 | 330-348 |
| SNG-309 | GAUCAACAUCUACUGUCUU | 628 | UAGACAGUAGAUGUUGAUC | 194 | 527-545 |
| SNG-310 | CAUCUACUGUCUCACGUGA | 629 | ACACGUGAGACAGUAGAUG | 212 | 533-551 |
| SNG-311 | UCUACUGUCUCACGUGUGU | 630 | UCACACGUGAGACAGUAGA | 218 | 535-553 |
| SNG-312 | GUACUGUCUCACGUGUGAU | 631 | UUCACACGUGAGACAGUAC | 222 | 536-554 |
| SNG-313 | GCUCCAUGCUGGUGGCGGU | 632 | UCCGCCACCAGCAUGGAGC | 266 | 661-679 |
| SNG-314 | GGCUUUGAGAACAUGGACA | 633 | AGUCCAUGUUCUCAAAGCC | 388 | 1041-1059 |
| SNG-315 | GCUUUGAGAACAUGGACUA | 634 | AAGUCCAUGUUCUCAAAGC | 390 | 1042-1060 |

TABLE 16-continued

| siRNA | Sense strand (5'→3') | SEQ ID | Antisense strand (5'→3') | SEQ ID | Target site |
|---|---|---|---|---|---|
| SNG-316 | CCAUUGACUUUGGGACAGU | 635 | UCUGUCCCAAAGUCAAUGG | 402 | 1102-1120 |
| SNG-317 | GCACAGGACACUUUUCUAU | 636 | UUAGAAAAGUGUCCUGUGC | 482 | 1428-1446 |
| SNG-318 | CACAGGACACUUUUCUACU | 637 | UGUAGAAAAGUGUCCUGUG | 484 | 1429-1447 |
| SNG-319 | CUUGUAUAUGUAUGCCAAA | 638 | AUUGGCAUACAUAUACAAG | 556 | 1501-1519 |
| SNG-320 | GUGUAUGCCAAUUUGGUGU | 639 | UCACCAAAUUGGCAUACAC | 578 | 1508-1526 |

Example 2: In Vitro Model Mouse Cell Culture

Mouse melanoma B16 cells were cultured in MEM (Thermo Fisher Scientific)+10% Fetal bovine serum (FBS) (HyClone)+Penicillin (100 units/mL) (Thermo Fisher Scientific)+Streptomycin (100 ug/mL) (Thermo Fisher Scientific) and maintained at 37° C., 95 to 98% humidity and 5% $CO_2$.

Example 3: Evaluation of siRNA Against Murf1

The siRNA double strands with dTdT as overhangs added to the 3'end of the antisense strand and the sense strand of the siRNAs designed in Example 1 were purchased from SIGMA. With the purchased siRNA double strands, knockdown experiments were conducted in mouse B16 cells cultured under the conditions of Example 2. The siRNA double strands were introduced into cells with Lipofectamine (Registered Trademark) 3000 (Thermo Fisher Scientific) and the cells were added to cell culture solutions so that the final concentration of the siRNA double strands became 10 nmol/L. The cells were collected using CellAmp (Trademark) Direct RNA Prep Kit for RT-PCR (Takara Bio Inc.) 24 hours after introduction, and real-time PCR was conducted. Gapdh was used as an endogenous control.

The primer sequences for measuring the level of mouse Murf1 expression were

```
Fw primer: (SEQ ID NO: 613);
TGTCTCACGTGTGAGGTGCCTA

Rv primer: (SEQ ID NO: 614);
CACCAGCATGGAGATGCAGTTAC,
``` and the primer sequences for measuring the level of mouse Gapdh expression were

```
Fw primer: (SEQ ID NO: 615);
TGTGTCCGTCGTGGATCTGA

Rv primer: (SEQ ID NO: 616);
TTGCTGTTGAAGTCGCAGGAG.
```

The results of knockdown activity are shown in Table 17.

TABLE 17

| siRNA | ΔΔCt |
|---|---|
| SNG-11 | −0.60 |
| SNG-12 | −1.01 |
| SNG-13 | −0.55 |
| SNG-17 | −0.95 |

TABLE 17-continued

| siRNA | ΔΔCt |
|---|---|
| SNG-19 | −1.03 |
| SNG-21 | −0.62 |
| SNG-25 | −0.85 |
| SNG-28 | −0.65 |
| SNG-30 | −0.59 |
| SNG-38 | −1.02 |
| SNG-40 | −0.80 |
| SNG-52 | −0.65 |
| SNG-53 | −0.50 |
| SNG-73 | −0.98 |
| SNG-79 | −0.70 |
| SNG-88 | −0.76 |
| SNG-97 | −1.00 |
| SNG-105 | −0.24 |
| SNG-106 | −0.30 |
| SNG-108 | −0.80 |
| SNG-109 | −0.65 |
| SNG-111 | −0.41 |
| SNG-113 | −0.14 |
| SNG-116 | −0.80 |
| SNG-118 | −0.76 |
| SNG-122 | −0.10 |
| SNG-127 | −0.52 |
| SNG-133 | −0.38 |
| SNG-141 | −0.36 |
| SNG-151 | −1.08 |
| SNG-157 | −0.67 |
| SNG-168 | −1.10 |
| SNG-180 | −0.70 |
| SNG-182 | −0.37 |
| SNG-191 | −0.52 |
| SNG-192 | −0.81 |
| SNG-193 | −0.59 |
| SNG-194 | −0.47 |
| SNG-195 | −0.32 |
| SNG-197 | −1.10 |
| SNG-201 | −1.03 |
| SNG-232 | −0.97 |
| SNG-236 | −0.58 |
| SNG-238 | −0.58 |
| SNG-241 | −0.74 |
| SNG-242 | −0.98 |
| SNG-252 | −0.65 |
| SNG-255 | −0.65 |
| SNG-257 | −1.03 |
| SNG-268 | −0.17 |
| SNG-278 | −0.59 |
| SNG-281 | −0.88 |
| SNG-282 | −0.66 |
| SNG-284 | −0.65 |
| SNG-287 | −0.55 |
| SNG-289 | −0.74 |
| SNG-292 | −0.93 |
| SNG-293 | 0.07 |
| SNG-294 | −1.02 |
| SNG-297 | −0.96 |
| SNG-298 | −0.76 |

TABLE 17-continued

| siRNA | ΔΔCt |
|---|---|
| SNG-303 | −0.83 |
| SNG-304 | −1.03 |

For the knockdown activity, the difference (ΔCt) between the expression level (Ct value) of mouse Murf1 and the expression level (Ct value) of mouse Gapdh in the cells into which each siRNA double strand was introduced, was relatively compared with the activity of SNG-305 shown in Table 18 (ΔΔCt).

$$\Delta\Delta Ct = \text{(expression level of Gapdh-expression level of SNG-305)}(\Delta Ct)\text{-(expression level of Gapdh-expression level of each siRNA duplex)}(\Delta Ct)$$

The knockdown activity of SNG-305 is defined as ΔΔCt=0, siRNA showing higher activity than the knockdown activity of SNG-305 shows a positive value, and siRNA showing lower activity shows a negative value. In the base sequence of Table 18, capital letters mean RNA and small letters mean DNA.

TABLE 18

| siRNA | Strand | 5'→3' | SEQ ID |
|---|---|---|---|
| SNG-305 | Sense | GUUGGUGCSAAAUGAAAUAtt | 617 |
| | Antisense | UAUUUCAUUUCGCACCAACtt | 618 |

SNG-305 is the siRNA double strand designed for mouse Murf1 mRNA and is not homologous to human MURF1. It was added to mouse B16 cells using Lipofectamine 3000 so that the final concentration of siRNA double strand was 10 nmol/L and it showed a strong knockdown activity of 89% 24 hours after introduction. Therefore, it was used as a positive control. As a result, it was found that the siRNA of this application suppresses the expression of mouse Murf1 because it shows a strong knockdown activity almost equivalent to that of SNG-305. Furthermore, since the siRNA of this application has homology with human MURF1, it was suggested that it suppresses the expression of human MURF1.

Example 4: In Vitro Model Human Cell Culture

Human skeletal myoblasts were cultured in SkGM-2 BulletKit (Lonza). Then they were cultured in DMEM (Thermo Fisher Scientific)+2% horse serum (Thermo Fisher Scientific)+Penicillin (100 units/mL) (Thermo Fisher Scientific)+streptomycin (100 ug/mL) (Thermo Fisher Scientific) and maintained at 37° C., 95-98% humidity and 5% $CO_2$. The culture vessel was used after coating with Matrigel (Corning).

Example 5: Evaluation of siRNA Against MURF1

The siRNA double strands with dTdT overhangs added to 3'end of the antisense strand and the sense strand of some of the siRNAs designed in Example 1 were purchased from SIGMA. With the purchased siRNA double strands, knockdown experiments were conducted in human skeletal myoblasts cultured under the conditions of Example 4. siRNA double strands were transfected into cells with Lipofectamine (Registered Trademark) 3000 (Thermo Fisher Scientific) and the cells were added to cell culture solutions so that the final concentration of the siRNA double strands became 20 nmol/L. The cells were collected using CellAmp (Trademark) Direct RNA Prep Kit for RT-PCR (Takara Bio Inc.) 24 hours after introduction, and real-time PCR was conducted. GAPDH was used as an endogenous control.

The primer sequences for measuring the level of human MURF1 expression were

Fw primer: (SEQ ID NO: 640);
CGTGTGCAGACCATCATCACTC

Rv primer: (SEQ ID NO: 641);
CAACGTGTCAAACTTCTGGCTC and the primer sequences for measuring the level of human GAPDH expression were Fw primer: (SEQ ID NO: 642);
GCACCGTCAAGGCTGAGAAC Rv primer: (SEQ ID NO: 643);
TGGTGAAGACGCCAGTGGA.

The results of the mRNA residual rate are shown in Table 19.

TABLE 19

| siRNA | mRNA residual rate |
|---|---|
| SNG-13 | 16% |
| SNG-19 | 23% |
| SNG-21 | 15% |
| SNG-38 | 16% |
| SNG-97 | 20% |
| SNG-106 | 15% |
| SNG-109 | 9% |
| SNG-111 | 10% |
| SNG-133 | 13% |
| SNG-194 | 10% |
| SNG-195 | 9% |
| SNG-241 | 11% |
| SNG-242 | 12% |
| SNG-278 | 11% |
| SNG-289 | 10% |
| SNG-305 | 15% |
| SNG-306 | 18% |
| SNG-307 | 13% |
| SNG-308 | 15% |
| SNG-309 | 23% |
| SNG-310 | 11% |
| SNG-311 | 8% |
| SNG-312 | 14% |
| SNG-313 | 18% |
| SNG-314 | 13% |
| SNG-315 | 12% |
| SNG-316 | 13% |
| SNG-317 | 15% |
| SNG-318 | 15% |
| SNG-319 | 9% |
| SNG-320 | 11% |

The mRNA residual rate was calculated by the following method. All treatment groups were performed at N=3.

First, the difference between the expression level of human MURF1 (Ct value) and the expression level (Ct value) of human GAPDH in cells of the Non-treated (NT) group was calculated (ΔCt). After that, the average value of each ΔCt was calculated as $\Delta Ct_{(NT\_ave.)}$. Subsequently, the difference between the expression level (Ct value) of human MURF1 and the expression level (Ct value) of human GAPDH in the cells into which each siRNA double strand was introduced was calculated ($\Delta Ct_{(siRNA)}$). Then, after calculating the difference (ΔΔCt) between each $\Delta Ct_{(siRNA)}$ and $\Delta Ct_{(NT\_ave.)}$, the mRNA residual rate was calculated for each by the following formula.

$$\text{mRNA residual rate}=2^{\Delta\Delta Ct}\times 100(\%),$$
$$\Delta\Delta Ct=\Delta Ct_{(siRNA)}-\Delta Ct_{(NT\_ave.)}$$

Finally, the average value of the mRNA residual rate in each treatment group was calculated.

As a result, it was found that the siRNAs of this application have low mRNA residual rate and strongly suppress the expression of human MURF1.

INDUSTRIAL APPLICABILITY

Nucleic acids of this invention show suppression activities of MURF1 expression. Therefore, the compounds of this invention are very useful as medicine for disease accompanied by one or more symptoms selected from the group consisting of decrease in muscle mass, decrease in muscle strength and muscle dysfunction.

---

The invention claimed is:

1. A nucleic acid suppressing the expression of MURF1 comprising an oligonucleotide consisting of 15 to 30 nucleotides having at least 15 bases or more complementary to the base sequence consisting of positions 1427 to 1447 of SEQ ID NO: 609.

2. The nucleic acid according to claim 1 comprising the base sequence of at least 15 consecutive bases in the base sequence of SEQ ID NO: 621.

3. A nucleic acid comprising the base sequence of SEQ ID NO: 482 or 484;

the base sequence of SEQ ID NO: 482 wherein 1 to 3 bases are deleted, substituted or inserted at positions 2 to 18; or the base sequence of SEQ ID NO: 484 wherein 1 to 3 bases are deleted, substituted or inserted;

and suppressing the expression of MURF1.

4. A double-stranded nucleic acid comprising any of the following combinations:

an oligonucleotide consisting of the base sequence of SEQ ID NO: 481 or 636 and an oligonucleotide consisting of the base sequence of SEQ ID NO: 482, or an oligonucleotide consisting of the base sequence of SEQ ID NO: 483 or 637 and an oligonucleotide consisting of the base sequence of SEQ ID NO: 484.

5. The nucleic acid according to claim 4 suppressing the expression of MURF1.

6. The nucleic acid according to claim 1, which is siRNA, antisense oligonucleotide, shRNA or miRNA.

7. The nucleic acid according to claim 6, which is siRNA having an overhangs at the 3' end of the sense and/or the antisense strand.

8. The nucleic acid according to claim 3, which is siRNA, antisense oligonucleotide, shRNA or miRNA.

9. The nucleic acid according to claim 8, which is siRNA having an overhang at the 3' end of the sense and/or the antisense strand.

10. The nucleic acid according to claim 4, which is siRNA, antisense oligonucleotide or miRNA.

11. The nucleic acid according to claim 10, which is siRNA having an overhangs at the 3' end of the sense and/or the antisense strand.

* * * * *

SEQUENCE LISTING

<160> NUMBER OF SEQ ID NOS: 643

<210> SEQ ID NO 1
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 1
cuuggagaag cagcugauc                                          19

<210> SEQ ID NO 2
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 2
gaucagcugc uucuccaag                                          19

<210> SEQ ID NO 3
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 3
guuggagaag cagcugaua                                          19

<210> SEQ ID NO 4
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 4
uaucagcugc uucuccaac                                          19

<210> SEQ ID NO 5
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 5
uuggagaagc agcugaucu                                          19

<210> SEQ ID NO 6
<211> LENGTH: 19

-continued

```
<212> TYPE: RNA
<213> ORGANISM: Artificial sequence
<220> FEATURE:
<223> OTHER INFORMATION: Antisense strand of siRNA

<400> SEQUENCE: 6
agaucagcug cuucuccaa                                              19

<210> SEQ ID NO 7
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 7
uggagaagca gcugaucug                                              19

<210> SEQ ID NO 8
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 8
cagaucagcu gcuucucca                                              19

<210> SEQ ID NO 9
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 9
gggagaagca gcugaucua                                              19

<210> SEQ ID NO 10
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 10
uagaucagcu gcuucuccc                                              19

<210> SEQ ID NO 11
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 11
ggagaagcag cugaucugc                                              19

<210> SEQ ID NO 12
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 12
```

-continued

```
gcagaucagc ugcuucucc                                              19

<210> SEQ ID NO 13
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 13
cgagaagcag cugaucuga                                              19

<210> SEQ ID NO 14
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 14
ucagaucagc ugcuucucg                                              19

<210> SEQ ID NO 15
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 15
gagaagcagc ugaucugcc                                              19

<210> SEQ ID NO 16
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 16
ggcagaucag cugcuucuc                                              19

<210> SEQ ID NO 17
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 17
cagaagcagc ugaucugca                                              19

<210> SEQ ID NO 18
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 18
ugcagaucag cugcuucug                                              19

<210> SEQ ID NO 19
<211> LENGTH: 19
<212> TYPE: RNA
<213> ORGANISM: Artificial sequence
```

-continued

<220> FEATURE:
<223> OTHER INFORMATION: Sense strand of siRNA

<400> SEQUENCE: 19
agaagcagcu gaucugccc                                                          19

<210> SEQ ID NO 20
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 20
gggcagauca gcugcuucu                                                          19

<210> SEQ ID NO 21
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 21
ggaagcagcu gaucugcca                                                          19

<210> SEQ ID NO 22
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 22
uggcagauca gcugcuucc                                                          19

<210> SEQ ID NO 23
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 23
gaagcagcug aucugcccu                                                          19

<210> SEQ ID NO 24
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 24
agggcagauc agcugcuuc                                                          19

<210> SEQ ID NO 25
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 25
cuaucugccu ggagauguu                                                          19

-continued

```
<210> SEQ ID NO 26
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 26
aacaucucca ggcagauag                                                19

<210> SEQ ID NO 27
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 27
uaucugccug gagauguuu                                                19

<210> SEQ ID NO 28
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 28
aaacaucucc aggcagaua                                                19

<210> SEQ ID NO 29
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 29
aucugccugg agauguuua                                                19

<210> SEQ ID NO 30
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 30
uaaacaucuc caggcagau                                                19

<210> SEQ ID NO 31
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 31
ucugccugga gauguuuac                                                19

<210> SEQ ID NO 32
<211> LENGTH: 19
<212> TYPE: RNA
<213> ORGANISM: Artificial sequence
<220> FEATURE:
<223> OTHER INFORMATION: Antisense strand of siRNA
```

-continued

<400> SEQUENCE: 32
guaaacaucu ccaggcaga                                                                 19

<210> SEQ ID NO 33
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 33
gcugccugga gauguuuaa                                                                 19

<210> SEQ ID NO 34
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 34
uuaaacaucu ccaggcagc                                                                 19

<210> SEQ ID NO 35
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 35
cugccuggag auguuuacc                                                                 19

<210> SEQ ID NO 36
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 36
gguaaacauc uccaggcag                                                                 19

<210> SEQ ID NO 37
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 37
gugccuggag auguuuaca                                                                 19

<210> SEQ ID NO 38
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 38
uguaaacauc uccaggcac                                                                 19

<210> SEQ ID NO 39

-continued

```
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 39
ugccuggaga uguuuacca                                              19

<210> SEQ ID NO 40
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 40
ugguaaacau cuccaggca                                              19

<210> SEQ ID NO 41
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 41
gccuggagau guuuaccaa                                              19

<210> SEQ ID NO 42
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 42
uugguaaaca ucuccaggc                                              19

<210> SEQ ID NO 43
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 43
ccuggagaug uuuaccaag                                              19

<210> SEQ ID NO 44
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 44
cuugguaaac aucuccagg                                              19

<210> SEQ ID NO 45
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 45
```

-continued

```
gcuggagaug uuuaccaaa                                      19

<210> SEQ ID NO 46
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 46
uuugguaaac aucuccagc                                      19

<210> SEQ ID NO 47
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 47
cuggagaugu uuaccaagc                                      19

<210> SEQ ID NO 48
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 48
gcuugguaaa caucuccag                                      19

<210> SEQ ID NO 49
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 49
guggagaugu uuaccaaga                                      19

<210> SEQ ID NO 50
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 50
ucuugguaaa caucuccac                                      19

<210> SEQ ID NO 51
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 51
uggagauguu uaccaagcc                                      19

<210> SEQ ID NO 52
<211> LENGTH: 19
<212> TYPE: RNA
```

```
<213> ORGANISM: Artificial sequence
<220> FEATURE:
<223> OTHER INFORMATION: Antisense strand of siRNA

<400> SEQUENCE: 52
ggcuugguaa acaucucca                                                  19

<210> SEQ ID NO 53
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 53
gggagauguu uaccaagca                                                  19

<210> SEQ ID NO 54
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 54
ugcuugguaa acaucuccc                                                  19

<210> SEQ ID NO 55
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 55
ggagauguuu accaagcca                                                  19

<210> SEQ ID NO 56
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 56
uggcuuggua aacaucucc                                                  19

<210> SEQ ID NO 57
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 57
ugugccggaa gugugccaa                                                  19

<210> SEQ ID NO 58
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 58
uuggcacacu uccggcaca                                                  19
```

-continued

```
<210> SEQ ID NO 59
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 59
gugccggaag ugugccaau                                              19

<210> SEQ ID NO 60
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 60
auuggcacac uuccggcac                                              19

<210> SEQ ID NO 61
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 61
augacaucuu ccaggcugc                                              19

<210> SEQ ID NO 62
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 62
gcagccugga agaugucau                                              19

<210> SEQ ID NO 63
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 63
gugacaucuu ccaggcuga                                              19

<210> SEQ ID NO 64
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 64
ucagccugga agaugucac                                              19

<210> SEQ ID NO 65
<211> LENGTH: 19
<212> TYPE: RNA
<213> ORGANISM: Artificial sequence
<220> FEATURE:
```

<223> OTHER INFORMATION: Sense strand of siRNA

<400> SEQUENCE: 65
ugacaucuuc caggcugca                           19

<210> SEQ ID NO 66
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 66
ugcagccugg aagauguca                           19

<210> SEQ ID NO 67
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 67
caaaucccua cuggaccag                           19

<210> SEQ ID NO 68
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 68
cugguccagu agggauuug                           19

<210> SEQ ID NO 69
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 69
gaaaucccua cuggaccaa                           19

<210> SEQ ID NO 70
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 70
uugguccagu agggauuuc                           19

<210> SEQ ID NO 71
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 71
cagcucagug uccaugucu                           19

<210> SEQ ID NO 72
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 72
agacauggac acugagcug                                                          19

<210> SEQ ID NO 73
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 73
agcucagugu ccaugucug                                                          19

<210> SEQ ID NO 74
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 74
cagacaugga cacugagcu                                                          19

<210> SEQ ID NO 75
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 75
ggcucagugu ccaugucua                                                          19

<210> SEQ ID NO 76
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 76
uagacaugga cacugagcc                                                          19

<210> SEQ ID NO 77
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 77
gcucaguguc caugucugg                                                          19

<210> SEQ ID NO 78
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 78
ccagacaugg acacugagc                                                  19

<210> SEQ ID NO 79
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 79
ccucaguguc caugucuga                                                  19

<210> SEQ ID NO 80
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 80
ucagacaugg acacugagg                                                  19

<210> SEQ ID NO 81
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 81
cucagugucc augucugga                                                  19

<210> SEQ ID NO 82
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 82
uccagacaug gacacugag                                                  19

<210> SEQ ID NO 83
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 83
ucagugucca ugucuggag                                                  19

<210> SEQ ID NO 84
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 84
cuccagacau ggacacuga                                                  19

<210> SEQ ID NO 85
<211> LENGTH: 19

-continued

```
<212> TYPE: RNA
<213> ORGANISM: Artificial sequence
<220> FEATURE:
<223> OTHER INFORMATION: Sense strand of siRNA

<400> SEQUENCE: 85
gcagugucca ugucuggaa                                                  19

<210> SEQ ID NO 86
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 86
uuccagacau ggacacugc                                                  19

<210> SEQ ID NO 87
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 87
caguguccau gucuggagg                                                  19

<210> SEQ ID NO 88
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 88
ccuccagaca uggacacug                                                  19

<210> SEQ ID NO 89
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 89
gaguguccau gucuggaga                                                  19

<210> SEQ ID NO 90
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 90
ucuccagaca uggacacuc                                                  19

<210> SEQ ID NO 91
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 91
```

-continued aguguccaug ucuggaggc                                                    19

<210> SEQ ID NO 92
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 92
gccuccagac auggacacu                                                    19

<210> SEQ ID NO 93
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 93
gguguccaug ucuggagga                                                    19

<210> SEQ ID NO 94
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 94
uccuccagac auggacacc                                                    19

<210> SEQ ID NO 95
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 95
gaguguacgg ccugcagag                                                    19

<210> SEQ ID NO 96
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 96
cucugcaggc cguacacuc                                                    19

<210> SEQ ID NO 97
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 97
caguguacgg ccugcagaa                                                    19

<210> SEQ ID NO 98
<211> LENGTH: 19
<212> TYPE: RNA
<213> ORGANISM: Artificial sequence -continued

```
<220> FEATURE:
<223> OTHER INFORMATION: Antisense strand of siRNA

<400> SEQUENCE: 98
uucugcaggc cguacacug                                              19

<210> SEQ ID NO 99
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 99
aguguacggc cugcagagg                                              19

<210> SEQ ID NO 100
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 100
ccucugcagg ccguacacu                                              19

<210> SEQ ID NO 101
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 101
gguguacggc cugcagaga                                              19

<210> SEQ ID NO 102
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 102
ucucugcagg ccguacacc                                              19

<210> SEQ ID NO 103
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 103
guguacggcc ugcagagga                                              19

<210> SEQ ID NO 104
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 104
uccucugcag gccguacac                                              19
```

-continued

```
<210> SEQ ID NO 105
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 105
uguacggccu gcagaggaa                                                    19

<210> SEQ ID NO 106
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 106
uuccucugca ggccguaca                                                    19

<210> SEQ ID NO 107
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 107
guacggccug cagaggaac                                                    19

<210> SEQ ID NO 108
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 108
guuccucugc aggccguac                                                    19

<210> SEQ ID NO 109
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 109
cuacggccug cagaggaaa                                                    19

<210> SEQ ID NO 110
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 110
uuuccucugc aggccguag                                                    19

<210> SEQ ID NO 111
<211> LENGTH: 19
<212> TYPE: RNA
<213> ORGANISM: Artificial sequence
<220> FEATURE:
<223> OTHER INFORMATION: Sense strand of siRNA
```

<400> SEQUENCE: 111
uacggccugc agaggaacc                                                       19

<210> SEQ ID NO 112
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 112
gguuccucug caggccgua                                                       19

<210> SEQ ID NO 113
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 113
gacggccugc agaggaaca                                                       19

<210> SEQ ID NO 114
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 114
uguuccucug caggccguc                                                       19

<210> SEQ ID NO 115
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 115
acggccugca gaggaaccu                                                       19

<210> SEQ ID NO 116
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 116
agguuccucu gcaggccgu                                                       19

<210> SEQ ID NO 117
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 117
cggccugcag aggaaccug                                                       19

<210> SEQ ID NO 118

-continued

```
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 118
cagguuccuc ugcaggccg                                                    19

<210> SEQ ID NO 119
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 119
gggccugcag aggaaccua                                                    19

<210> SEQ ID NO 120
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 120
uagguuccuc ugcaggccc                                                    19

<210> SEQ ID NO 121
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 121
ggccugcaga ggaaccugc                                                    19

<210> SEQ ID NO 122
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 122
gcagguuccu cugcaggcc                                                    19

<210> SEQ ID NO 123
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 123
cgccugcaga ggaaccuga                                                    19

<210> SEQ ID NO 124
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 124
```

-continued

```
ucagguuccu cugcaggcg                                                 19

<210> SEQ ID NO 125
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 125
gccugcagag gaaccugcu                                                 19

<210> SEQ ID NO 126
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 126
agcagguucc ucugcaggc                                                 19

<210> SEQ ID NO 127
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 127
ccugcagagg aaccugcug                                                 19

<210> SEQ ID NO 128
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 128
cagcagguuc cucugcagg                                                 19

<210> SEQ ID NO 129
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 129
gcugcagagg aaccugcua                                                 19

<210> SEQ ID NO 130
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 130
uagcagguuc cucugcagc                                                 19

<210> SEQ ID NO 131
<211> LENGTH: 19
<212> TYPE: RNA
```

-continued

```
<213> ORGANISM: Artificial sequence
<220> FEATURE:
<223> OTHER INFORMATION: Sense strand of siRNA

<400> SEQUENCE: 131
cugcagagga accugcugg                                                      19

<210> SEQ ID NO 132
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 132
ccagcagguu ccucugcag                                                      19

<210> SEQ ID NO 133
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 133
gugcagagga accugcuga                                                      19

<210> SEQ ID NO 134
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 134
ucagcagguu ccucugcac                                                      19

<210> SEQ ID NO 135
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 135
ugcagaggaa ccugcuggu                                                      19

<210> SEQ ID NO 136
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 136
accagcaggu uccucugca                                                      19

<210> SEQ ID NO 137
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 137
gcagaggaac cugcuggug                                                      19
```

<210> SEQ ID NO 138
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 138
caccagcagg uuccucugc                                                              19

<210> SEQ ID NO 139
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 139
ccagaggaac cugcuggua                                                              19

<210> SEQ ID NO 140
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 140
uaccagcagg uuccucugg                                                              19

<210> SEQ ID NO 141
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 141
cagaggaacc ugcuggugg                                                              19

<210> SEQ ID NO 142
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 142
ccaccagcag guuccucug                                                              19

<210> SEQ ID NO 143
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 143
gagaggaacc ugcugguga                                                              19

<210> SEQ ID NO 144
<211> LENGTH: 19
<212> TYPE: RNA
<213> ORGANISM: Artificial sequence
<220> FEATURE:

-continued

---

<223> OTHER INFORMATION: Antisense strand of siRNA

<400> SEQUENCE: 144
ucaccagcag guuccucuc                                                    19

<210> SEQ ID NO 145
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 145
agaggaaccu gcuggugga                                                    19

<210> SEQ ID NO 146
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 146
uccaccagca gguuccucu                                                    19

<210> SEQ ID NO 147
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 147
gaggaaccug cugguggag                                                    19

<210> SEQ ID NO 148
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 148
cuccaccagc agguuccuc                                                    19

<210> SEQ ID NO 149
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 149
caggaaccug cugguggaa                                                    19

<210> SEQ ID NO 150
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 150
uuccaccagc agguuccug                                                    19

-continued

```
<210> SEQ ID NO 151
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 151
aacaggagug cuccagucg                                                          19

<210> SEQ ID NO 152
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 152
cgacuggagc acuccuguu                                                          19

<210> SEQ ID NO 153
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 153
gacaggagug cuccaguca                                                          19

<210> SEQ ID NO 154
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 154
ugacuggagc acuccuguc                                                          19

<210> SEQ ID NO 155
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 155
acaggagugc uccagucgg                                                          19

<210> SEQ ID NO 156
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 156
ccgacuggag cacuccugu                                                          19

<210> SEQ ID NO 157
<211> LENGTH: 19
<212> TYPE: RNA
<213> ORGANISM: Artificial sequence
<220> FEATURE:
<223> OTHER INFORMATION: Sense strand of siRNA
```

<400> SEQUENCE: 157
gcaggagugc uccagucga                                                     19

<210> SEQ ID NO 158
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 158
ucgacuggag cacuccugc                                                     19

<210> SEQ ID NO 159
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 159
caggagugcu ccagucggc                                                     19

<210> SEQ ID NO 160
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 160
gccgacugga gcacccug                                                      19

<210> SEQ ID NO 161
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 161
gaggagugcu ccagucgga                                                     19

<210> SEQ ID NO 162
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 162
uccgacugga gcacccuc                                                      19

<210> SEQ ID NO 163
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 163
aggagugcuc cagucggcc                                                     19

<210> SEQ ID NO 164
<211> LENGTH: 19

```
<212> TYPE: RNA
<213> ORGANISM: Artificial sequence
<220> FEATURE:
<223> OTHER INFORMATION: Antisense strand of siRNA

<400> SEQUENCE: 164
ggccgacugg agcacuccu                                            19

<210> SEQ ID NO 165
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 165
gggagugcuc cagucggca                                            19

<210> SEQ ID NO 166
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 166
ugccgacugg agcacuccc                                            19

<210> SEQ ID NO 167
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 167
ggagugcucc agucggccg                                            19

<210> SEQ ID NO 168
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 168
cggccgacug gagcacucc                                            19

<210> SEQ ID NO 169
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 169
cgagugcucc agucggcca                                            19

<210> SEQ ID NO 170
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 170
```

-continued

```
uggccgacug gagcacucg                                    19

<210> SEQ ID NO 171
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 171
augagaaaau caacaucua                                    19

<210> SEQ ID NO 172
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 172
uagauguuga uuuucucau                                    19

<210> SEQ ID NO 173
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 173
ugagaaaauc aacaucuac                                    19

<210> SEQ ID NO 174
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 174
guagauguug auuuucuca                                    19

<210> SEQ ID NO 175
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 175
ggagaaaauc aacaucuaa                                    19

<210> SEQ ID NO 176
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 176
uuagauguug auuuucucc                                    19

<210> SEQ ID NO 177
<211> LENGTH: 19
<212> TYPE: RNA
<213> ORGANISM: Artificial sequence
```

-continued

<220> FEATURE:
<223> OTHER INFORMATION: Sense strand of siRNA

<400> SEQUENCE: 177
gagaaaauca acaucuacu                                                                          19

<210> SEQ ID NO 178
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 178
aguagauguu gauuuucuc                                                                          19

<210> SEQ ID NO 179
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 179
agaaaaucaa caucuacug                                                                          19

<210> SEQ ID NO 180
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 180
caguagaugu ugauuuucu                                                                          19

<210> SEQ ID NO 181
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 181
ggaaaaucaa caucuacua                                                                          19

<210> SEQ ID NO 182
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 182
uaguagaugu ugauuuucc                                                                          19

<210> SEQ ID NO 183
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 183 gaaaucaac aucuacugu                                                                           19

-continued

```
<210> SEQ ID NO 184
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 184
acaguagaug uugauuuuc                                                      19

<210> SEQ ID NO 185
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 185
aaaaucaaca ucuacuguc                                                     19

<210> SEQ ID NO 186
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 186
gacaguagau guugauuuu                                                     19

<210> SEQ ID NO 187
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 187
gaaaucaaca ucuacugua                                                     19

<210> SEQ ID NO 188
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 188
uacaguagau guugauuuc                                                     19

<210> SEQ ID NO 189
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 189
aaaucaacau cuacugucu                                                     19

<210> SEQ ID NO 190
<211> LENGTH: 19
<212> TYPE: RNA
<213> ORGANISM: Artificial sequence
<220> FEATURE:
<223> OTHER INFORMATION: Antisense strand of siRNA
```

-continued

```
<400> SEQUENCE: 190
agacaguaga uguugauuu                                              19

<210> SEQ ID NO 191
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 191
aaucaacauc uacugucuc                                              19

<210> SEQ ID NO 192
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 192
gagacaguag auguugauu                                              19

<210> SEQ ID NO 193
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 193
gaucaacauc uacugucua                                              19

<210> SEQ ID NO 194
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 194
uagacaguag auguugauc                                              19

<210> SEQ ID NO 195
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 195
aucaacaucu acugucuca                                              19

<210> SEQ ID NO 196
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 196
ugagacagua gauguugau                                              19

<210> SEQ ID NO 197
```

```
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 197
ucaacaucua cugucucac                                                    19

<210> SEQ ID NO 198
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 198
gugagacagu agauguuga                                                    19

<210> SEQ ID NO 199
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 199
gcaacaucua cugucucaa                                                    19

<210> SEQ ID NO 200
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 200
uugagacagu agauguugc                                                    19

<210> SEQ ID NO 201
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 201
caacaucuac ugucucacg                                                    19

<210> SEQ ID NO 202
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 202
cgugagacag uagauguug                                                    19

<210> SEQ ID NO 203
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 203
```

```
gaacaucuac ugucucaca                                                 19

<210> SEQ ID NO 204
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 204
ugugagacag uagauguuc                                                 19

<210> SEQ ID NO 205
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 205
aacaucuacu gucucacgu                                                 19

<210> SEQ ID NO 206
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 206
acgugagaca guagauguu                                                 19

<210> SEQ ID NO 207
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 207
acaucuacug ucucacgug                                                 19

<210> SEQ ID NO 208
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 208
cacgugagac aguagaugu                                                 19

<210> SEQ ID NO 209
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 209
gcaucuacug ucucacgua                                                 19

<210> SEQ ID NO 210
<211> LENGTH: 19
<212> TYPE: RNA
```

-continued

```
<213> ORGANISM: Artificial sequence
<220> FEATURE:
<223> OTHER INFORMATION: Antisense strand of siRNA

<400> SEQUENCE: 210
uacgugagac aguagaugc                                           19

<210> SEQ ID NO 211
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 211
caucuacugu cucacgugu                                           19

<210> SEQ ID NO 212
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 212
acacgugaga caguagaug                                           19

<210> SEQ ID NO 213
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 213
aucuacuguc ucacgugug                                           19

<210> SEQ ID NO 214
<211> LENGTH: 17
<212> TYPE: RNA
<213> ORGANISM: Artificial sequence
<220> FEATURE:
<223> OTHER INFORMATION: Antisense strand of siRNA

<400> SEQUENCE: 214
cacgugagac aguagau                                             17

<210> SEQ ID NO 215
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 215
gucuacuguc ucacgugua                                           19

<210> SEQ ID NO 216
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 216
uacacgugag acaguagac                                           19
```

-continued

```
<210> SEQ ID NO 217
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 217
ucuacugucu cacguguga                                              19

<210> SEQ ID NO 218
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 218
ucacacguga gacaguaga                                              19

<210> SEQ ID NO 219
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 219
cuacugucuc acgugugag                                              19

<210> SEQ ID NO 220
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 220
cucacacgug agacaguag                                              19

<210> SEQ ID NO 221
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 221
guacugucuc acgugugaa                                              19

<210> SEQ ID NO 222
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 222
uucacacgug agacaguac                                              19

<210> SEQ ID NO 223
<211> LENGTH: 19
<212> TYPE: RNA
<213> ORGANISM: Artificial sequence
<220> FEATURE:
```

<223> OTHER INFORMATION: Sense strand of siRNA

<400> SEQUENCE: 223
uacugucuca cgugugagg                                                19

<210> SEQ ID NO 224
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 224
ccucacacgu gagacagua                                                19

<210> SEQ ID NO 225
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 225
gacugucuca cgugugaga                                                19

<210> SEQ ID NO 226
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 226
ucucacacgu gagacaguc                                                19

<210> SEQ ID NO 227
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 227
acugucucac gugugaggu                                                19

<210> SEQ ID NO 228
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 228
accucacacg ugagacagu                                                19

<210> SEQ ID NO 229
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 229
cugucucacg ugugaggug                                                19

-continued

```
<210> SEQ ID NO 230
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 230
caccucacac gugagacag                                                    19

<210> SEQ ID NO 231
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 231
gugucucacg ugugaggua                                                    19

<210> SEQ ID NO 232
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 232
uaccucacac gugagacac                                                    19

<210> SEQ ID NO 233
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 233
ugucucacgu gugaggugc                                                    19

<210> SEQ ID NO 234
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 234
gcaccucaca cgugagaca                                                    19

<210> SEQ ID NO 235
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 235
ggucucacgu gugagguga                                                    19

<210> SEQ ID NO 236
<211> LENGTH: 19
<212> TYPE: RNA
<213> ORGANISM: Artificial sequence
<220> FEATURE:
<223> OTHER INFORMATION: Antisense strand of siRNA
```

-continued

```
<400> SEQUENCE: 236
ucaccucaca cgugagacc                                                    19

<210> SEQ ID NO 237
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 237
gucucacgug ugaggugcc                                                    19

<210> SEQ ID NO 238
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 238
ggcaccucac acgugagac                                                    19

<210> SEQ ID NO 239
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 239
cucucacgug ugaggugca                                                    19

<210> SEQ ID NO 240
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 240
ugcaccucac acgugagag                                                    19

<210> SEQ ID NO 241
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 241
ucucacgugu gaggugccc                                                    19

<210> SEQ ID NO 242
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 242
gggcaccuca cacgugaga                                                    19

<210> SEQ ID NO 243
<211> LENGTH: 19
```

```
<212> TYPE: RNA
<213> ORGANISM: Artificial sequence
<220> FEATURE:
<223> OTHER INFORMATION: Sense strand of siRNA

<400> SEQUENCE: 243
gcucacgugu gaggugcca                                                          19

<210> SEQ ID NO 244
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 244
uggcaccuca cacgugagc                                                          19

<210> SEQ ID NO 245
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 245
caugugcaag guguuuggg                                                          19

<210> SEQ ID NO 246
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 246
cccaaacacc uugcacaug                                                          19

<210> SEQ ID NO 247
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 247
gaugugcaag guguuugga                                                          19

<210> SEQ ID NO 248
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 248
uccaaacacc uugcacauc                                                          19

<210> SEQ ID NO 249
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 249
```

-continued augugcaagg uguuuggga                                                      19

<210> SEQ ID NO 250
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 250
ucccaaacac cuugcacau                                                      19

<210> SEQ ID NO 251
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 251
guaucuccau gcugguggc                                                      19

<210> SEQ ID NO 252
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 252
gccaccagca uggagauac                                                      19

<210> SEQ ID NO 253
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 253
cuaucuccau gcuggugga                                                      19

<210> SEQ ID NO 254
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 254
uccaccagca uggagauag                                                      19

<210> SEQ ID NO 255
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 255
uaucuccaug cugguggcg                                                      19

<210> SEQ ID NO 256
<211> LENGTH: 19
<212> TYPE: RNA
<213> ORGANISM: Artificial sequence -continued

```
<220> FEATURE:
<223> OTHER INFORMATION: Antisense strand of siRNA

<400> SEQUENCE: 256
cgccaccagc auggagaua                                                19

<210> SEQ ID NO 257
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 257
gaucuccaug cuggugggca                                               19

<210> SEQ ID NO 258
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 258
ugccaccagc auggagauc                                                19

<210> SEQ ID NO 259
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 259
aucuccaugc ugguggcgg                                                19

<210> SEQ ID NO 260
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 260
ccgccaccag cauggagau                                                19

<210> SEQ ID NO 261
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 261
gucuccaugc ugguggcga                                                19

<210> SEQ ID NO 262
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 262
ucgccaccag cauggagac                                                19
```

<210> SEQ ID NO 263
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 263
ucuccaugcu gguggcggg                                                                    19

<210> SEQ ID NO 264
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 264
cccgccacca gcauggaga                                                                    19

<210> SEQ ID NO 265
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 265
gcuccaugcu gguggcgga                                                                    19

<210> SEQ ID NO 266
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 266
uccgccacca gcauggagc                                                                    19

<210> SEQ ID NO 267
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 267
cuccaugcug guggcgggg                                                                    19

<210> SEQ ID NO 268
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 268
ccccgccacc agcauggag                                                                    19

<210> SEQ ID NO 269
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 269
guccaugcug guggcggga                                              19

<210> SEQ ID NO 270
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 270
ucccgccacc agcauggac                                              19

<210> SEQ ID NO 271
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 271
ucgagugacc aaggagaac                                              19

<210> SEQ ID NO 272
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 272
guucuccuug gucacucga                                              19

<210> SEQ ID NO 273
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 273
gcgagugacc aaggagaaa                                              19

<210> SEQ ID NO 274
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 274
uuucuccuug gucacucgc                                              19

<210> SEQ ID NO 275
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 275
guugcugcag cggaucacg                                              19

<210> SEQ ID NO 276

```
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 276
cgugauccgc ugcagcaac                                              19

<210> SEQ ID NO 277
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 277
cuugcugcag cggaucaca                                              19

<210> SEQ ID NO 278
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 278
ugugauccgc ugcagcaag                                              19

<210> SEQ ID NO 279
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 279
uugcugcagc ggaucacgc                                              19

<210> SEQ ID NO 280
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 280
gcgugauccg cugcagcaa                                              19

<210> SEQ ID NO 281
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 281
gugcugcagc ggaucacga                                              19

<210> SEQ ID NO 282
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 282
```

-continued ucgugauccg cugcagcac                                              19

<210> SEQ ID NO 283
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 283
ugcugcagcg gaucacgca                                             19

<210> SEQ ID NO 284
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 284
ugcgugaucc gcugcagca                                             19

<210> SEQ ID NO 285
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 285
gcugcagcgg aucacgcag                                             19

<210> SEQ ID NO 286
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 286
cugcgugauc cgcugcagc                                             19

<210> SEQ ID NO 287
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 287
ccugcagcgg aucacgcaa                                             19

<210> SEQ ID NO 288
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 288
uugcgugauc cgcugcagg                                             19

<210> SEQ ID NO 289
<211> LENGTH: 19
<212> TYPE: RNA

<213> ORGANISM: Artificial sequence
<220> FEATURE:
<223> OTHER INFORMATION: Sense strand of siRNA

<400> SEQUENCE: 289
cugcagcgga ucacgcagg                                                        19

<210> SEQ ID NO 290
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 290
ccugcgugau ccgcugcag                                                        19

<210> SEQ ID NO 291
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 291
gugcagcgga ucacgcaga                                                        19

<210> SEQ ID NO 292
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 292
ucugcgugau ccgcugcac                                                        19

<210> SEQ ID NO 293
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 293
ugcagcggau cacgcagga                                                        19

<210> SEQ ID NO 294
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 294
uccugcguga uccgcugca                                                        19

<210> SEQ ID NO 295
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 295
gcagcggauc acgcaggag                                                        19

-continued

<210> SEQ ID NO 296
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 296
cuccugcgug auccgcugc                                                          19

<210> SEQ ID NO 297
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 297
ccagcggauc acgcaggaa                                                          19

<210> SEQ ID NO 298
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 298
uuccugcgug auccgcugg                                                          19

<210> SEQ ID NO 299
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 299
cagcggauca cgcaggagc                                                          19

<210> SEQ ID NO 300
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 300
gcuccugcgu gauccgcug                                                          19

<210> SEQ ID NO 301
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 301
gagcggauca cgcaggaga                                                          19

<210> SEQ ID NO 302
<211> LENGTH: 19
<212> TYPE: RNA
<213> ORGANISM: Artificial sequence
<220> FEATURE:

-continued

<223> OTHER INFORMATION: Antisense strand of siRNA

<400> SEQUENCE: 302
ucuccugcgu gauccgcuc                                                    19

<210> SEQ ID NO 303
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 303
agcggaucac gcaggagca                                                    19

<210> SEQ ID NO 304
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 304
ugcuccugcg ugauccgcu                                                    19

<210> SEQ ID NO 305
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 305
gcggaucacg caggagcag                                                    19

<210> SEQ ID NO 306
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 306
cugcuccugc gugauccgc                                                    19

<210> SEQ ID NO 307
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 307
ccggaucacg caggagcaa                                                    19

<210> SEQ ID NO 308
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 308
uugcuccugc gugauccgg                                                    19

```
<210> SEQ ID NO 309
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 309
cggaucacgc aggagcagg                                              19

<210> SEQ ID NO 310
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 310
ccugcuccug cgugauccg                                              19

<210> SEQ ID NO 311
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 311
gggaucacgc aggagcaga                                              19

<210> SEQ ID NO 312
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 312
ucugcuccug cgugauccc                                              19

<210> SEQ ID NO 313
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 313
ggaucacgca ggagcagga                                              19

<210> SEQ ID NO 314
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 314
uccugcuccu gcgugaucc                                              19

<210> SEQ ID NO 315
<211> LENGTH: 19
<212> TYPE: RNA
<213> ORGANISM: Artificial sequence
<220> FEATURE:
<223> OTHER INFORMATION: Sense strand of siRNA
```

-continued

<400> SEQUENCE: 315
gaucacgcag gagcaggag                                                                  19

<210> SEQ ID NO 316
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 316
cuccugcucc ugcgugauc                                                                  19

<210> SEQ ID NO 317
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 317
caucacgcag gagcaggaa                                                                  19

<210> SEQ ID NO 318
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 318
uuccugcucc ugcgugaug                                                                  19

<210> SEQ ID NO 319
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 319
aucacgcagg agcaggaga                                                                  19

<210> SEQ ID NO 320
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 320
ucuccugcuc cugcgugau                                                                  19

<210> SEQ ID NO 321
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 321
cugccaucca gucccugga                                                                  19

<210> SEQ ID NO 322
<211> LENGTH: 19

<212> TYPE: RNA
<213> ORGANISM: Artificial sequence
<220> FEATURE:
<223> OTHER INFORMATION: Antisense strand of siRNA

<400> SEQUENCE: 322
uccagggacu ggauggcag                                                    19

<210> SEQ ID NO 323
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 323
ugccauccag ucccuggac                                                    19

<210> SEQ ID NO 324
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 324
guccagggac uggauggca                                                    19

<210> SEQ ID NO 325
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 325
ggccauccag ucccuggaa                                                    19

<210> SEQ ID NO 326
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 326
uuccagggac uggauggcc                                                    19

<210> SEQ ID NO 327
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 327
cuuccaaggg cugccagcu                                                    19

<210> SEQ ID NO 328
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 328

-continued agcuggcagc ccuuggaag                                                              19

<210> SEQ ID NO 329
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 329
uuccaagggc ugccagcug                                                              19

<210> SEQ ID NO 330
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 330
cagcuggcag cccuuggaa                                                              19

<210> SEQ ID NO 331
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 331
guccaagggc ugccagcua                                                              19

<210> SEQ ID NO 332
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 332
uagcuggcag cccuuggac                                                              19

<210> SEQ ID NO 333
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 333
uccaagggcu gccagcugg                                                              19

<210> SEQ ID NO 334
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 334
ccagcuggca gcccuugga                                                              19

<210> SEQ ID NO 335
<211> LENGTH: 19
<212> TYPE: RNA
<213> ORGANISM: Artificial sequence -continued

```
<220> FEATURE:
<223> OTHER INFORMATION: Sense strand of siRNA

<400> SEQUENCE: 335
gccaagggcu gccagcuga                                               19

<210> SEQ ID NO 336
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 336
ucagcuggca gcccuuggc                                               19

<210> SEQ ID NO 337
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 337
ccaagggcug ccagcuggg                                               19

<210> SEQ ID NO 338
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 338
cccagcuggc agcccuugg                                               19

<210> SEQ ID NO 339
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 339
gcaagggcug ccagcugga                                               19

<210> SEQ ID NO 340
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 340
uccagcuggc agcccuugc                                               19

<210> SEQ ID NO 341
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 341
caagggcugc cagcugggg                                               19
```

-continued

<210> SEQ ID NO 342
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 342
ccccagcugg cagcccuug                                                    19

<210> SEQ ID NO 343
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 343
gaagggcugc cagcuggga                                                    19

<210> SEQ ID NO 344
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 344
ucccagcugg cagcccuuc                                                    19

<210> SEQ ID NO 345
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 345
aagggcugcc agcugggga                                                    19

<210> SEQ ID NO 346
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 346
uccccagcug gcagcccuu                                                    19

<210> SEQ ID NO 347
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 347
agggcugcca gcuggggaa                                                    19

<210> SEQ ID NO 348
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 348
uuccccagcu ggcagcccu                                                    19

<210> SEQ ID NO 349
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 349
gggcugccag cuggggaag                                                    19

<210> SEQ ID NO 350
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 350
cuuccccagc uggcagccc                                                    19

<210> SEQ ID NO 351
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 351
cggcugccag cuggggaaa                                                    19

<210> SEQ ID NO 352
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 352
uuuccccagc uggcagccg                                                    19

<210> SEQ ID NO 353
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 353
ggcugccagc uggggaaga                                                    19

<210> SEQ ID NO 354
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 354
ucuuccccag cuggcagcc                                                    19

<210> SEQ ID NO 355

-continued

```
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 355
gcugccagcu ggggaagac                                                        19

<210> SEQ ID NO 356
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 356
gucuucccca gcuggcagc                                                        19

<210> SEQ ID NO 357
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 357
ccugccagcu ggggaagaa                                                        19

<210> SEQ ID NO 358
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 358
uucuucccca gcuggcagg                                                        19

<210> SEQ ID NO 359
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 359
cugccagcug gggaagaca                                                        19

<210> SEQ ID NO 360
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 360
ugucuucccc agcuggcag                                                        19

<210> SEQ ID NO 361
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 361
```

-continued ugccagcugg ggaagacag                                          19

<210> SEQ ID NO 362
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 362
cugucuuccc cagcuggca                                          19

<210> SEQ ID NO 363
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 363
ggccagcugg ggaagacaa                                          19

<210> SEQ ID NO 364
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 364
uugucuuccc cagcuggcc                                          19

<210> SEQ ID NO 365
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 365
gccagcuggg gaagacaga                                          19

<210> SEQ ID NO 366
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 366
ucugucuucc ccagcuggc                                          19

<210> SEQ ID NO 367
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 367
ccagcugggg aagacagag                                          19

<210> SEQ ID NO 368
<211> LENGTH: 19
<212> TYPE: RNA

<213> ORGANISM: Artificial sequence
<220> FEATURE:
<223> OTHER INFORMATION: Antisense strand of siRNA

<400> SEQUENCE: 368
cucugucuuc cccagcugg                                                       19

<210> SEQ ID NO 369
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 369
gcagcugggg aagacagaa                                                       19

<210> SEQ ID NO 370
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 370
uucugucuuc cccagcugc                                                       19

<210> SEQ ID NO 371
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 371
cagcugggga agacagagc                                                       19

<210> SEQ ID NO 372
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 372
gcucugucuu ccccagcug                                                       19

<210> SEQ ID NO 373
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 373
gagcugggga agacagaga                                                       19

<210> SEQ ID NO 374
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 374
ucucugucuu ccccagcuc                                                       19

-continued

```
<210> SEQ ID NO 375
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 375
agcuggggaa gacagagca                                                    19

<210> SEQ ID NO 376
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 376
ugcucugucu uccccagcu                                                    19

<210> SEQ ID NO 377
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 377
gcuggggaag acagagcag                                                    19

<210> SEQ ID NO 378
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 378
cugcucuguc uuccccagc                                                    19

<210> SEQ ID NO 379
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 379
ccuggggaag acagagcaa                                                    19

<210> SEQ ID NO 380
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 380
uugcucuguc uuccccagg                                                    19

<210> SEQ ID NO 381
<211> LENGTH: 19
<212> TYPE: RNA
<213> ORGANISM: Artificial sequence
<220> FEATURE:
```

-continued

<223> OTHER INFORMATION: Sense strand of siRNA

<400> SEQUENCE: 381
agggcuuuga gaacaugga                                          19

<210> SEQ ID NO 382
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 382
uccauguucu caaagcccu                                          19

<210> SEQ ID NO 383
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 383
gggcuuugag aacauggac                                          19

<210> SEQ ID NO 384
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 384
guccauguuc ucaaagccc                                          19

<210> SEQ ID NO 385
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 385
cggcuuugag aacauggaa                                          19

<210> SEQ ID NO 386
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 386
uuccauguuc ucaaagccg                                          19

<210> SEQ ID NO 387
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 387
ggcuuugaga acauggacu                                          19

<210> SEQ ID NO 388
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 388
aguccauguu cucaaagcc                                                19

<210> SEQ ID NO 389
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 389
gcuuugagaa cauggacuu                                                19

<210> SEQ ID NO 390
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 390
aaguccaugu ucucaaagc                                                19

<210> SEQ ID NO 391
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 391
gagccauuga cuuugggac                                                19

<210> SEQ ID NO 392
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 392
gucccaaagu caauggcuc                                                19

<210> SEQ ID NO 393
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 393
cagccauuga cuuugggaa                                                19

<210> SEQ ID NO 394
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 394
uucccaaagu caauggcug                                                          19

<210> SEQ ID NO 395
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 395
agccauugac uuugggaca                                                          19

<210> SEQ ID NO 396
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 396
ugucccaaag ucaauggcu                                                          19

<210> SEQ ID NO 397
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 397
gccauugacu uuggggacag                                                         19

<210> SEQ ID NO 398
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 398
cugucccaaa gucaauggc                                                          19

<210> SEQ ID NO 399
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 399
cccauugacu uugggacaa                                                          19

<210> SEQ ID NO 400
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 400
uugucccaaa gucaauggg                                                          19

<210> SEQ ID NO 401
<211> LENGTH: 19

-continued

```
<212> TYPE: RNA
<213> ORGANISM: Artificial sequence
<220> FEATURE:
<223> OTHER INFORMATION: Sense strand of siRNA

<400> SEQUENCE: 401
ccauugacuu ugggacaga                                              19

<210> SEQ ID NO 402
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 402
ucugucccaa agucaaugg                                              19

<210> SEQ ID NO 403
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 403
cauugacuuu gggacagau                                              19

<210> SEQ ID NO 404
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 404
aucuguccca aagucaaug                                              19

<210> SEQ ID NO 405
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 405
auugacuuug ggacagaug                                              19

<210> SEQ ID NO 406
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 406
caucuguccc aaagucaau                                              19

<210> SEQ ID NO 407
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 407
```

-continued guugacuuug ggacagaua                                                                    19

<210> SEQ ID NO 408
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 408
uaucuguccc aaagucaac                                                                    19

<210> SEQ ID NO 409
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 409
uugacuuugg gacagauga                                                                    19

<210> SEQ ID NO 410
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 410
ucaucugucc caaagucaa                                                                    19

<210> SEQ ID NO 411
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 411
ugacuuuggg acagaugag                                                                    19

<210> SEQ ID NO 412
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 412
cucaucuguc ccaaaguca                                                                    19

<210> SEQ ID NO 413
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 413
ggacuuuggg acagaugaa                                                                    19

<210> SEQ ID NO 414
<211> LENGTH: 19
<212> TYPE: RNA
<213> ORGANISM: Artificial sequence -continued
<220> FEATURE:
<223> OTHER INFORMATION: Antisense strand of siRNA

<400> SEQUENCE: 414
uucaucuguc ccaaagucc                                                                                19

<210> SEQ ID NO 415
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 415
gacuuuggga cagaugagg                                                                                19

<210> SEQ ID NO 416
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 416
ccucaucugu cccaaaguc                                                                                19

<210> SEQ ID NO 417
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 417
cacuuuggga cagaugaga                                                                                19

<210> SEQ ID NO 418
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 418
ucucaucugu cccaaagug                                                                                19

<210> SEQ ID NO 419
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 419
acuuugggac agaugagga                                                                                19

<210> SEQ ID NO 420
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 420
uccucaucug ucccaaagu                                                                                19

-continued

<210> SEQ ID NO 421
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 421
cuuugggaca gaugaggaa                                                              19

<210> SEQ ID NO 422
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 422
uuccucaucu gucccaaag                                                              19

<210> SEQ ID NO 423
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 423
gaugucuucu cucugcuca                                                              19

<210> SEQ ID NO 424
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 424
ugagcagaga gaagacauc                                                              19

<210> SEQ ID NO 425
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 425
augucuucuc ucugcucag                                                              19

<210> SEQ ID NO 426
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 426
cugagcagag agaagacau                                                              19

<210> SEQ ID NO 427
<211> LENGTH: 19
<212> TYPE: RNA
<213> ORGANISM: Artificial sequence
<220> FEATURE:
<223> OTHER INFORMATION: Sense strand of siRNA -continued

<400> SEQUENCE: 427
gugucuucuc ucugcucaa                                                          19

<210> SEQ ID NO 428
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 428
uugagcagag agaagacac                                                          19

<210> SEQ ID NO 429
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 429
ugucuucucu cugcucaga                                                          19

<210> SEQ ID NO 430
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 430
ucugagcaga gagaagaca                                                          19

<210> SEQ ID NO 431
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 431
gucuucucuc ugcucagag                                                          19

<210> SEQ ID NO 432
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 432
cucugagcag agagaagac                                                          19

<210> SEQ ID NO 433
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 433
cucuucucuc ugcucagaa                                                          19

<210> SEQ ID NO 434

-continued

```
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 434
uucugagcag agagaagag                                               19

<210> SEQ ID NO 435
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 435
ucuucucucu gcucagaga                                               19

<210> SEQ ID NO 436
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 436
ucucugagca gagagaaga                                               19

<210> SEQ ID NO 437
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 437
cuucucucug cucagagag                                               19

<210> SEQ ID NO 438
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 438
cucucugagc agagagaag                                               19

<210> SEQ ID NO 439
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 439
guucucucug cucagagaa                                               19

<210> SEQ ID NO 440
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 440
```

-continued

```
uucucugagc agagagaac                                         19

<210> SEQ ID NO 441
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 441
uucucucugc ucagagagc                                         19

<210> SEQ ID NO 442
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 442
gcucucugag cagagagaa                                         19

<210> SEQ ID NO 443
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 443
gucucucugc ucagagaga                                         19

<210> SEQ ID NO 444
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 444
ucucucugag cagagagac                                         19

<210> SEQ ID NO 445
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 445
ucucucugcu cagagagca                                         19

<210> SEQ ID NO 446
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 446
ugcucucuga gcagagaga                                         19

<210> SEQ ID NO 447
<211> LENGTH: 19
<212> TYPE: RNA
```

-continued

```
<213> ORGANISM: Artificial sequence
<220> FEATURE:
<223> OTHER INFORMATION: Sense strand of siRNA

<400> SEQUENCE: 447
cucucugcuc agagagcag                                                      19

<210> SEQ ID NO 448
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 448
cugcucucug agcagagag                                                      19

<210> SEQ ID NO 449
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 449
gucucugcuc agagagcaa                                                      19

<210> SEQ ID NO 450
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 450
uugcucucug agcagagac                                                      19

<210> SEQ ID NO 451
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 451
ucucugcuca gagagcagg                                                      19

<210> SEQ ID NO 452
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 452
ccugcucucu gagcagaga                                                      19

<210> SEQ ID NO 453
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 453
gcucugcuca gagagcaga                                                      19
```

<210> SEQ ID NO 454
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 454
ucugcucucu gagcagagc                                                                    19

<210> SEQ ID NO 455
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 455
cucugcucag agagcaggg                                                                    19

<210> SEQ ID NO 456
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 456
cccugcucuc ugagcagag                                                                    19

<210> SEQ ID NO 457
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 457
gucugcucag agagcagga                                                                    19

<210> SEQ ID NO 458
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 458
uccugcucuc ugagcagac                                                                    19

<210> SEQ ID NO 459
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 459
ucugcucaga gagcaggga                                                                    19

<210> SEQ ID NO 460
<211> LENGTH: 19
<212> TYPE: RNA
<213> ORGANISM: Artificial sequence
<220> FEATURE:

-continued

<223> OTHER INFORMATION: Antisense strand of siRNA

<400> SEQUENCE: 460
ucccugcucu cugagcaga                                                    19

<210> SEQ ID NO 461
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 461
cugcucagag agcagggac                                                    19

<210> SEQ ID NO 462
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 462
gucccugcuc ucugagcag                                                    19

<210> SEQ ID NO 463
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 463
gugcucagag agcagggaa                                                    19

<210> SEQ ID NO 464
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 464
uucccugcuc ucugagcac                                                    19

<210> SEQ ID NO 465
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 465
ugcucagaga gcagggacu                                                    19

<210> SEQ ID NO 466
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 466
agucccugcu cucugagca                                                    19

-continued

```
<210> SEQ ID NO 467
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 467
gcucagagag cagggacua                                               19

<210> SEQ ID NO 468
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 468
uagucccugc ucucugagc                                               19

<210> SEQ ID NO 469
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 469
cucagagagc agggacuag                                               19

<210> SEQ ID NO 470
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 470
cuagucccug cucucugag                                               19

<210> SEQ ID NO 471
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 471
gucagagagc agggacuaa                                               19

<210> SEQ ID NO 472
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 472
uuagucccug cucucugac                                               19

<210> SEQ ID NO 473
<211> LENGTH: 19
<212> TYPE: RNA
<213> ORGANISM: Artificial sequence
<220> FEATURE:
<223> OTHER INFORMATION: Sense strand of siRNA
```

-continued

```
<400> SEQUENCE: 473
ucagagagca gggacuagg                                                    19

<210> SEQ ID NO 474
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 474 ccuagcccu gcucucuga                                                     19

<210> SEQ ID NO 475
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 475
gcagagagca gggacuaga                                                    19

<210> SEQ ID NO 476
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 476 ucuagcccu gcucucugc                                                     19

<210> SEQ ID NO 477
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 477
cacacaggac acuuuucua                                                    19

<210> SEQ ID NO 478
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 478
uagaaaagug uccugugug                                                    19

<210> SEQ ID NO 479
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 479
acacaggaca cuuuucuac                                                    19

<210> SEQ ID NO 480
<211> LENGTH: 19
```

-continued

```
<212> TYPE: RNA
<213> ORGANISM: Artificial sequence
<220> FEATURE:
<223> OTHER INFORMATION: Antisense strand of siRNA

<400> SEQUENCE: 480
guagaaaagu guccugugu                                                                    19

<210> SEQ ID NO 481
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 481
gcacaggaca cuuuucuaa                                                                    19

<210> SEQ ID NO 482
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 482
uuagaaaagu guccugugc                                                                    19

<210> SEQ ID NO 483
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 483
cacaggacac uuuucuaca                                                                    19

<210> SEQ ID NO 484
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 484
uguagaaaag uguccugug                                                                    19

<210> SEQ ID NO 485
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 485 cauuuuaaa augugauuu                                                                     19

<210> SEQ ID NO 486
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 486
```
aaaucacauu uuaaaaaug                                                      19

<210> SEQ ID NO 487
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 487
auuuuuaaaa ugugauuuu                                                      19

<210> SEQ ID NO 488
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 488
aaaaucacau uuuaaaaau                                                      19

<210> SEQ ID NO 489
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 489
uuuuuaaaau gugauuuuu                                                      19

<210> SEQ ID NO 490
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 490
aaaaaucaca uuuuaaaaa                                                      19

<210> SEQ ID NO 491
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 491
uuuuaaaaug ugauuuuug                                                      19

<210> SEQ ID NO 492
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 492
caaaaaucac auuuuaaaa                                                      19

<210> SEQ ID NO 493
<211> LENGTH: 19
<212> TYPE: RNA
<213> ORGANISM: Artificial sequence -continued

<220> FEATURE:
<223> OTHER INFORMATION: Sense strand of siRNA

<400> SEQUENCE: 493

guuuaaaaug ugauuuuua                                                                       19

<210> SEQ ID NO 494
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 494

uaaaaaucac auuuuaaac                                                                       19

<210> SEQ ID NO 495
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 495

uuuaaaaugu gauuuuugu                                                                       19

<210> SEQ ID NO 496
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 496

acaaaaauca cauuuuaaa                                                                       19

<210> SEQ ID NO 497
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 497

uuaaaaugug auuuuugua                                                                       19

<210> SEQ ID NO 498
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 498

uacaaaaauc acauuuuaa                                                                       19

<210> SEQ ID NO 499
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 499

uaaaauguga uuuuuguau                                                                       19

-continued

```
<210> SEQ ID NO 500
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 500
auacaaaaau cacauuuua                                            19

<210> SEQ ID NO 501
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 501
aaaaugugau uuuguaua                                             19

<210> SEQ ID NO 502
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 502
uauacaaaaa ucacauuu                                             19

<210> SEQ ID NO 503
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 503
aaaugugauu uuguauau                                             19

<210> SEQ ID NO 504
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 504
auauacaaaa aucacauuu                                            19

<210> SEQ ID NO 505
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 505
aaugugauuu uuguauaua                                            19

<210> SEQ ID NO 506
<211> LENGTH: 19
<212> TYPE: RNA
<213> ORGANISM: Artificial sequence
<220> FEATURE:
<223> OTHER INFORMATION: Antisense strand of siRNA
```

<400> SEQUENCE: 506
uauauacaaa aaucacauu                                                    19

<210> SEQ ID NO 507
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 507
augugauuuu uguauauac                                                    19

<210> SEQ ID NO 508
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 508
guauauacaa aaaucacau                                                    19

<210> SEQ ID NO 509
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 509
gugugauuuu uguauauaa                                                    19

<210> SEQ ID NO 510
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 510
uuauauacaa aaaucacac                                                    19

<210> SEQ ID NO 511
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 511
ugugauuuuu guauauacu                                                    19

<210> SEQ ID NO 512
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 512
aguauauaca aaaaucaca                                                    19

<210> SEQ ID NO 513

-continued

```
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 513
gugauuuuug uauauacuu                                                      19

<210> SEQ ID NO 514
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 514
aaguauauac aaaaaucac                                                      19

<210> SEQ ID NO 515
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 515
ugauuuuugu auauacuug                                                      19

<210> SEQ ID NO 516
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 516
caaguauaua caaaaauca                                                      19

<210> SEQ ID NO 517
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 517
ggauuuuugu auauacuua                                                      19

<210> SEQ ID NO 518
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 518
uaaguauaua caaaaaucc                                                      19

<210> SEQ ID NO 519
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 519
```
gauuuuugua uauacuugu                                              19

<210> SEQ ID NO 520
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 520
acaaguauau acaaaaauc                                             19

<210> SEQ ID NO 521
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 521
auuuuuguau auacuugua                                             19

<210> SEQ ID NO 522
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 522
uacaaguaua uacaaaaau                                             19

<210> SEQ ID NO 523
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 523
uuuuuguaua uacuuguau                                             19

<210> SEQ ID NO 524
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 524
auacaaguau auacaaaaa                                             19

<210> SEQ ID NO 525
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 525
uuuuguauau acuuguaua                                             19

<210> SEQ ID NO 526
<211> LENGTH: 19
<212> TYPE: RNA

-continued

```
<213> ORGANISM: Artificial sequence
<220> FEATURE:
<223> OTHER INFORMATION: Antisense strand of siRNA

<400> SEQUENCE: 526
uauacaagua uauacaaaa                                            19

<210> SEQ ID NO 527
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 527
uuuguauaua cuuguauau                                            19

<210> SEQ ID NO 528
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 528
auauacaagu auauacaaa                                            19

<210> SEQ ID NO 529
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 529
uuguauauac uuguauaug                                            19

<210> SEQ ID NO 530
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 530
cauauacaag uauauacaa                                            19

<210> SEQ ID NO 531
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 531
guguauauac uuguauaua                                            19

<210> SEQ ID NO 532
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 532
uauauacaag uauauacac                                            19
```

-continued

```
<210> SEQ ID NO 533
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 533
uguauauacu uguauaugu                                                    19

<210> SEQ ID NO 534
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 534
acauauacaa guauauaca                                                    19

<210> SEQ ID NO 535
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 535
guauauacuu guauaugua                                                    19

<210> SEQ ID NO 536
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 536
uacauauaca aguauauac                                                    19

<210> SEQ ID NO 537
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 537
uauauacuug uauauguau                                                    19

<210> SEQ ID NO 538
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 538
auacauauac aaguauaua                                                    19

<210> SEQ ID NO 539
<211> LENGTH: 19
<212> TYPE: RNA
<213> ORGANISM: Artificial sequence
<220> FEATURE:
```

-continued

<223> OTHER INFORMATION: Sense strand of siRNA

<400> SEQUENCE: 539
auauacuugu auauguaug                                              19

<210> SEQ ID NO 540
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 540
cauacauaua caaguauau                                              19

<210> SEQ ID NO 541
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 541
guauacuugu auauguaua                                              19

<210> SEQ ID NO 542
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 542
uauacauaua caaguauac                                              19

<210> SEQ ID NO 543
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 543
uauacuugua uauguaugc                                              19

<210> SEQ ID NO 544
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 544
gcauacauau acaaguaua                                              19

<210> SEQ ID NO 545
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 545
gauacuugua uauguauga                                              19

-continued

<210> SEQ ID NO 546
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 546
ucauacauau acaaguauc                                                           19

<210> SEQ ID NO 547
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 547
auacuuguau auguaugcc                                                           19

<210> SEQ ID NO 548
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 548
ggcauacaua uacaaguau                                                           19

<210> SEQ ID NO 549
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 549
guacuuguau auguaugca                                                           19

<210> SEQ ID NO 550
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 550
ugcauacaua uacaaguac                                                           19

<210> SEQ ID NO 551
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 551
uacuuguaua uguaugcca                                                           19

<210> SEQ ID NO 552
<211> LENGTH: 19
<212> TYPE: RNA
<213> ORGANISM: Artificial sequence
<220> FEATURE:
<223> OTHER INFORMATION: Antisense strand of siRNA -continued

```
<400> SEQUENCE: 552
uggcauacau auacaagua                                            19

<210> SEQ ID NO 553
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 553
acuuguauau guaugccaa                                            19

<210> SEQ ID NO 554
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 554
uuggcauaca uauacaagu                                            19

<210> SEQ ID NO 555
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 555
cuuguauaug uaugccaau                                            19

<210> SEQ ID NO 556
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 556
auuggcauac auauacaag                                            19

<210> SEQ ID NO 557
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 557
uuguauaugu augccaauu                                            19

<210> SEQ ID NO 558
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 558
aauuggcaua cauauacaa                                            19

<210> SEQ ID NO 559
<211> LENGTH: 19
```

-continued

```
<212> TYPE: RNA
<213> ORGANISM: Artificial sequence
<220> FEATURE:
<223> OTHER INFORMATION: Sense strand of siRNA

<400> SEQUENCE: 559
uguauaugua ugccaauuu                                                      19

<210> SEQ ID NO 560
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 560
aaauuggcau acauauaca                                                      19

<210> SEQ ID NO 561
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 561
guauauguau gccaauuug                                                      19

<210> SEQ ID NO 562
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 562
caaauuggca uacauauac                                                      19

<210> SEQ ID NO 563
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 563
cuauauguau gccaauuua                                                      19

<210> SEQ ID NO 564
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 564
uaaauuggca uacauauag                                                      19

<210> SEQ ID NO 565
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 565
```
uauauguaug ccaauuugg                                              19

<210> SEQ ID NO 566
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 566
ccaaauuggc auacauaua                                             19

<210> SEQ ID NO 567
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 567
gauauguaug ccaauuuga                                             19

<210> SEQ ID NO 568
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 568
ucaaauuggc auacauauc                                             19

<210> SEQ ID NO 569
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 569
auauguaugc caauuuggu                                             19

<210> SEQ ID NO 570
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 570
accaaauugg cauacauau                                             19

<210> SEQ ID NO 571
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 571
uauguaugcc aauuuggug                                             19

<210> SEQ ID NO 572
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 572
caccaaauug gcauacaua                                                                                   19

<210> SEQ ID NO 573
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 573
gauguaugcc aauuuggua                                                                                   19

<210> SEQ ID NO 574
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 574
uaccaaauug gcauacauc                                                                                   19

<210> SEQ ID NO 575
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 575
auguaugcca auuuggugc                                                                                   19

<210> SEQ ID NO 576
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 576
gcaccaaauu ggcauacau                                                                                   19

<210> SEQ ID NO 577
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 577
guguaugcca auuugguga                                                                                   19

<210> SEQ ID NO 578
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 578
ucaccaaauu ggcauacac                                                                                   19

<210> SEQ ID NO 579
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 579
uguaugccaa uuuggugcu                                                                                       19

<210> SEQ ID NO 580
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 580
agcaccaaau uggcauaca                                                                                       19

<210> SEQ ID NO 581
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 581
guaugccaau uuggugcuu                                                                                       19

<210> SEQ ID NO 582
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 582
aagcaccaaa uuggcauac                                                                                       19

<210> SEQ ID NO 583
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 583
uaugccaauu uggugcuuu                                                                                       19

<210> SEQ ID NO 584
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 584
aaagcaccaa auuggcaua                                                                                       19

<210> SEQ ID NO 585
<211> LENGTH: 19
<212> TYPE: RNA
<213> ORGANISM: Artificial sequence
<220> FEATURE:
<223> OTHER INFORMATION: Sense strand of siRNA -continued

```
<400> SEQUENCE: 585
augccaauuu ggugcuuuu                                              19

<210> SEQ ID NO 586
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 586
aaaagcacca aauuggcau                                             19

<210> SEQ ID NO 587
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 587
ugccaauuug gugcuuuuu                                             19

<210> SEQ ID NO 588
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 588
aaaaagcacc aaauuggca                                             19

<210> SEQ ID NO 589
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 589
gccaauuugg ugcuuuuug                                             19

<210> SEQ ID NO 590
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 590
caaaaagcac caaauuggc                                             19

<210> SEQ ID NO 591
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 591
cccaauuugg ugcuuuuua                                             19

<210> SEQ ID NO 592
```

-continued

```
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 592
uaaaaagcac caaauuggg                                                19

<210> SEQ ID NO 593
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 593
ccaauuuggu gcuuuuugu                                                19

<210> SEQ ID NO 594
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 594
acaaaaagca ccaaauugg                                                19

<210> SEQ ID NO 595
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 595
caauuuggug cuuuuugua                                                19

<210> SEQ ID NO 596
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 596 uacaaaagc accaaauug                                                 19

<210> SEQ ID NO 597
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 597
aauuuggugc uuuuuguaa                                                19

<210> SEQ ID NO 598
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 598
```

-continued uuacaaaaag caccaaauu                                                19

<210> SEQ ID NO 599
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 599
aguuuguguu auauguugu                                                19

<210> SEQ ID NO 600
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 600
acaacauaua acacaaacu                                                19

<210> SEQ ID NO 601
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 601
guuuguguua uauguuguu                                                19

<210> SEQ ID NO 602
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 602
aacaacauau aacacaaac                                                19

<210> SEQ ID NO 603
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 603
uuuguguuau auguuguuu                                                19

<210> SEQ ID NO 604
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 604
aaacaacaua uaacacaaa                                                19

<210> SEQ ID NO 605
<211> LENGTH: 19
<212> TYPE: RNA

<213> ORGANISM: Artificial sequence
<220> FEATURE:
<223> OTHER INFORMATION: Sense strand of siRNA

<400> SEQUENCE: 605
uuguguuaua uguuguuuu                                                                                                           19

<210> SEQ ID NO 606
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 606
aaaacaacau auaacacaa                                                                                                           19

<210> SEQ ID NO 607
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 607
uguguuauau guuguuuua                                                                                                           19

<210> SEQ ID NO 608
<211> LENGTH: 19
<212> TYPE: RNA
<213> ORGANISM: Artificial sequence
<220> FEATURE:
<223> OTHER INFORMATION: Antisense strand of siRNA

<400> SEQUENCE: 608
uaaaacaaca uauaacaca                                                                                                           19

<210> SEQ ID NO 609
<211> LENGTH: 1771
<212> TYPE: DNA
<213> ORGANISM: Homo sapiens

<400> SEQUENCE: 609
agacagaatt cgggcaccag gagaaggaag ccaacaggat ccgacccggt gttttgtgac      60
aaaggcaaga cccccaggtc tacttagagc aaagttagta gaggaggcag ctaggcgtgg     120
ctctcattcc ttcccacaga atggattata agtcgagcct gatccaggat gggaatccca     180
tggagaactt ggagaagcag ctgatctgcc ctatctgcct ggagatgttt accaagccag     240
tggtcatctt gccgtgccag cacaacctgt gccggaagtg tgccaatgac atcttccagg     300
ctgcaaatcc ctactggacc agccggggca gctcagtgtc catgtctgga ggccgtttcc     360
gctgccccac ctgccgccac gaggtgatca tggatcgtca cggagtgtac ggcctgcaga     420
ggaacctgct ggtggagaac atcatcgaca tctacaaaca ggagtgctcc agtcggccgc     480
tgcagaaggg cagtcacccc atgtgcaagg agcacgaaga tgagaaaatc aacatctact     540
gtctcacgtg tgaggtgccc acctgctcca tgtgcaaggt gtttgggatc cacaaggcct     600
gcgaggtggc cccattgcag agtgtcttcc agggacaaaa gactgaactg aataactgta     660
tctccatgct ggtggcgggg aatgaccgtg tgcagaccat catcactcag ctggaggatt     720
cccgtcgagt gaccaaggag aacagtcacc aggtaaagga agagctgagc cagaagtttg     780
acacgttgta tgccatcctg gatgagaaga aaagtgagtt gctgcagcgg atcacgcagg     840

-continued

```
agcaggagaa aaagcttagc ttcatcgagg ccctcatcca gcagtaccag gagcagctgg      900
acaagtccac aaagctggtg gaaactgcca tccagtccct ggacgagcct gggggagcca      960
ccttcctctt gactgccaag caactcatca aaagcattgt ggaagcttcc aagggctgcc     1020
agctggggaa gacagagcag ggctttgaga acatggactt ctttactttg gatttagagc     1080
acatagcaga cgccctgaga gccattgact ttgggacaga tgaggaagag gaagaattca     1140
ttgaagaaga agatcaggaa gaggaagagt ccacagaagg gaaggaagaa ggacaccagt     1200
aaggagctgg atgaatgaga ggcccccaga tgcagagaga ctggagaggg tggggagggg     1260
cccagcggcc ttggtgacag gcccaggatg ggaggggtcg gggcccctgg aggggcaatg     1320
gggaggtgat gtcttctctc tgctcagaga gcagggacta gggtaggacc ctcaccgctg     1380
cgtccagcag acactgaacc agaattggaa acgtgcttga aacaatcaca caggacactt     1440
ttctacattg gtgcaaaatg gaatattttg tacatttta aaatgtgatt tttgtatata     1500
cttgtatatg tatgccaatt tggtgctttt tgtaaaggaa cttttgtata ataatgcctg     1560
gtcgttgggt gacctgcgat tgtcagaaag aggggaagga agccaggttg atacagctgc     1620
ccacttcctt tcctgagcag gaggatgggg tagcactcac agggacgatg tgctgtattt     1680
cagtgcctat cccagacata cggggtggta actgagtttg tgttatatgt tgttttaata     1740
aatgcacaat gctctcttcc tgttcttcaa a                                    1771
```

```
<210> SEQ ID NO 610
<211> LENGTH: 353
<212> TYPE: PRT
<213> ORGANISM: Homo sapiens

<400> SEQUENCE: 610

Met Asp Tyr Lys Ser Ser Leu Ile Gln Asp Gly Asn Pro Met Glu Asn
1               5                   10                  15

Leu Glu Lys Gln Leu Ile Cys Pro Ile Cys Leu Glu Met Phe Thr Lys
            20                  25                  30

Pro Val Val Ile Leu Pro Cys Gln His Asn Leu Cys Arg Lys Cys Ala
        35                  40                  45

Asn Asp Ile Phe Gln Ala Ala Asn Pro Tyr Trp Thr Ser Arg Gly Ser
    50                  55                  60

Ser Val Ser Met Ser Gly Gly Arg Phe Arg Cys Pro Thr Cys Arg His
65                  70                  75                  80

Glu Val Ile Met Asp Arg His Gly Val Tyr Gly Leu Gln Arg Asn Leu
                85                  90                  95

Leu Val Glu Asn Ile Ile Asp Ile Tyr Lys Gln Glu Cys Ser Ser Arg
            100                 105                 110

Pro Leu Gln Lys Gly Ser His Pro Met Cys Lys Glu His Glu Asp Glu
        115                 120                 125

Lys Ile Asn Ile Tyr Cys Leu Thr Cys Glu Val Pro Thr Cys Ser Met
    130                 135                 140

Cys Lys Val Phe Gly Ile His Lys Ala Cys Glu Val Ala Pro Leu Gln
145                 150                 155                 160

Ser Val Phe Gln Gly Gln Lys Thr Glu Leu Asn Asn Cys Ile Ser Met
                165                 170                 175

Leu Val Ala Gly Asn Asp Arg Val Gln Thr Ile Ile Thr Gln Leu Glu
            180                 185                 190

Asp Ser Arg Arg Val Thr Lys Glu Asn Ser His Gln Val Lys Glu Glu
        195                 200                 205
```

-continued

```
Leu Ser Gln Lys Phe Asp Thr Leu Tyr Ala Ile Leu Asp Glu Lys Lys
    210             215             220

Ser Glu Leu Leu Gln Arg Ile Thr Gln Glu Gln Glu Lys Lys Leu Ser
225             230             235             240

Phe Ile Glu Ala Leu Ile Gln Gln Tyr Gln Glu Gln Leu Asp Lys Ser
            245             250             255

Thr Lys Leu Val Glu Thr Ala Ile Gln Ser Leu Asp Glu Pro Gly Gly
            260             265             270

Ala Thr Phe Leu Leu Thr Ala Lys Gln Leu Ile Lys Ser Ile Val Glu
        275             280             285

Ala Ser Lys Gly Cys Gln Leu Gly Lys Thr Glu Gln Gly Phe Glu Asn
    290             295             300

Met Asp Phe Phe Thr Leu Asp Leu Glu His Ile Ala Asp Ala Leu Arg
305             310             315             320

Ala Ile Asp Phe Gly Thr Asp Glu Glu Glu Glu Phe Ile Glu Glu
            325             330             335

Glu Asp Gln Glu Glu Glu Glu Ser Thr Glu Gly Lys Glu Glu Gly His
            340             345             350

Gln
```

```
<210> SEQ ID NO 611
<211> LENGTH: 1886
<212> TYPE: DNA
<213> ORGANISM: Mus musculus

<400> SEQUENCE: 611
agaagtcggg ggtcagggga cgaagacaaa gaggatccga gtgggtttgg agacaaagac      60
ttggtgtgac gcaggtgggc gagacagtcg catttcaaag caatatggat tataaatcta     120
gcctgattcc tgatggaaac gctatggaga acctggagaa gcagctgatc tgccccatct     180
gcctggagat gtttaccaag cctgtggtca tcctgccctg ccaacacaac ctctgccgga     240
agtgtgccaa cgacatcttc aggctgcga atccctactg gaccaaccgc ggtggctcag      300
tgtccatgtc tggaggtcgt ttccgttgcc cctcgtgccg ccatgaagtg atcatggacc     360
ggcacggggt gtacggcctg cagaggaacc tgctggtgga aaacatcatt gacatctaca     420
agcaggagtg ctccagtcgg cccctgcaga aaggcagcca cccgatgtgc aaggaacacg     480
aagacgagaa aatcaacatc tactgtctca cgtgtgaggt gcctacttgc tccttgtgca     540
aggtgtttgg ggctcaccag gcctgtgagg ttgcccctttt gcaaagcatc ttccaaggac     600
agaagactga gctgagtaac tgcatctcca tgctggtggc gggcaacgac cgagtgcaga     660
cgatcatctc tcagctggag gactcctgca gagtgaccaa ggagaatagc caccaggtga     720
aggaggagct gagtcagaag tttgacaccc tctacgccat cctggacgag aagaagagcg     780
agctgctgca gcggatcacg caggagcagg aggagaagct gggcttcatc gaggctctga     840
tcctccagta cagggagcag ctggaaaagt ccaccaaact tgtggagacc gccatccagt     900
ccctggatga gcccggaggg gctaccttcc tctcaagtgc caagcagctc atcaagagca     960
ttgtagaagc ctccaagggc tgccagctgg ggaagacaga gcaaggcttt gagaacatgg    1020
actactttac tctggactta gaacacatag cagaggcctt gagggccatt gactttggga    1080
cagatgagga ggaggaggag gaggagttta cagaagagga ggctgatgag gaagagggcg    1140
tgaccacaga gggtaaagaa gaacaccaat gaagaaggat atgagtgaga cacgctctgg    1200
acgcagagac ggggggaggtg ggggcaggcc catctcggga gggggttagg gctccttggg    1260
```

```
gggtacaata gggaagtgtg tcttctctct gctcagagag cagggactag catagggctc      1320
cccaccactg tgtccagcag ctgctgaaac acaattggaa atgtatccaa aacgtcacag      1380 gacactttc tacgttggtg cgaaatgaaa tattttgtat gttttttaaaa tgtgattttt      1440 gtatatactt gtatatgtat gccaatttgg tgcttttttgt acgagaactt ttgtatgatc      1500
acgcctggtc attgtgtgac tggcgattgt cacaaagtgg gaaggaagcc aagacaatag      1560
agatgcctac ttcctttcct tggtgggagg gctgggtctc actcggtggc ctagagaggg      1620
gcaatgtact gtacagtgcc catccccaaa catgggata ggactgaatt tgtgttatat       1680
gttgttttgc acaaggggct gggccttggg gcacacaccc tttgatccca gcactctgga      1740
ggcagaggca gttggatctc tatgagttca aggccagcct ggtctacatg gagagttaca      1800
ggccagccag agctacatag agagactctg cctcaaaaat aaaaatgaaa aagaataaaa      1860
aataaactca caatgctctt ttcctg                                          1886
```

```
<210> SEQ ID NO 612
<211> LENGTH: 355
<212> TYPE: PRT
<213> ORGANISM: Mus musculus

<400> SEQUENCE: 612

Met Asp Tyr Lys Ser Ser Leu Ile Pro Asp Gly Asn Ala Met Glu Asn
1               5                   10                  15

Leu Glu Lys Gln Leu Ile Cys Pro Ile Cys Leu Glu Met Phe Thr Lys
            20                  25                  30

Pro Val Val Ile Leu Pro Cys Gln His Asn Leu Cys Arg Lys Cys Ala
        35                  40                  45

Asn Asp Ile Phe Gln Ala Ala Asn Pro Tyr Trp Thr Asn Arg Gly Gly
        50                  55                  60

Ser Val Ser Met Ser Gly Gly Arg Phe Arg Cys Pro Ser Cys Arg His
65                  70                  75                  80

Glu Val Ile Met Asp Arg His Gly Val Tyr Gly Leu Gln Arg Asn Leu
                85                  90                  95

Leu Val Glu Asn Ile Ile Asp Ile Tyr Lys Gln Glu Cys Ser Ser Arg
            100                 105                 110

Pro Leu Gln Lys Gly Ser His Pro Met Cys Lys Glu His Glu Asp Glu
        115                 120                 125

Lys Ile Asn Ile Tyr Cys Leu Thr Cys Glu Val Pro Thr Cys Ser Leu
        130                 135                 140

Cys Lys Val Phe Gly Ala His Gln Ala Cys Glu Val Ala Pro Leu Gln
145                 150                 155                 160

Ser Ile Phe Gln Gly Gln Lys Thr Glu Leu Ser Asn Cys Ile Ser Met
                165                 170                 175

Leu Val Ala Gly Asn Asp Arg Val Gln Thr Ile Ile Ser Gln Leu Glu
            180                 185                 190

Asp Ser Cys Arg Val Thr Lys Glu Asn Ser His Gln Val Lys Glu Glu
        195                 200                 205

Leu Ser Gln Lys Phe Asp Thr Leu Tyr Ala Ile Leu Asp Glu Lys Lys
        210                 215                 220

Ser Glu Leu Leu Gln Arg Ile Thr Gln Glu Gln Glu Lys Leu Gly
225                 230                 235                 240

Phe Ile Glu Ala Leu Ile Leu Gln Tyr Arg Glu Gln Leu Glu Lys Ser
                245                 250                 255
```

```
Thr Lys Leu Val Glu Thr Ala Ile Gln Ser Leu Asp Glu Pro Gly Gly
            260                 265                 270

Ala Thr Phe Leu Ser Ser Ala Lys Gln Leu Ile Lys Ser Ile Val Glu
            275                 280                 285

Ala Ser Lys Gly Cys Gln Leu Gly Lys Thr Glu Gln Gly Phe Glu Asn
            290                 295                 300

Met Asp Tyr Phe Thr Leu Asp Leu Glu His Ile Ala Glu Ala Leu Arg
305                 310                 315                 320

Ala Ile Asp Phe Gly Thr Asp Glu Glu Glu Glu Glu Glu Phe Thr
                325                 330                 335

Glu Glu Glu Ala Asp Glu Glu Gly Val Thr Thr Glu Gly Lys Glu
            340                 345                 350

Glu His Gln
        355
```

<210> SEQ ID NO 613
<211> LENGTH: 22
<212> TYPE: DNA
<213> ORGANISM: Artificial sequence
<220> FEATURE:
<223> OTHER INFORMATION: Primer

<400> SEQUENCE: 613
tgtctcacgt gtgaggtgcc ta                                              22

<210> SEQ ID NO 614
<211> LENGTH: 23
<212> TYPE: DNA
<213> ORGANISM: Artificial sequence
<220> FEATURE:
<223> OTHER INFORMATION: Primer

<400> SEQUENCE: 614
caccagcatg gagatgcagt tac                                             23

<210> SEQ ID NO 615
<211> LENGTH: 20
<212> TYPE: DNA
<213> ORGANISM: Artificial sequence
<220> FEATURE:
<223> OTHER INFORMATION: Primer

<400> SEQUENCE: 615
tgtgtccgtc gtggatctga                                                 20

<210> SEQ ID NO 616
<211> LENGTH: 21
<212> TYPE: DNA
<213> ORGANISM: Artificial sequence
<220> FEATURE:
<223> OTHER INFORMATION: Primer

<400> SEQUENCE: 616
ttgctgttga agtcgcagga g                                               21

<210> SEQ ID NO 617
<211> LENGTH: 21
<212> TYPE: DNA
<213> ORGANISM: Artificial sequence
<220> FEATURE:
<223> OTHER INFORMATION: Sense strand of siRNA

<400> SEQUENCE: 617

-continued guuggugcga aaugaaauat t                                                              21

<210> SEQ ID NO 618
<211> LENGTH: 21
<212> TYPE: DNA
<213> ORGANISM: Artificial sequence
<220> FEATURE:
<223> OTHER INFORMATION: Antisense strand of siRNA

<400> SEQUENCE: 618
uauuucauuu cgcaccaact t                                                              21

<210> SEQ ID NO 619
<211> LENGTH: 14
<212> TYPE: RNA
<213> ORGANISM: Artificial sequence
<220> FEATURE:
<223> OTHER INFORMATION: A part of an antisense strand of siRNA

<400> SEQUENCE: 619
aacaucucca ggca                                                                      14

<210> SEQ ID NO 620
<211> LENGTH: 16
<212> TYPE: RNA
<213> ORGANISM: Artificial sequence
<220> FEATURE:
<223> OTHER INFORMATION: A part of an antisense strand of siRNA

<400> SEQUENCE: 620
uccauguucu caaagc                                                                    16

<210> SEQ ID NO 621
<211> LENGTH: 17
<212> TYPE: RNA
<213> ORGANISM: Artificial sequence
<220> FEATURE:
<223> OTHER INFORMATION: A part of an antisense strand of siRNA

<400> SEQUENCE: 621
uagaaaagug uccugug                                                                   17

<210> SEQ ID NO 622
<211> LENGTH: 13
<212> TYPE: RNA
<213> ORGANISM: Artificial sequence
<220> FEATURE:
<223> OTHER INFORMATION: A part of an antisense strand of siRNA

<400> SEQUENCE: 622
aagcaccaaa uug                                                                       13

<210> SEQ ID NO 623
<211> LENGTH: 15
<212> TYPE: RNA
<213> ORGANISM: Artificial sequence
<220> FEATURE:
<223> OTHER INFORMATION: A part of an antisense strand of siRNA

<400> SEQUENCE: 623
acaacauaua acaca                                                                     15

<210> SEQ ID NO 624
<211> LENGTH: 19
<212> TYPE: RNA
<213> ORGANISM: Artificial sequence -continued

```
<220> FEATURE:
<223> OTHER INFORMATION: Sense strand of siRNA

<400> SEQUENCE: 624
cuaucugccu ggagaugua                                               19

<210> SEQ ID NO 625
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 625
gugccuggag auguuuacu                                               19

<210> SEQ ID NO 626
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 626
gccuggagau guuuaccau                                               19

<210> SEQ ID NO 627
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 627
ggcucagugu ccaugucuu                                               19

<210> SEQ ID NO 628
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 628
gaucaacauc uacugucuu                                               19

<210> SEQ ID NO 629
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 629
caucuacugu cucacguga                                               19

<210> SEQ ID NO 630
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 630
ucuacugucu cacgugugu                                               19
```

<210> SEQ ID NO 631
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 631
guacugucuc acgugugau                                                        19

<210> SEQ ID NO 632
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 632
gcuccaugcu gguggcggu                                                        19

<210> SEQ ID NO 633
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 633
ggcuuugaga acauggaca                                                        19

<210> SEQ ID NO 634
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 634
gcuuugagaa cauggacua                                                        19

<210> SEQ ID NO 635
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 635
ccauugacuu ugggacagu                                                        19

<210> SEQ ID NO 636
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 636
gcacaggaca cuuuucuau                                                        19

<210> SEQ ID NO 637
<211> LENGTH: 19
<212> TYPE: RNA
<213> ORGANISM: Artificial sequence
<220> FEATURE:
<223> OTHER INFORMATION: Sense strand of siRNA -continued

<400> SEQUENCE: 637
cacaggacac uuuucuacu                                                           19

<210> SEQ ID NO 638
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 638
cuuguauaug uaugccaaa                                                           19

<210> SEQ ID NO 639
<211> LENGTH: 19
<212> TYPE: RNA
<213> ORGANISM: Artificial sequence
<220> FEATURE:
<223> OTHER INFORMATION: Sense strand of siRNA

<400> SEQUENCE: 639
guguaugcca auuuggugu                                                           19

<210> SEQ ID NO 640
<211> LENGTH: 22
<212> TYPE: DNA
<213> ORGANISM: Artificial sequence
<220> FEATURE:
<223> OTHER INFORMATION: Primer

<400> SEQUENCE: 640
cgtgtgcaga ccatcatcac tc                                                       22

<210> SEQ ID NO 641
<211> LENGTH: 23
<212> TYPE: DNA
<213> ORGANISM: Artificial sequence
<220> FEATURE:
<223> OTHER INFORMATION: Primer

<400> SEQUENCE: 641
caacgtgtca aacttctggc tca                                                      23

<210> SEQ ID NO 642
<211> LENGTH: 20
<212> TYPE: DNA
<213> ORGANISM: Artificial sequence
<220> FEATURE:
<223> OTHER INFORMATION: Primer

<400> SEQUENCE: 642
gcaccgtcaa ggctgagaac                                                          20

<210> SEQ ID NO 643
<211> LENGTH: 19
<212> TYPE: DNA
<213> ORGANISM: Artificial sequence
<220> FEATURE:
<223> OTHER INFORMATION: Primer

<400> SEQUENCE: 643
tggtgaagac gccagtgga                                                           19